US011373730B2

(12) United States Patent
Zhao et al.

(10) Patent No.: US 11,373,730 B2
(45) Date of Patent: Jun. 28, 2022

(54) DETERMINATION OF MICROORGANISM OPERATIONAL TAXONOMIC UNIT AND SEQUENCE-ASSISTED SEPARATION

(71) Applicant: PERFECT (CHINA) CO., LTD., Guangdong (CN)

(72) Inventors: Liping Zhao, Shanghai (CN); Jing Wang, Shanghai (CN); Menghui Zhang, Shanghai (CN)

(73) Assignee: Perfect (China) Co., Ltd., Guangdong (DE)

( * ) Notice: Subject to any disclaimer, the term of this patent is extended or adjusted under 35 U.S.C. 154(b) by 883 days.

(21) Appl. No.: 16/193,768

(22) Filed: Nov. 16, 2018

(65) Prior Publication Data

US 2019/0194740 A1 Jun. 27, 2019

Related U.S. Application Data

(63) Continuation-in-part of application No. PCT/CN2017/084474, filed on May 16, 2017.

(30) Foreign Application Priority Data

May 19, 2016 (CN) .......................... 201610333530.7

(51) Int. Cl.
| C12P 19/34 | (2006.01) |
| G16B 25/10 | (2019.01) |
| G16B 20/00 | (2019.01) |
| G16B 25/20 | (2019.01) |
| C12Q 1/6869 | (2018.01) |
| G16B 30/00 | (2019.01) |

(52) U.S. Cl.
CPC ........... *G16B 25/10* (2019.02); *C12Q 1/6869* (2013.01); *G16B 20/00* (2019.02); *G16B 25/20* (2019.02); *G16B 30/00* (2019.02)

(58) Field of Classification Search
CPC ........ G16B 25/10; G16B 25/20; G16B 20/00; G16B 30/00; C12Q 1/6869
See application file for complete search history.

(56) References Cited

U.S. PATENT DOCUMENTS

2008/0261222 A1   10/2008  Rogan
2016/0103958 A1*  4/2016   Hebert ................... G16B 10/00
                                                           707/737

FOREIGN PATENT DOCUMENTS

| CN | 102477460 A | 5/2012 |
| CN | 102517392 A | 6/2012 |
| CN | 106055924 A | 10/2016 |
| WO | 2017/198137 A1 | 11/2017 |

OTHER PUBLICATIONS

Morgan et al. Improved Inference of Taxonomic Richness from Environmental DNA. Aug. 26, 2013, PLOS ONE, 8, 8, e71974 (Year: 2013).*
Guo et al. Taxonomic Precision of Different Hypervariable Regions of 16S rRNA Gene and Annotation Methods for Functional Bacterial Groups in Biological Wastewater Treatment, Oct. 16, 2013, PLOS ONE, 8, 10, e76185 (Year: 2013).*
Carporaso et al., Global patterns of 16S rRNA diversity at a depth of millions of sequences per sample, PNAS, Mar. 15, 2011, vol. 108, Suppl. 1, pp. 4516-4522.
Chinese Office Action, dated Feb. 1, 2018, issued in corresponding Chinese Application No. 201610333530.7, 3 pages.
Taiwanese Office Action, dated Aug. 28, 2018, issued in Taiwanese Application No. 106116361, 7 pages.
Fadrosh et al., An improved dual-indexing approach for multiplexed 16S rRNA gene sequencing on the Illumina MiSeq platform, Microbiome 2014, 2:6, 7 pages.
Goodrich et al., Conducting a Microbiome Study, Cell 158, Jul. 17, 2014, pp. 250-262.
McMurdie et al., Waste Not, Want Not: Why Rarefying Microbiome Data is Inadmissible, PLOS Computational Biology, Apr. 2014, vol. 10, Issue 4, pp. 1-12.
Article: A framework for human microbiome research, doi:10.1038/nature11209, Nature, vol. 486, Jun. 14, 2012, pp. 215-221.
International Search Report (with English Translation), dated Aug. 7, 2017 in International Application No. PCT/CN2017/084474, 8 pages.
Written Opinion of the International Searching Authority (with English Translation), dated Aug. 7, 2017 in International Application No. PCT/CN2017/084474, 9 pages.
Preheim et al., Distribution-Based Clustering: Using Ecology to Refine the Operational Taxonomic Unit, Applied and Environmental Microbiology, Nov. 2013, vol. 79, No. 21, pp. 6593-6603.
Schloss et al., Assessing and Improving Methods Used in Operational Taxonomic Unit-Based Approaches for 16S rRNA Gene Sequence Analysis, Applied and Environmental Microbiology, May 2011, vol. 77, No. 10, pp. 3219-3226.
Fei et al., An opportunistic pathogen isolated from the gut of an obese human causes obesity in germfree mice, International Society for Microbial Ecology, The ISME Journal (2013) 7, pp. 880-884.

(Continued)

*Primary Examiner* — Kenneth R Horlick
(74) *Attorney, Agent, or Firm* — Dinsmore & Shohl LLP

(57) ABSTRACT

A method in which a microorganism operational taxonomic unit (OTU) in a sample is defined based on a DNA sequence of a system generation information gene of microorganism in the sample. In the method, qualified sequence segments are obtained by means of processing and reading of an original sequence; the segments are sorted according to a relative abundance value of each segment; and only the qualified sequences with the high abundance values are used to obtain the temporary OTU. The qualified sequences with the low abundance values are reallocated; and the qualified sequence can be distributed to the proper temporary OTU respectively when a sequence similarity degree between the qualified sequence and an OTU sequence reaches at least 97%. The present disclosure also provides a sequence-assisted microorganism separation method.

5 Claims, 17 Drawing Sheets

Specification includes a Sequence Listing.

(56) References Cited

OTHER PUBLICATIONS

Zhang et al., Dietary Modulation of Gut Microbiota Contributes to Alleviation of Both Genetic and Simple Obesity in Children, EBioMedicine 2 (2015), pp. 968-984.

Chen et al., A Comparison of Methods for Clustering 16S rRNA Sequences into OTUs, PLoS ONE 8(8): 370837, Aug. 2013, vol. 8, Issue 8, pp. 1-10.

Bonder et al., Comparing clustering and pre-processing in taxonomy analysis, Bioinformatics, vol. 28, No. 22 2012, pp. 2891-2897, Advance Access publication Sep. 8, 2012.

Edgar, UPARSE: highly accurate OTU sequences from microbial amplicon reads, 2013, Nature Methods: doi:10.1038/nmeth.264, 35 pages.

Kozich et al., Development of a Dual-Index Sequencing Strategy and Curation Pipeline for Analyzing Amplicon Sequence Data on the MiSeq Illumina Sequencing Platform, Applied and Environmental Microbiology, Sep. 2013, vol. 2013, vol. 79, No. 17, pp. 5112-5120.

Caporaso et al., QIIME allows analysis of high-throughput community sequencing data, Nat Methods, May 2010; 7(5) (Published in final edited form as: 335-336. doi:10.1038/nmeth.f.303); 4 pages.

Klindworth et al., Evaluation of general 16S ribosomal RNA gene PCR primers for classical and next-generation sequencing-based diversity studies, Nucleic Acids Research, 2013, vol. 41, No. 1, doi:10.1093/nar/gks808, Published online Aug. 28, 2012, pp. 1-11.

Bokulich et al., Quality-filtering vastly improves diversity estimates from Illumina amplicon sequencing, HHS Public Access, Author manuscript, Published in final edited form as: Nat Methods. Jan. 2013; 10(1):57-59. doi:10.1038/nmeth.2276, pp. 1-7.

Schirmer et al., Insight into biases and sequencing errors for amplicon sequencing with the Illumina MiSeq platform, Nucleic Acids Research, 2015, vol. 43, No. 6, doi:10.1093/nar/gku1341, Published online Jan. 13, 2015, pp. 1-16.

Schloss et al., Introducing mothur: Open-Source, Platform-Independent Community-Supported Software for Describing and Comparing Microbial Communities, Applied and Environmental Microbiology, vol. 75, No. 23, Dec. 2009, pp. 7537-7541.

Aronesty, Comparison of Sequencing Utility Programs, The Open Bioinformatics Journal, vol. 7, Jan. 13, 9 pages.

Nikolenko et al., BayesHammer: Bayesian clustering for error correction in single-cell sequencing, BMC Genomics 2013, 14(Suppl 1):S7, http://www.biomedcentral.com/1471-2164/14/S1/S7, pp. 1-11.

Masella et al., PANDAseq: PAired-eND Assembler for Illumina sequences, BMC Bioinformatics 2012, 13:31, http://www.biomedcentral.com/1471-2105/13/31, pp. 1-7.

Edgar, Search and clustering orders of magnitude faster than BLAST, Bioinformatics, Applications Note, vol. 26, No. 19 2010, pp. 2460-2461, doi:10.1093/bioinformatics/btq461 (Advance Access publication Aug. 12, 2010).

Haas et al., Chimeric 16S rRNA sequence formation and detection in Sanger and 454-pyrosequenced PCR amplicons, Genome Research, www.genome.org, 21:494-504, copyright 2011 by Cold Spring Harbor Laboratory Press.

Edgar et al., UCHIME improves sensitivity and speed of chimera detection, Bioinformatics, Original Paper, vol. 27, No. 16 2011, pp. 2194-2200, doi:10.1093/bioinformatics/btr381 (Advance Access publication Jun. 23, 2011).

Chao, Nonparametric Estimation of the Number of Classes in a Population, Scandinavian Journal of Statistics, vol. 11, No. 4 (1984), pp. 265-270.

C.E. Shannon, A Mathematical Theory of Communication, Bell System Technical Journal, vol. 27, pp. 379-423, 623-656, Jul. Oct. 1948. Presented by Andrew Jurik, Theory Lunch, Nov. 6, 2008, 22 pages.

Lozupone et al., UniFrac: a New Phylogenetic Method for Comparing Microbial Communities, Applied and Environmental Microbiology, vol. 71, No. 12, Dec. 2005, p. 8228-8235.

Mantel, The Detection of Disease Clustering and a Generalized Regression Approach, Cancer Research 27 Part 1, vol. 27, No. 2, Feb. 1967, pp. 209-220.

DePristo et al., A framework for variation discovery and genotyping using next-generation DNA sequencing data, HHS Public Access, Nat Genet. May 2011; 43(5): 491-498, doi:10.1038/ng.806.

Edgar et al., Error filtering, a pair assembly and error correction for next-generation sequencing reads, Bioinformatics, 31(21), (2015) 3476-3481. DOI: 10.1093/bioinformatics/btv401, 8 pages.

Caporaso et al., Ultra-high-through microbial community analysis on the Illumina HiSeq and MiSeq platforms, The ISME Journal (2012) 6, pp. 1621-1624.

Roeselers et al., Microbial biogeography of drinking water: patterns in phylogenetic diversity across space and time, Environmental Microbiology, Jan. 2015, 23 pages.

D. Savio et al., Bacterial diversity along a 2600 km river continuum, Environmental Microbiology (2015) 7(12), pp. 4994-5007.

D. Herlemann et al., Transitions in bacterial communities along the 2000 km salinity gradient of the Baltic Sea, The ISME Journal (2011) 5, 1571-1579.

Cole et al., Ribosomal Database Project: data and tools for high throughout rRNA analysis, Nucleic Acids Research, 2014, vol. 42, Database issue, pp. D633-D642, doi:10.1093/nar/ght1244. Published online Nov. 27, 2013.

Quast et al., SILVA ribosomal RNA gene database project: improved data processing and web-based tools, Nucleic Acids Research, 2013, vol. 41, Database Issue, doi:10.1093/nar/gks1219, pp. D590-D596. Published online Nov. 28, 2012.

T.Z. DeSantis et al., Greengenes: Chimera-checked 16S rRNA gene database and workbench compatible with ARB, Applied and Environmental Microbiology, 72(7), Jul. 2006, 15 pages.

Office Action for Malaysian Application No. PI 2018001991 dated Nov. 12, 2020.

* cited by examiner

Centroids of OTUs picked by Qiime

Centroids of OTUs picked by Mothur

Centroids of OTUs picked by Usearch

Abundant uniques only

| Sequence |
|---|
| SEQ ID NO: 1<br>GAGAGTTTGATCCTGGCTCAGGATGAACGCTGGCGGCGTGCTTAACACATGCAAGTCGAACGGGAATTACTTTATTGAAACTTCGGTCGATATGATTTAATTCTAGTGGCGGACGGGTGAGTAACGCGTGGGTAA<br>CCTGCCTTGTACAGGGGGATAACAGTCAGAAATGACTGCTAATACCGCATAAGCGCACAGGACCGCATGGTCCGGTGTGAAAAACTCCGGTGGTATAAGATGGACCCGCGTTGGATTAGCTAGTTGGTGAGGTA<br>ACGGCCCACCAAGGCGACGATCCATAGCCGGCCTGAGAGGGTGAACGGCCACATTGGGACTGAGACACGGCCCAGACTCCTACGGGAGGCAGCAGTGGGGAATATTGCACAATGGGGGAAACCCTGATGCA<br>GCGACGCCGCGTGAAGGAAGAAGTATCTCGGTATGTAAACTTCTATCAGCAGGGAAGAAAATGACGGTACCTGACTAAGAAGCCCCGGCTAACTACGTGCCAGCAGCCGCGGTAATACGTAGGGGGCAAGCGT<br>TATCCGGATTTACTGGGTGTAAAGGGAGCGTAGACGGATGGACAAGTCTGATGTGAAAGGCTGGGGCTCAACCCCGGGACTGCATTGGAAACTGCCCGTCTTGAGTGCCGGAGAGGTAAGCGGAATTCCTAGT<br>GTAGCGGTGAAATGCGTAGATATTAGGAGGAACACCAGTGGCGAAGGCGGCTTACTGGACGGTAACTGACGTTGAGGCTCGAAAGCGTGGGGAGCAAACAGGATTAGATACCCTGGTAGTCCACGCGGTAAA<br>CGATGAATGCTAGGTGTCGGGTGACGAAGTCATTCGGTGCCGCCGCAAACGCATTAAGCATTCCACCTGGGGAGTACGTTCGCAAGAATGAAACTCAAAGGAATTGACGGGGACCCGCACAAGCGGTGGAGCA<br>TGTGGTTTAATTCGAAGCAACGCGAAGAACCTTACCAAGTCTTGACATCCTTCTGACCGGAACTTAACCGTTCCTTCCCTTCGGGGCAGAAGTGACAGGTGGTGCATGGTTGTCGTCAGCTCGTGTCGTGAGATG<br>TTGGGTTAAGTCCCGCAACGAGCGCAACCCCTATCCTCAGTAGCCAGCATATAAGATGGGCACTCTGTGGAGACTGCCAGGGATAACCTGGAGGAAGGCGGGGATGACGTCAAATCATCATGCCCCTTATGATTT<br>GGGCTACACACGTGCTACAATGGCGTAAACAAAGGGAAGCGAACCTGCGAGGGTGGGCAAATCCCAAAAATAACGTCCCAGTTCGGACTGTAGTCTGCAACCCGACTACACGAAGCTGGAATGCTAGTAATC<br>GCGGATCAGAATGCCGCGGTGAATACGTTCCCGGGTCTTGTACACACCGCCCGTCACACCATGGGAGTCAGTAACGCCCGAAGTCAGTGACCTAACCGCAAGGAAGGAGCTGCCGAAGGCGGGACCGATGACT<br>GGGGTGAAGTCGTAACAAGGTAGCCG |
| SEQ ID NO: 2<br>GAGAGTTTGATCCTGGCTCAGGACGAACGCTGGCGGCGTGCCTAACACATGCAAGTCGAACGGAGAATTTTATTTCGGTAGAATTCTTAGTGGCGAACGGGTGAGTAACGCGTAGGCAACCTGCCCTTTAGACG<br>GGGACAACATTCCGAAAGGAGTGCTAATACCGGATGTGATCATCTTGCCGCATGGCAGGATGAAGAAAGATGGCCTCTACAAGTAAGCTATCGCTAAAGGATGGGCCTGCGTCTGATTAGCTAGTTGGTAGTGTA<br>ACGGACTACCAAGGCGATGATCAGTAGCCGGTCTGAGAGGATGAACGGCCACATTGGGACTGAGACACGGCCCAAACTCCTACGGGAGGCAGCAGTGAGGAATATTGGCAATGGGCGAAAGTCTGACGGA<br>GCAACGCCGCGTGAACGATGAAGGTCTTCGGATTGTAAAGTTCTGTGATCCGGGACGAAGGCATCAATTGAGAATATTGATTGATGTTGACGGTACCGGAAAAGCAAGCCACGGCTAACTACGTGCCAGCAGCC<br>GCGGTAATACGTAGGTGGCAAGCGTTGTCCGGAATTATTGGGCGTAAAGCGCGCGCAGGCGGCCGTGCAAGTCCATCTTAAAAGCGTGGGGCTTAACCCCATGAGGGGATGGAAACTGCAGGGCTGGAGTGT<br>CGGAGGGGAAAGTGGAATTCCTAGTGTAGCGGTGAAATGCGTAGATATTAGGAAGAACACCGGTGGCGAAGGCGACTTTCTAGACGACAACTGACGCTGAGGCGCGAAAGCGTGGGGAGCAAACAGGATTA<br>GATACCCTGGTAGTCCACGCCGTAACGATGGATACTAGGTGTAGGAGGTATCGACCCCTTCTGTGCCGGAGTTAACGCAATAAGTATCCCGCCTGGGAAGTACGATCGCAAGATTAAAACTCAAAGGAATTGACG<br>GGGGCCCGCACAAGCGGTGGAGTATGTGGTTTAATTCGACGCAACGCGAAGAACCTTACCAAGCCTTGACATTGATCGCAATCTGCAGAAATGCGGAGTTCCTCTTCGGAGGACGAGAAAACAGGTGGTGCAC<br>GGCTGTCGTCAGCTCGTGTCGTGAGATGTTGGGTTAAGTCCCGCAACGAGCGCAACCCCTATCCTCGTTGCCAGCACGTAAAGGTGGGAACTCAGGAGGACCGCCGGCGACAACCGCGAGGAAGGCGGGG<br>ATGACGTCAAGTCATCATGCCCCTTATGGCTTGGGCTACACACGTACTACAATGGGTGCAACAAAGAGAAGCAAGCTCGCGAGACGGAGCGGACCTCATAAACGCACTCCCAGTTCAGATTGCAGGCTGCAAC<br>CCGCCTGCATGAAGTAGGAATCGCTAGTAATCGCGGGTCAGCATACCGCGGTGAATACGTTCCCGGGCCTTGTACACACCGCCCGTCACACTATGAGAGTCAGAGCACCCAAAGCCGGTGGGATAACCGAAAG<br>GGATCAGCCGTCTAAGGTGGAGCTGATGATTGGAGTGAAGTCGTAACAAGGTAGCCG |
| SEQ ID NO: 3<br>AGAGTTTGATCCTGGCTCAGGATGAACGCTAGCTACAGGCTTAACACATGCAAGTCGAGGGGCAGCATGGACCCAGTTTTGCTGGGTTTGATGGCGACCGGCGCACGGGTGAGTAACGCGTATCCAACCTGCC<br>CTTTACTCCGGGATAGTCTCCTGAAAGGGAGTTTAATACCGGATGTGTTTGTCTTTCCGCATGGGACGCAGACAAATAAAGATTGATTGGTAAAGGATGGGGATGCGTCCCATTAGCTTGTTGGCGGGGTAACGGCC<br>CACCAAGGCGACGATGGGTAGGGGTTCTGAGAGGAAGGTCCCCCACATTGGAACTGAGACACGGTCCAAACTCCTACGGGAGGCAGCAGTGAGGAATATTGGTCAATGGGCGGAAGCCTGAACCAGCCAAG<br>TAGCGTGAAGGATGACGGCCCTACGGGTTGTAAACTTCTTTTATAAGGGAATAAAGTTCGCCACGTGTGGTGTTTTGTATGTACCTTATGAATAAGCATCGGCTAATTCCGTGCCAGCAGCCGCGGTAATACGGAA<br>GATGCGAGCGTTATCCGGATTTATTGGGTTTAAAGGGAGCGTAGGCGGGCTTTTAAGTCAGCGGTCAAATGCCACGGCTCAACCGTGGCCAGCCGTTGAAACTGCAAGCCTTGAGTCTGCACAGGGCACATGG<br>AATTCGTGGTGTAGCGGTGAAATGCTTAGATATCACGAAGAACTCCGATCGCGAAGGCATTGTGCCGGGGACAGACGCTGAAGCTCGAAAGTGCGGGGATCAAACAGGATTAGATACCCTGGTAGTCCGC<br>ACGGTAAACGATGAATGCTCGCTATGGGCGATACAATGTCCGTGGCCAAGCGAAAGCGTTAAGCATTCCACCTGGGGAGTACGCCGGCAACGGTGAAACTCAAAGGAATTGACGGGGGCCCGCACAAGCGGA<br>GGAACATGTGGTTTAATTCGATGATACGCGAGGAACCTTACCCGGGCTTGAATTGCAGGTGCATGAGTCGGAGACGGCTCTTTCCTTCGGGACTCCTGTGAAGGTGCTGCATGGTTGTCGTCAGCTCGTGCCGT<br>GAGGTGTCGGCTTAAGTGCCATAACGAGCGCAACCCTTCTCCCCAGTTGCCATCGGGTAATGCCGGGCCTCTGGGGACACTGCCATCGTAAGATGCGAGGAAGGTGGGGATGACGTCAAATCAGCACGGCCC<br>TTACGTCCGGGGCTACACACGTGTTACAATGGGGGGTACAGAGGGCCGCTGTCCGGTGACGGTCGGCCAATCCCTAAAACTCCTCTCAGTTCGGACTGGAGTCTGCAACCCGACTCCACGAAGCTGGATTCGCT<br>AGTAATCGCGCATCAGCCATGGCGCGGTGAATACGTTCCCGGGCCTTGTACACACCGCCCGTCAAGCCATGAAAGCCGGGGGTGCCTGAAGTCCGTGACCGCGAGGGTCGGCCTAGGGTAAAACTGGTGATTG<br>GGGCTAAGTCGTAACAAGGTAGCC |
| SEQ ID NO: 4<br>GAGAGTTTGATCCTGGCTCAGGATGAACGCTAGCGACAGGCCTAACACATGCAAGTCGAGGGGCAGCGGGGAGGTAGCAATACCTTGCCGGCGACCGGCGCACGGGTGAGTAACACGTATGCAATCCACCT<br>GTAACAGGGGGATAACCCGGAGAAATCCGGACTAATACCCGCATGATATAGGGCTCTCGCATGGATCGGGCCATTAAAGAGAGCAATCTTGGTTACAGACGAGCATGCGTCCCATTAGCCAGTTGGCGGGGTAACG<br>GCCCACCAAGGCGACGATGGATAGGGGTTCTGAGAGGAAGGTCCCCCACATTGGAACTGAGACACGGTCCAAACTCCTACGGGAGGCAGCAGTGAGGAATATTGGTCAATGGTCGGAGACTGAACCAGCCA<br>AGTCGCGTGAGGGAAGACGGCCCTACGGGTTGTAAACCTCTTTTGTCGGAGAGTAAAGTGCGCTACGCGTAGCGTATTGCAAGTATCGAAGAAAAAGCATCGGCTAACTCCGTGCCAGCAGCCGCGGTAATAC<br>GGAGGATGCGAGCGTTATCCGGATTTATTGGGTTTAAAGGGTGCGTAGGCGGCACGCCAAGTCAGCGGTGAAATTTCCGGGCTCAACCCGGACTGTGCCGTTGAAACTGGCGAGCTAGAGTGCACAAGAGGC<br>AGGCGGAATGCGTGGTGTAGCGGTGAAATGCATAGATATCACGCAGAACCCCGATTGCGAAGGCAGCTGCTAGGGTGCGACAGACGCTGAGGCACGAAAGCGTGGGTATCGAACAGGATTAGATACCCTGGT<br>AGTCCACGCAGTAAACGATGAATACTAACTGTTTGCGATACAATGTAAGCGGTACAGCGAAAGCGTTAAGTATTCCACCTGGGGAGTACGCCGGCAACGGTGAAACTCAAAGGAATTGACGGGGGCCCGCACA<br>AGCGGAGGAACATGTGGTTTAATTCGATGATACGCGAGGAACCTTACCCGGGCTCAAACGCAGGGGAATGCCGGTGAAAGTCGGCAGCTAGTAATAGTCACCTGCGAGGTGCTGCATGGTTGTCGTCAGCTC<br>GTGCCGTGAGGTGTCGGCTTAAGTGCCATAACGAGCGCAACCCCTATCGACAGTTACTAACAGGTGGAAGCCGAGGACTCTGTCGAGACTGCCGGCGCAAGCCGCGAGGAAGGTGGGGATGACGTCAAATCAG<br>CACGGCCCTTACGTCCGGGGCGACACACGTGTTACAATGGCAGGTACAGAAGGCAGCCAGTCAGCAATGACGCGGAATCCCGAAAACCTGTCTCAGTTCGGATTGGAGTCTGCAACCCGACTCCATGAAGCT<br>GGATTCGCTAGTAATCGCGCATCAGCCATGGCGCGGTGAATACGTTCCCGGGCCTTGTACACACCGCCCGTCAAGCCATGGAAGCCGGGAGTACCTGAAGCATGCAACCGCAAGGAGCGTACGAAGGTAATACC<br>GGTAACTGGGGCTAAGTCGTAACAAGGTAGCCA |
| SEQ ID NO: 5<br>GAGAGTTTGATCCTGGCTCAGGACGAACGCTGGCGGCGTGCCTAATACATGCAAGTAAAACGCTGAAGAGAGGAGCTTGCTCTTCTTGGATGAGTTGCGAACGGGTGAGTAACGCGTAGGTAACCTGCCTTGT<br>AGCGGGGGATAACTATTGGAAACGATAGCTAATACCGCATAACAATGGATGACTCATGTCATTTATTTGAAAGGGGCAAATGCTCCACTACAAGATGGACCTGCGTTGTATTAGCTAGTAGGTGAGGTAACGGCTC<br>ACCTAGGCGACGATACATAGCCGACCTGAGAGGGTGATCGGCCACACTGGGACTGAGACACGGCCCAGACTCCTACGGGAGGCAGCAGTAGGGAATCTTCGGCAATGGGGGCAACCCTGACCGAGCAACGCC<br>GCGTGAGTGAAGAAGGTTTTCGGATCGTAAAGCTCTGTTGTAAGTCAAGAACGAGTGTGAGAGTGGAAAGTTCACACTGTGACGGTAGCTTACCAGAAAGGGACGGCTAACTACGTGCCAGCAGCCGCGGTAA<br>TACGTAGGTCCCGAGCGTTGTCCGGATTTATTGGGCGTAAAGCGAGCGCAGGCGGTTTGATAAGTCTGAAGTTAAAGGCTGTGGCTCAACCATAGTTCGCTTTGGAAACTGTCAAACTTGAGTGCAGAAGGGGA<br>GAGTGGAATTCCATGTGTAGCGGTGAAATGCGTAGATATATGGAGGAACACCGGTGGCGAAAGCGGCTCTCTGGTCTGTAACTGACGCTGAGGCTCGAAAGCGTGGGGAGCGAACAGGATTAGATACCCTGGT<br>AGTCCACGCCGTAAACGATGAGTGCTAGGTGTTGGATCCTTTCCGGGATTCAGTGCCGCAGCTAACGCATTAAGCACTCCGCCTGGGGAGTACGACCGCAAGGTTGAAACTCAAAGGAATTGACGGGGGCCCG<br>CACAAGCGGTGGAGCATGTGGTTTAATTCGAAGCAACGCGAAGAACCTTACCAGGTCTTGACATCCCGATGCTATTTCTAGAGATAGAAAGTTACTTCGGTACATCGGTGACAGGTGGTGCATGGTTGTCGTCAG<br>CTCGTGTCGTGAGATGTTGGGTTAAGTCCCGCAACGAGCGCAACCCCTATTGTTAGTTGCCATCATTCAGTTGGGCACTCTAGCGAGACTGCCGGTGAATAAACCGGAGGAAGGTGGGGATGACGTCAAATCATCA<br>TGCCCCTTATGACCTGGGCTACACACGTGCTACAATGGTTGGTACAACGAGTTGCGAGTCGGTGACGGCAAGCTAATCTCTTAAAGCCAATCTCAGTTCGGATTGTAGGCTGCAACTCGCCTACATGAAGTCGGA<br>ATCGCTAGTAATCGCGGATCAGCACGCCGCGGTGAATACGTTCCCGGGCCTTGTACACACCGCCCGTCACACCACGAGAGTTTGTAACACCCGAAGTCGGTGAGGTAACCTTTTGGAGCCAGCCGCCTAAGGTG<br>GGATAGATGATTGGGGTGAAGTCGTAACAAGGTAGCCG |
| SEQ ID NO: 6<br>GAGAGTTTGATCCTGGCTCAGGACGAACGCTGGCGGCACGCTTAACACATGCAAGTCGAACGGAGAATATCGAAGCTTGCTTTGATATTCTTAGTGGCGGACGGGTGAGTAACACGTGAGTAACCTGCCTCTGA<br>GAGTGGGATAGCTTCTGGAAACGGATGGTAATACCGCATGAAATCATAGTATCGCATGGTACAATGATCAAAGATTTATCGCTCAGAGATGGACTCGCGTCTGATTAGCTAGTTGGTAAGGTAACGGCTTACCAAG<br>GCGACGATCAGTAGCCGGACTGAGAGGTTGATCGGCCACATTGGGACTGAGACACGGCCCAGACTCCTACGGGAGGCAGCAGTGGGGAATATTGCACAATGGGGGAAACCCTGATGCAGCGATGCCGCGTG<br>GAGGAAGAAGGTTTTCGGATTGTAAACTCCTGTTGAAGAGGACGATAATGACGGTACTCTTTTAGAAAGCTCCGGCTAACTACGTGCCAGCAGCCGCGGTAATACGTAGGGGAGCGAGCGTTGTCCGGAATTACT<br>GGGTGTAAAGGGAGCGTAGGCGGGACGGCAAGTCAGATGTGAAAACTATGGGCTCAACCCATAGACTGCATTTGAAACTGTTGTTCTTGAGTGAGGTAGAGGTAAGCGGAATTCCTGGTGTAGCGGTGAAATG<br>CGTAGAGATCAGGAGGAACATCGGTGGCGAAGGCGGCTTACTGGGCCTTACTGACGCTGAGGCTCGAAAGCGTGGGGAGCAAACAGGATTAGATACCCTGGTAGTCCACGCCGTAAACGATGATTACTAGGT<br>GTGGGGGGACTGACCCCTTCCGTGCCGCAGCTAACACAATAAGTAATCCACCTGGGGAGTACGGCCGCAAGGTTGAAACTCAAAGGAATTGACGGGGGCCCGCACAAGCGGTGGAGTATGTGGTTTAATTCGA<br>AGCAACGCGAAGAACCTTACCAGGTCTTGACATCGAGTGACGTACCTAGAGATAGGTATTTTCTTCGGAACACAAAGACAGGTGGTGCATGGTTGTCGTCAGCTCGTGTCGTGAGATGTTGGGTTAAGTCCCGC<br>AACGAGCGCAACCCCTTACCATTAGTTGCTACGCAAGAGCACTCTAATGGGACTGCCGTTGACAAAACGGAGGAAGGTGGGGATGACGTCAAATCATCATGCCCCTTATGACCTGGGCTACACACGTACTACAATG<br>GCAATATAACAGAGGGAAGCAATACAGCGATGTGGAGCAAATCCCCAAAAATTGTCCCAGTTCAGATTGCAGGCTGCAACTCGCCTGCATGAAGTCGAATTGCTAGTAATCGCAGATCAGCATGCTGCGGTGAA<br>TACGTTCCCGGGCCTTGTACACACCGCCCGTCACACCATGGGAGTCGGTAACACCCAAAGCCGGTCGTCTAACCTTCGGGAGGACGCCGTCTAAGGTGGGATTGATGACTGGGGTGAAGTCGTAACAAGGTAA<br>CCG |

| Sequence |
|---|
| SEQ ID NO: 13 |
| GAGAGTTTGATCCTGGCTCAGATTGAACGCTGGCGGCAGGCCTAACACATGCAAGTCGAGCGGTAGCACAGAGAGCTTGCTCTCGGGTGACGAGCGGCGGACGGGTGAGTAATGTCTGGGAAACTGCCTG<br>ATGGAGGGGGATAACTACTGGAAACGGTAGCTAATACCGCATAATGTCGCAAGACCAAAGTGGGGGACCTTCGGGCCTCATGCCATCAGATGTGCCCAGATGGGATTAGCTAGTAGGTGGGGTAACGGCTCA<br>CCTAGGCGACGATCCCTAGCTGGTCTGAGAGGATGACCAGCCACACTGGAACTGAGACACGGTCCAGACTCCTACGGGAGGCAGCAGTGGGGAATATTGCACAATGGGCGCAAGCCTGATGCAGCCATGCC<br>GCGTGTGTGAAGAAGGCCTTCGGGTTGTAAAGCACTTTCAGCGGGGAGGAAGGCGTTAAGGTTAATAACCTTGGCGATTGACGTTACCCGCAGAAGAAGCACCGGCTAACTCCGTGCCAGCAGCCGCGGTA<br>ATACGGAGGGTGCAAGCGTTAATCGGAATTACTGGGCGTAAAGCGCACGCAGGCGGTCTGTCAAGTCGGATGTGAAATCCCCGGGCTCAACCTGGGAACTGCATTCGAAACTGGCAGGCTAGAGTCTTGTAG<br>AGGGGGGTAGAATTCCAGGTGTAGCGGTGAAATGCGTAGAGATCTGGAGGAATACCGGTGGCGAAGGCGGCCCCCTGGACAAAGACTGACGCTCAGGTGCGAAAGCGTGGGGAGCAAACAGGATTAGAT<br>ACCCTGGTAGTCCACGCCGTAAACGATGTCGATTTGGAGGTTGTGCCCTTGAGGCGTGGCTTCCGGAGCTAACGCGTTAAATCGACCGCCTGGGGAGTACGGCCGCAAGGTTAAAACTCAAATGAATTGACG<br>GGGGCCCGCACAAGCGGTGGAGCATGTGGTTTAATTCGATGCAACGCGAAGAACCTTACCTGGTCTTGACATCCACAGAACTTAGCAGAGATGCTTTGGTGCCTTCGGGAACTGTGAGACAGGTGCTGCATG<br>GCTGTCGTCAGCTCGTGTTGTGAAATGTTGGGTTAAGTCCCGCAACGAGCGCAACCCTTATCCTTTGTTGCCAGCGGTCCGGCCGGGAACTCAAAGGAGACTGCCAGTGATAAACTGGAGGAAGGTGGGGAT<br>GACGTCAAGTCATCATGGCCCTTACGACCAGGGCTACACACGTGCTACAATGGCATATACAAAGAGAAGCGACCTCGCGAGAGCAAGCGGACCTCATAAAGTATGTCGTAGTCCGGATTGGAGTCTGCAACTC<br>GACTCCATGAAGTCGGAATCGCTAGTAATCGTAGATCAGAATGCTACGGTGAATACGTTCCCGGGCCTTGTACACACCGCCCGTCACACCATGGGAGTGGGTTGCAAAAGAAGTAGGTAGCTTAACCTTCGGG<br>AGGGCGCTTACCACTTTGTGATTCATGACTGGGGTGAAGTCGTAACAAGGTAGCCG |
| SEQ ID NO: 14 |
| GAGAGTTTGATCCTGGCTCAGATTGAACGCTGGCGGCGTGCTTAACACATGCAAGTCGTACGCGAAAGGGACTTCGGTCCCGAGTAAAGTGGCGCACGGGTGAGTAACACGTGGATAATCTGCCTCTATGAT<br>GGGGATAACAGTTGGAAACGACTGCTAATACCGAATATGCTCATGATGAACTTTATGAGGAAAGGTGGCCTCTGCTTGCAAGCTATCGCATAGAGATGAGTCCGCGTCCCATTAGCTAGTTGGTGGGGTAACGG<br>CCTACCAAGGCAACGATGGGTAGCCGATCTGAGAGGATGATCGGCCACACTGGAACTGAAACACGGTCCAGACTCCTACGGGAGGCAGCAGTGGGGAATATTGCGCAATGGGCGAAAGCCTGACGCAGCG<br>ACGCCGCGTGAGGGATGAAGGTCTTCGGATCGTAAACCTCTGTCAGAAGGGAAGAAACTAGGGTGCTCTAATCATCATCCTACTGACGGTACCTTCAAAGGAAGCACCGGCTAACTCCGTGCCAGCAGCCGC<br>GGTAATACGGAGGGTGCAAGCGTTAATCGGAATTCACTGGGCGTAAAGCGCACGTAGGCTGTTATGTAAGTCAGGGGTGAAATCCCACGGCTCAACGTGGAACTGCCCTTGATACTGCACGACTTGAATCCG<br>GGAGAGGGTGGCGGAATTCCAGGTGTAGGAGTGAAATCCGTAGATATCTGGAGGAACATCAGTGGCGAAGGCGGCCACCTGGACCGGTATTGACGCTGAGGTGCGAAAGCGTGGGGAGCAAACAGGATTA<br>GATACCCTGGTAGTCCACGCCGTAAACGATGGATGCTGGATGTCGGGATGTATGTCTCGGTGTCGTAGTTAACGCGTTAAGCATCCCGCCTGGGGAGTACGGTCGCAAGGCTGAAACTCAAAGAAATTGACGG<br>GGGCCCGCACAAGCGGTGGAGTATGTGGTTTAATTCGATGCAACGCGAAGAACCTTACCTAGGTTTGACATCTGGGGAACCCTCCCGAAAAGGAGGGGTGCCCTTCGGGGAGCCCCAAGACAGGTGCTGCA<br>TGGCTGTCGTCAGCTCGTGTCGTGAGATGTTGGGTTAAGTCCCGCAACGAGCGCAACCCCTATGCATAGTTGCCAGCAAGTGATGTTGGGCACTCTATGCAGACTGCCCGGGTTAACCGGGAGGAAGGTGGG<br>GACGACGTCAAGTCATCATGGCCCTTACACCTAGGGCTACACACGTACTACAATGGCACGCACAAAGGGCAGCGATACCGTGAGGTGGAGCCAATCCCAAAAAACGTGTCCCAGTCCGGATTGCAGTCTGCA<br>ACTCGACTGCATGAAGTCGGAATCGCTAGTAATTCGAGGTCAGCATACTCGGGTGAATGCGTTCCCGGGCCTTGTACACACCGCCCGTCACACCACGAAAGTCGGTTTTACCCGAAGCCGGTGAGCCAACTAG<br>CAATAGAGGCAGCCGTCTACGGTAGGGCCGATGATTGGGGTGAAGTCGTAACAAGGTAACCG |
| SEQ ID NO: 15 |
| AGAGTTTGATCCTGGCTCAGGATGAACGCTGGCGGCGTGCTTAACACATGCAAGTCGAACGAAGCATTTAGGATTGAAGTTTTCGGATGGATTTCCTATATGACTGAGTGGCGGACGGGTGAGTAACGCGTG<br>GGGAACCTACCCTATACAGGGGGATAACAGCTGGAAACGGCTGCTAATACCGCATAAGCGCACAGAATCGCATGATTCAGTGTGAAAAGCCCTGGCAGTATAGGATGGTCCGCGTCTGATTAGCTGGTTGGT<br>GAGGTAACGGCTCACCAAGGCGACGATCAGTAGCCGGCTTGAGAGAGTGAACGGCCACATTGGGACTGAGACACGGCCCAAACTCCTACGGGAGGCAGCAGTGGGGAATATTGCACAATGGGGGAAACC<br>CTGATGCAGCGGCGCCGCGTGAGTGAAGAAGTATTTCGGTATGTAAAGCTCTATCAGCAGGGAAGAAAACAGACGGTACCTGACTAAGAAGCCCCGGCTAACTACGTGCCAGCAGCCGCGGTAATACGTAGG<br>GGGCAAGCGTTATCCGGAATTACTGGGTGTAAAGGGTGCGTAGGTGGCATGGTAAGTCAGAAGTGAAAGCCCGGGGCTTAACCCCGGGACTGCTTTTGAAACTGTCATGCTGGAGTGCAGGAGAGGTAAGC<br>GGAATTCCTAGTGTAGCGGTGAAATGCGTAGATATTAGGAGGAACACCAGTGGCGAAGGCGGCTTACTGGACTGTCACTGACACTGATGCACGAAAGCGTGGGGAGCAAACAGGATTAGATACCCTGGTAGT<br>CCACGCCCTAAACGATGAATACTAGGTGTCGGGGCCGTAGAGGCTTCGGTGCCGCAGCAAACGCAGTAAGTATTCCACCTGGGGAGTACGTTCGCAAGAATGAAACTCAAAGGAATTGACGGGGACCCGCA<br>CAAGCGGTGGAGCATGTGGTTTAATTCGAAGCAACGCGAAGAACCTTACCTGGTCTTGACATCCCAATGACCGAACCTTAACCGGTTTTTCTTTCGAGACATTGGAGACAGGTGGTGCATGGTTGTCGTCAG<br>CTCGTGTCGTGAGATGTTGGGTTAAGTCCGCAACGAGCGCAACCCCTATCTTTAGTAGCCCGCATTACGGATGGGCACTCTAGAGAGACTGCCAGGGATAACCTGGAGGAAGGTGGGGACGTCAAATC<br>ATCATGCCCCTTATGGCCAGGGCTACACACGTGCTACAATGGCGTAAACAAAGGGAAGCGAAGTCGTGAGGCGAAGCAAATCCCAGAAATAACGTCTCAGTTCGGATTGTAGTCTGCAACTCGACTACATGAA<br>GCTGGAATCGCTAGTAATCGTGAATCAGAATGTCACGGTGAATACGTTCCCGGGTCTTGTACACACCGCCCGTCACACCATGGGAGTCAGTAACGCCCGAAGTCAGTGACCCAACCGCAAGGAGGGAGCTGC<br>CGAAGGTGGGACCGATAACTGGGGTGAAGTCGTAACAAGGTAGCC |
| SEQ ID NO: 16 |
| AGAGTTTGATCCTGGCTCAGATTGAACGCTGGCGGCAGGCTTAACACATGCAAGTCGAACGGTAACAGGAAGAAGCTTGCTTCTTGCTGACGAGTGGCGGACGGGTGAGTAATGCTTGGGAATCTGGCTTA<br>TGGAGGGGGATAACTACGGGAAACTGTAGCTAATACCGCGTAATATCGAGAGATTAAAGGGTGGGACCGCAAGGCCACCTGCCATGAGATGAGCCCAAGTGGGATTAGGTAGTTGGTGAGGTAAAGGCTCA<br>CCAAGCCGACGATCTCTAGCTGGTCTGAGAGGATGACCAGCCACACTGGAACTGAGACACGGTCCAGACTCCTACGGGAGGCAGCAGTGGGGAATATTGCACAATGGGGGGAACCCTGATGCAGCCATGCC<br>GCGTGAATGAAGAAGGCCTTCGGGTTGTAAAGTTCTTTCGGTAGCGAGGAAGGCATTTAGTTTAATAGACTAGATGATTTGACGTTAACTACGAAGAAGCACCGGCTAACTCCGTGCCAGCAGCCGCGGTAAT<br>ACGGGGGGTGCGAGCGTTAATCGGAATAACTGGGCGTAAAGGGCACGCAGGCGGTGACTTAAGTGAGATGTGAAAGCCCCGGGCTTCACCTGGGAATTGCATTTCATACTGGGTCGCTAGAGTACTTTAGG<br>GAGGGGTAGAATTCCACGTGTAGCGGTGAAATGCGTAGAGATGTGGAGGAATACCGAAGGCGAAGGCAGCCCCTTGGGAATGTACTGACGCTCATGTGCGAAAGCGTGGGGAGCAAACAGGATTAGATACC<br>CTGGTAGTCCACGCTGTAAACGATGTCGATTTGGGGGTTGGGCTTTAAGCTTGGCGCCCGTAAGTCAACGTGATAAATCGACCGCCTGGGGAGTACGGCCGCAAGGTTAAAACTCAAATGAATTGACGGGGGC<br>CCGCACAAGCGGTGGAGCATGTGGTTTAATTCGATGCAACGCGAAGAACCTTACCTACTCTTGACATCCAGAGAACTTTTCAGAGATGGATTGGTGCCTTCGGGAACTCTGAGACAGGTGCTGCATGGCTGTC<br>GTCAGCTCGTGTTGTGAAATGTTGGGTTAAGTCCCGCAACGAGCGCAACCCTTATCCTTTGTTGCCAGCGATTAGGTCGGGAACTCAAAGGAGACTGCCGGTGATAAACCGGAGGAAGGTGGGGATGACGTC<br>AAGTCATCATGGCCCTTACGAGTAGGGCTACACACGTGCTACAATGGCGTATACAGAGGGAAGCAATCCTGCGAGGGGGAGCAAATCTCACAAAGTACGTCTAAGTCCGGATTGGAGTCTGCAACTCGACTCC<br>ATGAAGTCGGAATCGCTAGTAATCGCAAATCAGAATGTTGCGGTGAATACGTTCCCGGGCCTTGTACACACCGCCCGTCACACCATGGGAGTGGGTTGTACCAGAAGTAGATAGCTTAACCTTCGGGGGGGCG<br>TTTACCACGGTATGATTCATGACTGGGGTGAAGTCGTAACAAGGTAGCC |
| SEQ ID NO: 17 |
| GAGAGTTTGATCCTGGCTCAGATTGAACGCTGGCGGCATGCTTTACACATGCAAGTCGAACGGCAGCACAGGGAGCTTGCTCCCGGGTGGCGAGTGGCGCACGGGTGAGTAATACATCGGAACGTGTCCTG<br>TTGTGGGGGATAACTGCTCGAAAGGGTGGCTAATACCGCATGAGACCTGAGGGTGAAAGCGGGGGATCGCAAGACCTCGCGCAATTGGAGCGGCCGATGCCCGATTAGCTAGTTGGTGAGGTAAAGGCTCA<br>CCAAGGCGACGATCGGTAGCTGGTCTGAGAGGACGACCAGCCACACTGGGACTGAGACACGGCCCAGACTCCTACGGGAGGCAGCAGTGGGGAATTTTGGACAATGGGGGCAACCCTGATCCAGCCATGC<br>CGCGTGCAGGATGAAGGCCTTCGGGTTGTAAACTGCTTTTGTCAGGGACGAAAAGGATCGTGATAATACCATGGTCTGCTGACGGTACCTGAAGAATAAGCACCGGCTAACTACGTGCCAGCAGCCGCGGTAA<br>TACGTAGGGTGCAAGCGTTAATCGGAATTACTGGGCGTAAAGCGTGCGCAGGCGGTTCTGTAAGACAGATGTGAAATCCCCGGGCTCAACCTGGGAATTGCATTTGTGACTGCAGGACTAGAGTTCATCAGA<br>GGGGGGTGGAATTCCAAGTGTAGCAGTGAAATGCGTAGATATTTGGAAGAACACCAATGGCGAAGGCAGCCCCCTGGGATGCGACTGACGCTCATGCACGAAAGCGTGGGGAGCAAACAGGATTAGATACC<br>CTGGTAGTCCACGCCCTAAACGATGTCTACTGGTTGTTGGGGTTTATTAACCTTGGTAACGAAGCTAACGCGTGAAGTAGACCGCCTGGGGAGTACGGTCGCAAGATTAAAACTCAAAGGAATTGACGGGGAC<br>CCGCACAAGCGGTGAATGATGTGGATTAATTCGATGCAACGCGAAAAACCTTACCTAGCCTTGACATGCCAGGAATCCTGAAGAGATTCGGGAGTGCCCGCAAGGGAATCTGGACACAGGTGCTGCATGGCT<br>GTCGTCAGCTCGTGTCGTGAGATGTTGGGTTAAGTCCCGCAACGAGCGCAACCCTTGTCACTAGTTGCTACGCAAGAGCACTCTAGTGAGACTGCCGGTGACAAACCGGAGGAAGGTGGGGATGACGTCAA<br>GTCCTCATGGCCCTTATGCGTAGGGCCTCACACGTCATCAATGGTCGGAACAGAGGGCAGCGAAGCCGCGAGGTGGAGCAAATCCCAGAAAACCGATCGTAGTCCGGATTGCAGTCTGCAACTCGACTGCA<br>TGAAGTCGGAATCGCTAGTAATCGCGGATCAGCATGCCGCGGTGAATACGTTCCCGGGTCTTGTACACACCGCCCGTCACACCATGGGAGTGGGGTTCACCAGAAGACGTTTGTTTAACCGCAAGGAGGACG<br>GCGTCCACGGTGGGCTTCATGACTGGGGTGAAGTCGTAACAAGGTAGCCG |

Figure 14 (continued)

| Sequence |
|---|
| SEQ ID NO: 18 |
| TAGAGTTTGATCCTGGCTCAGGACGAACGCTGGCGGCGTGCCTAATACATGCAAGTCGAGCGAGCTTGCCTAGATGAATTTGGTGCTTGCACCAAATGAAACTAGATACAAGCGAGCGGCGGACGGGTGAGT AACACGTGGGTAACCTGCCCAAGAGACTGGGATAACACCTGGAAACAGATGCTAATACCGGATAACAACACTGACGCATGTCTAGAGTTTAAAAGATGGTTCTGCTATCACTCTTGGATGGACCTGCGGTGCA TTAGCTAGTTGGTAAGGTAACGGCTTACCAAGGCAATGATGCATAGCCGAGTTGAGAGACTGATCGGCCACATTGGGACTGAGACACGGCCCAAACTCCTACGGGAGGCAGCAGTAGGGAATCTTCCACAAT GGACGCAAGTCTGATGGAGCAACGCCGCGTGAGTGAAGAAGGGTTTCGGCTCGTAAAGCTCTGTTGGTAGTGAAGAAAGATAGAGGTAGTAACTGGCCTTTATTTGACGGTAATTACTTAGAAAGTCACGGC TAACTACGTGCCAGCAGCCGCGGTAATACGTAGGTGGCAAGCGTTGTCCGGATTTATTGGGCGTAAAGCGAGTGCAGGCGGTTCAATAAGTCTGATGTGAAAGCCTTCGGCTCAACCGGAGAATTGCATCAG AAACTGTTGAACTTGAGTGCAGAAGAGGAGAGTGGAACTCCATGTGTAGCGGTGGAATGCGTAGATATATGGAAGAACACCAGTGGCGAAGGCGGCTCTCTGGTCTGCAACTGACGCTGAGGCTCGAAAGC ATGGGTAGCGAACAGGATTAGATACCCTGGTAGTCCATGCCGTAAACGATGAGTGCTAAGTGTTGGGAGGTTTCCGCCTCTCAGTGCTGCAGCTAACGCATTAAGCACTCCGCCTGGGGAGTACGACCGCAAG GTTGAAACTCAAAGGAATTGACGGGGGCCCGCACAAGCGGTGGAGCATGTGGTTTAATTCGAAGCAACGCGAAGAACCTTACCAGGTCTTGACATCCAGTGCAAACCTAAGAGATTAGGAGTTCCCTTCGG GGACGCTGAAGACAGGTGGTGCATGGCTGCCGTCAGCTCGTGTCGTGAGATGTTGGGTTAAGTCCCGCAACGAGCGCAACCCTTGTCATTAGTTGCCATCATTAAGTTGGGCACTCTAATGAGACTGCCGGTGA CAAACCGGAGGAAGGTGGGGATGACGTCAAGTCATCATGCCCCTTATGACCTGGGCTACACACGTGCTACAATGGACGGTACAACGAGAAGCGAACCTGCGAAGGCAAGCGGATCTCTGAAAGCCGTTCTC AGTTCGGACTGTAGGCTGCAACTCGCCTACACGAAGCTGGAATCGCTAGTAATCGCGGATCAGCACGCCGGTGAATACGTTCCCGGGCCTTGTACACACCGCCCGTCACACCATGAGAGTCTGTAACACCC AAAGCCGGTGGGATAACCTTTATAGGAGTCAGCCGTCTAAGGTAGGACAGATGATTAGGGTGAAGTCGTAACAAGGTAACC |
| SEQ ID NO: 19 |
| TGCAAGTCGAGCGGATGAGGGGTGCTTGCACTCTGATTCAGCGGCGGACGGGTGAGTAATGCCTAGGAATCTGCCCGATAGTGGGGGACAACGTTTCGAAAGGAACGCTAATACCGCATACGTCCTACGGGA GAAAGTGGGGGATCTTCGGACCTCACGCTATCGGATAAGCCTAGGTCGGATTAGCTAGTTGGTGAGGTAATGGCTCACCAAGGCGACGATCCGTAACTGGTCTGAGAGGATGATCAGTCACACTGGAACTGA GACACGGTCCAGACTCCTACGGGAGGCAGCAGTGGGGAATATTGGACAATGGGCGAAAGCCTGATCCAGCCATGCCGCGTGTGTGAAGAAGGTCTTCGGATTGTAAAGCACTTTAAGTTGGGAGGAAGGG CTGTCGGCTAATACCCTGCAGTTTTGACGTTACCAACAGAATAAGCACCGGCTAACTTCGTGCCAGCAGCCGCGGTAATACGAAGGGTGCAAGCGTTAATCGGAATTACTGGGCGTAAAGCGCGCGTAGGTGG TTCAGCAAGTTGGATGTGAAAGCCCCGGGCTCAACCTGGGAACTGCATCCAAAACTACTGAGCTAGAGTACGGTAGAGGGTGGTGGAATTTCCTGTGTAGCGGTGAAATGCGTAGATATAGGAAGGAACACC AGTGGCGAAGGCGACCACCTGGACTGATACTGACACTGAGGTGCGAAAGCGTGAGGAGCAAACAGGATTAGATACCCTGGTAGTCCACGCCGTAAACGATGTCAACTAGCTGTTGGGTTCCTTGAGAACTTA GTAGCGAAGCTAACGCGATAAGTTGACCGCCTGGGGAGTACGGCCGCAAGGTTAAAACTCAAATGAATTGACGGGGGCCCGCACAAGCGGTGGAGCATGTGGTTTAATTCGAAGCAACGCGAAGAACCTTA CCTGGCCTTGACATGCTGAGAACTTTCCAGAGATGGATTGGTGCCTTCGGGAACTCAGACACAGGTGCTGCATGGCTGTCGTCAGCTCGTGTCGTGAGATGTTGGGTTAAGTCCCGTAACGAGCGCAACCCTT GTCCTTAGTTACCAGCACGTTATGGTGGGCACTCTAAGGAGACTGCCGGTGACAAACCGGAGGAAGGTGGGGATGACGTCAAGTCATCATGCCCCTTACGGCCAGGGCTACACACGTGCTACAATGGTCGGT ACAGAGGGTTGCCAAGCCGCGAGGCGGAGCTAATCTCACAAAACCGATCGTAGTCCGGATCGCAGTCTGCAACTCGACTGCGTGAAGTCGGAATCGCTAGTAATCGtGAATCAGA |
| SEQ ID NO: 20 |
| TGCAAGTCGAACGGTAACAGGCCGCAAGGTGCTGACGAGTGGCGAACGGGTGAGTAATGCATCGGAACGTGCCCAGTCGTGCGGGATAACGAAGCGAAAGCTTTGCTAATACCGCATACGATCTCAGGATG AAAGCAGGGGACCGCAAGGCCTTGCGCTCACGGAGCGGCCGATGGCAGATTAGGTAGTTGGTGGGATAAAAGCTTACCAAGCCGACGATCTGTAGCTGGTCTGAGAGGACGACCAGCCACACTGGGACCG AGACACGGCCCAGACTCCTACGGGAGGCAGCAGTGGGGAATTTTGGACAATGGGCGCAAGCCTGATCCAGCCATGCCGCGTGCAGGATGAAGGCCTTCGGGTTGTAAACTGCTTTTGTACGGAACGAAAA GACTCTGGTTAATACCTGGGGTCCATGACGTACCGTAAGAATAAGCACCGGCTAACTACGTGCCAGCAGCCGCGGTAATACGTAGGGTGCGAGCGTTAATCGGAATTACTGGGCGTAAAGCGTGCGCAGGC GGTTATGTAAGACAGATGTGAAATCCCCGGGCTCAACCTGGGAACTGCATTTGTGACTGCATAGCTAGAGTACGGCAGAGGGGGATGGAATTCCGCGTGTAGCAGTGAAATGCGTAGATATGCGGAGGAACA CCGATGGCGAAGGCAATCCCCTGGGCCTGTACTGACGCTCATGCACGAAAGCGTGGGGAGCAAACAGGATTAGATACCCTGGTAGTCCACGCCCTAAACGATGTCAACTGGTTGTTGGGTCTTCACTGACCCA GTAACGAAGCTAACGCGTGAAGTTGACCGCCTGGGGAGTACGGCCGCAAGGTTGAAACTCAAAGGAATTGACGGGGACCCGCACAAGCGGTGGATGATGTGGTTTAATTCGATGCAACGCGAAAAACCTTA CCCACCTTTGACATGTACGGAATCCTTTAGAGATAGAGGAGTGCTCGAAAGAGAGCCGTAACACAGGTGCTGCATGGCTGTCGTCAGCTCGTGTCGTGAGATGTTGGGTTAGGTCCCGCAACGAGCGCAACC CTTGTCATTAGTTGCTACATTCAGTTGGGCACTCTAATGAGACTGCCGGTGACAAACCGGAGGAAGGTGGGGATGACGTCAAGTCCTCATGGCCCTTATAGGTGGGGCTACACACGTCATACAATGGCTGGTA CAGAGGGCTGCCAACCCGCGAGGGGGAGCCAATCCCATAAAGCCAGTCGTAGTCCGGATCGCAGTCTGCAACTCGACTGCGTGAAGTCGGAATCGCTAGTAATCGCGGATCAGA |
| SEQ ID NO: 21 |
| CATGCaAGTCGAACGGCAGCGGGGGCTTCGGCCTGCCGGCGAGTGGCGAACGGGTGAGTAATGCATCGGAACGTGCCCATGTCGTGGGGGATAACGTAGCGAAAGCTACGCTAATACCGCATACGCCCTGA GGGGGAAAGCGGGGGATTCTTCGGAACCTCGCGCGATTGGAGCGGCCGATGTCGGATTAGCTAGTAGGTGAGGTAAAGGCTCACCTAGGCGACGATCCGTAGCGGGTCTGAGAGGATGATCCGCCACACTG GGACTGAGACACGGCCCAGACTCCTACGGGAGGCAGCAGTGGGGAATTTTGGACAATGGGCGCAAGCCTGATCCAGCCATGCCGCGTGAGTGAAGAAGGCCTTCGGGTTGTAAAGCTCTTTCGGCCGGGA AGAAATCGTGGTCTCTAACATAGGCCATGGATGACGGTACCGGAATAAGCACCGGCTAACTACGTGCCAGCAGCCGCGGTAATACGTAGGGTGCGAGCGTTAATCGGAATTACTGGGCGTAAAGCGTGC GCAGGCGGTTTTGTAAGACAGATGTGAAATCCCCGGGCTTAACCTGGGAACTGCGTTTGTGACTGCAAGGCTAGAGTACGGCAGAGGGGGGGTGGAATTCCTGGTGTAGCAGTGAAATGCGTAGAGATCAGG AGGAACACCGATGGCGAAGGCAGCCCCCTGGGCCTGTACTGACGCTCATGCACGAAAGCGTGGGGAGCAAACAGGATTAGATACCCTGGTAGTCCACGCCCTAAACGATGTCGACTAGTCGTTCGGAGCAG CAATGCACTGAGTGACGCAGCTAACGCGTGAAGTCGACCGCCTGGGGAGTACGGTCGCAAGGTTAAAACTCAAAGGAATTGACGGGGACCCGCACAAGCGGTGGATGATGTGGATTAATTCGATGCAACGC GAAAAACCTTACCTACCCTTGACATGTCTGGAACCTTGCTGAGAGGCGAGGGTGCCTTCGGGAGCCAGAACACAGGTGCTGCATGGCTGTCGTCAGCTCGTGTCGTGAGATGTTGGGTTAAGTCCCGCAACG AGCGCAACCCTTGTCACTAGTTGCCATCATTTGGTTGGGCACTCTAGTGAGACTGCCGGTGACAAACCGGAGGAAGGTGGGGATGACGTCAAGTCCTCATGGCCCTTATGGGTAGGGCTTCACACGTCATACA ATGGTCGGTACAGAGGGTTGCCAAGCCGCGAGGTGGAGCCAATCCCTTAAAGCCGATCGTAGTCCGGATCGTAGTCTGCAACTCGACTACGTGAAGTCGGAATCGCTAGTAATCGCAGATCAGC |
| SEQ ID NO: 22 |
| AAATTGAAGAGTTTGATCATGGCTCAGATTGAACGCTGGCGGCAGGCCTAACACATGCAAGTCGAACGGTAACAGGAAGAAGCTTGCTTCTTTGCTGACGAGTGGCGGACGGGTGAGTAATGTCTGGGAAA CTGCCTGATGGAGAGGGATAACTACTGGAAACGGTAGCTAATACCGCATAACGTCGCAAGACCAAAGAGGGGGACCTTCGGGCCTCTTGCCATCGGATGTGCCCAGATGGGATTAGCTAGTAGGTGGGGTAA CGGCTCACCTAGGCGACGATCCCTAGCTGGTCTGAGAGGATGACCAGCCACACTGGAACTGAGACACGGTCCAGACTCCTACGGGAGGCAGCAGTGGGGAATATTGCACAATGGGCGCAAGCCTGATGCAG CCATGCCGCGTGTATGAAGAAGGCCTTCGGGTTGTAAAGTACTTTCAGCGGGGAGGAAGGGAGTAAAGTTAATACCTTTGCTCATTGACGTTACCCGCAGAAGAAGCACCGGCTAACTCCGTGCCAGCAGCC GCGGTAATACGGAGGGTGCAAGCGTTAATCGGAATTACTGGGCGTAAAGCGCACGCAGGCGGTTTGTTAAGTCAGATGTGAAATCCCCGGGCTCAACCTGGGAACTGCATCTGATACTGGCAAGCTTGAGTC TCGTAGAGGGGGGTAGAATTCCAGGTGTAGCGGTGAAATGCGTAGAGATCTGGAGGAATACCGGTGGCGAAGGCGGCCCCCTGGACGAAGACTGACGCTCAGGTGCGAAAGCGTGGGGAGCAAACAGGA TTAGATACCCTGGTAGTCCACGCCGTAAACGATGTCGACTTGGAGGTTGTGCCCTTGAGGCGTGGCTTCGGAGCTAACGCGTTAAGTCGACCGCCTGGGGAGTACGGCCGCAAGGTTAAAACTCAAATGAAT TGACGGGGGCCCGCACAAGCGGTGGAGCATGTGGTTTAATTCGATGCAACGCGAAGAACCTTACCTGGTCTTGACATCCACAGAACTTTCCAGAGATGGATTGGTGCCTTCGGGAACTGTGAGACAGGTGCT GCATGGCTGTCGTCAGCTCGTGTTGTGAAATGTTGGGTTAAGTCCCGCAACGAGCGCAACCCTTATCCTTTGTTGCCAGCGGTCCGGCCGGGAACTCAAAGGAGACTGCCAGTGATAAACTGGAGGAAGGTG GGGATGACGTCAAGTCATCATGGCCCTTACGACCAGGGCTACACACGTGCTACAATGGCGCATACAAGAGAAGCGACCTCGCGAGAGCAAGCGGACCTCATAAAGTGCGTCGTAGTCCGGATTGGAGTCTG CAACTCGACTCCATGAAGTCGGAATCGCTAGTAATCGTGGATCAgAATGCCACGGTGAATACGTTCCCGGGCCTTGTACACACCGCCCGTCACACCATGGGAGTGGGTTGCAAAAGAAGTAGGTAGCTTAACC TTCGGGAGGGCGCTTACCACTTTGTGATTCATGACTGGGGTGAAGTCGTAACAAGGTAACCGTAGGGGAACCTGCGGTTGGATCACCTCCTTA |

Figure 14 (continued)

DETERMINATION OF MICROORGANISM OPERATIONAL TAXONOMIC UNIT AND SEQUENCE-ASSISTED SEPARATION

CROSS REFERENCE

This application is a Continuation-In-Part application of PCT application PCT/CN2017/084474, filed on May 16, 2017 and claims priority to Chinese Patent Application No. 201610333530.7, titled "DETERMINATION OF MICROORGANISM OPERATIONAL TAXONOMIC UNIT AND SEQUENCE-ASSISTED SEPARATION," filed with the Patent Office of China on May 19, 2016, the entire contents of which are incorporated herein by reference in their entirety.

INCORPORATION OF SEQUENCE LISTING

The sequence listing contained in the file named HP201800195_sequence_listing.txt is 88 kilobytes (size as measured in Microsoft Windows®), was created on Oct. 30, 2018, is filed herewith by electronic submission, and is incorporated by reference.

BACKGROUND OF THE INVENTION

Assigning amplified DNA sequences, e.g. the 16S rRNA gene amplicon sequences, into operational taxonomic units (OTUs) based on sequence similarity or homology is a basic protocol in microbial community studies. OTU delineation is critical for revealing the structure of the microbial communities and identifying key species [1,2], which can guide the isolation and characterization of functionally important bacteria in downstream analyses [3,4].

OTU delineation methods when implemented as a software package, are called "pipelines." The three commonly used pipelines are QIIME[9], MOTHUR[8], and USEARCH[7]. They have shown distinct results in estimating OTU numbers with the same short-tag sequencing data generated with 454 pyrosequencing. Chen et al. showed that 10 evaluated OTU delineation methods (Mothur, Muscle+Mothur, ESPRIT, ESPRIT-Tree, SLP, Uclust, CD-HIT, DNAClust, GramCluster and CROP) commonly overestimated the number of OTUs (1708.5±1386.9) in a mock data containing 43 species. Different methods also showed divergence in a wide range: ESPRIT gave the largest estimated number of OTUs (4397), 102.3 times higher than expected, while CROP yielded the smallest number of estimated OTU (133), it was still 3.1 times of the true numbers. Bonder et al. performed denoising and chimera checking on sequences before OTU delineation methods (Qiime Blast, CD-HIT, ESPRIT-Tree, Mothur furthest, Mothur average, Uclust, Uclust ref and Uclust ref optimal), but the lowest number of OTUs (25, by CD-HIT, ESPRIT-Tree and Uclust) was still 66.6% higher than expected in mock data with 15 species[6]. Edgar et al. suggested that UPARSE could get OTUs very close to real count in a mock data with 22 species, while other methods (AmpliconNoise, Mothur and Qiime) would have 1.1±0.8, 2.1±1.7 and 103.0±36.1 times more OTUs[7]. But there still was 1 more OTU with <97% identity to mock reference from Uparse.

The overestimation of OTU numbers from the same short-tag sequencing data also exists with Illumina sequencing. When evaluated by three sub-region amplicon sequencing of mock samples, MOTHUR resulted in 2.0±0.1, 2.5±0.1 and 10.1±3.4 times of expected number of 20 species[8]. By performing OTU delineation on the forward-end reads of mock data with 22 species, QIIME got 8.4 times more OTUs (206 vs. 22), while USEARCH gave 2 spurious OTUs (identity <97% to mock reference). Furthermore, 4.3±1.3 spurious OTUs appeared when merged paired-end reads were analyzed by Usearch[7]. Thus all three commonly used pipelines, Qiime[9], Mothur[8] and Usearch[7] overestimate the number of OTUs.

OTU overestimation generates many spurious OTUs, which further distorts the composition profiles of a microbial community. It impedes the isolation and verification of functionally important bacteria in subsequent experiments. Thus it is important to find out why these pipelines generate high number of spurious OTUs, and develop a solution to this problem.

SUMMARY OF THE INVENTION

Disclosed herein is a modified approach to minimizing pseudo OTUs. In this study, we constructed 7 sets of mock communities with 22 different 16S rRNA gene clones, each varied in clone member concentrations. The amplicons of 16S rRNA gene V3V4 hyper-variable regions [10] of these communities were sequenced in three independent sequencing runs with inner- or inter-run replicates on the Illumina Miseq platform. Previous studies have revealed the error pattern of raw reads [11,12], instead we focused on the "qualified sequences" passing quality filtrations, which are directly responsible for the accuracy of OTU delineation. The three commonly used pipelines, Qiime [9], Mothur [8] and Usearch [7] were then applied and evaluated. The detailed source of each OTU was traced to figure out why these pipelines divergently overestimate the number of OTUs, and a modified approach was devised to minimize these pseudo OTUs. Additionally, four real data sets with diverse target regions (V4 or V3V4) and sequencing lengths (150 bp, 200 bp, 250 bp or 300 bp) were utilized to validate this modified approach by measuring the improvements of OTU numbers, and alpha and beta diversities.

In one embodiment, the present disclosure provides a method of defining microbial operational taxonomic units (OTUs) in a sample, the method comprising: obtaining a sample, which comprises microorganisms each of which comprises a phylogenetically information gene, obtaining raw sequence reads of the phylogenetically informative gene of the microorganisms in the sample using a PCR-based high-throughput sequencing technique, processing the raw sequence reads to obtain assembled, fully-length qualified sequences, obtaining, by a processor, a relative abundance value of each of the qualified sequences, wherein the total relative abundance of all qualified sequences is 100%; ranking, by the processor, from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 75% of the total abundance; and the low abundance group consists of the remaining qualified sequences which account for about 25% of the total abundance; delineating, by the processor, OTUs in the sample using only qualified sequences in the high abundance group to obtain Tentative OTUs; and re-mapping, by the processor, qualified sequences in the low abundance group to the Tentative OTUs, and assigning them individually to a suitable Tentative OTUs only if they the qualified sequence has at least 97% sequence similarly to the OTU Sequence, to arrive at the final definition of OTUs.

In one embodiment, the phylogenetically informative gene is selected from the group consisting of the 16s rRNA gene or the 18s rRNA gene.

In one embodiment, the phylogenetically informative gene is one or more variable regions of the 16s rRNA gene, such as the V3, V3-V4, V4, V5-V6, V9 hypervariable regions thereof.

In one embodiment, the raw sequence reads are obtained by filtering, quality-trimming, de-replicating and removing PCR primers to obtain qualified sequences.

In one embodiment, the OUT is delineated by a pipeline selected from the group consisting of VAMPS, USEARCH (such as, v4, v5, v6, v7, and v8, for example v8.1.1861), QIIME (such as v1.0, v1.1, v1.8, and v1.9, for example v1.9.1), and MOTHUR (such as v1.0, v1.1, v1.8, and v1.9, for example v1.29.0).

The DNA sequence may be determined by a pyrosequencing method using e.g. an Illumina™ Sequencer, and the total nucleic acid is isolated from the sample and then sequenced.

The present disclosure also provides a method for isolating a microorganism from an environmental sample, wherein the microorganism comprises a phylogenetically informative gene, the method comprising: determining OTUs in the environmental sample as described above; selecting an OTU with its unique phylogenetically informative gene sequence as a to-be-isolated microorganism; culturing microorganisms in the sample determining the DNA sequence of the phylogenetically informative gene of each of the cultured microorganisms; and isolating a microorganism the sequence of whose phylogenetically informative gene is homologous to the phylogenetically informative gene sequence of the to-be-isolated microorganism. Preferably, the isolated microorganism is verified using conventional microbiological, physiological or biochemical parameters. Often, an isolate the sequence of whose phylogenetically informative gene is 99% or even 95% identical or even less to the phylogenetically informative gene sequence of the to-be-isolated microorganism is satisfactory and isolated.

The embodiments of this disclosure further provide an electronic device, including at least one processor; and a memory communicably connected with the at least one processor for storing instructions executable by the at least one processor, execution of the instructions by the at least one processor causes the at least one processor to obtain a relative abundance value of each of qualified sequences of a phylogenetically informative gene in microorganisms contained in the sample, wherein the total relative abundance of all qualified sequences is 100%; rank from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance; delineate OTUs in the sample using only qualified sequences in the high abundance group to obtain Tentative OTUs; and re-map qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs. The embodiments of this disclosure further provide a non-transitory computer-readable storage medium storing executable instructions that, when executed by an electronic device, cause the electronic device to obtain a relative abundance value of each of qualified sequences of a phylogenetically informative gene in microorganisms contained in the sample, wherein the total relative abundance of all qualified sequences is 100%; rank from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance; delineate OTUs in the sample using only qualified sequences in the high abundance group to obtain Tentative OTUs; and re-map qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

BRIEF DESCRIPTION OF THE DRAWINGS

FIG. 14 shows the sequences of the various clones used in the construction of the mock communities.

DESCRIPTION OF THE INVENTION

Figure 1:
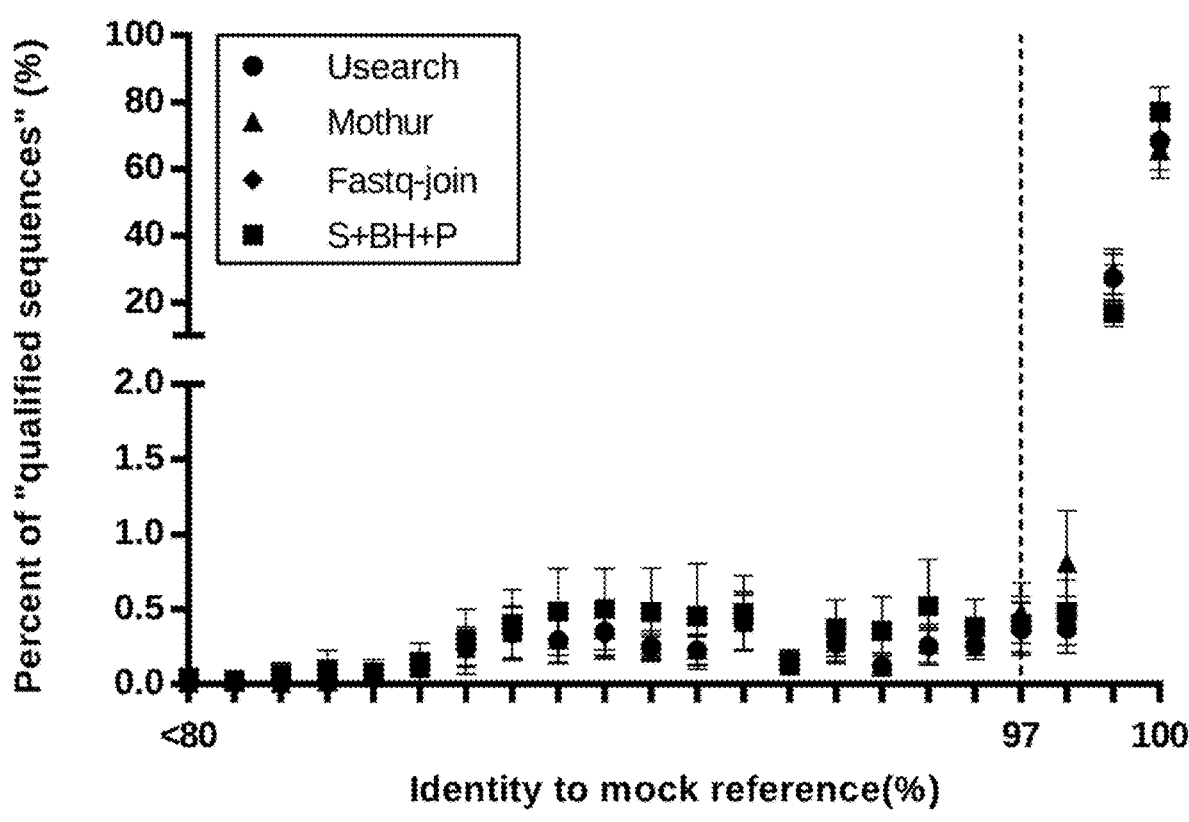
FIG. 1 shows that distributions of the "qualified sequences" obtained by four methods according to their identity levels to the closest mock references. The sequence region corresponding to PCR primers were trimmed after quality filtration. S+BH+P: quality trimming (Sickle) combined with error correction (BayesHammer) followed by read overlapping (PANDAseq).

A clear and complete description of the technical solutions in the present invention will be given below, in conjunction with the accompanying drawings in the embodiments of the present invention. Apparently, the embodiments described below are a part, but not all, of the embodiments of the present invention.

Our study showed that the three commonly used OTU delineation pipelines, Qiime, Mothur and Usearch provided divergent numbers and accuracy of OTUs in the mock data. This divergence also occurred in the real data sets, resulting in significantly discordant alpha and beta diversity information.

According to the survey of mock data, we found that this was due to sequencing errors that could not be removed through commonly used quality filtration methods. These errors were mainly distributed in unique sequences with lower abundance. Though the overall abundance of these "bad sequences" was low (ca. 5% of total "qualified sequences"), inclusion of these "bad sequences" into OTU delineation not only increased the number of pseudo OTUs by taking many of these "bad sequences" as centroids, but also distorted the abundance profiles of "real OTUs" by assigning some high-quality reads into pseudo OTUs.

The remaining errors suggest that the per-base quality scores may not be enough for the indication of the actual error rates [8,12,28]. Our study showed that "bad sequences" with >3% errors existed under the condition that only 0.5 errors per sequence were allowed in "qualified sequences" giving to their quality scores. Chimera detection methods are also widely implemented to overcome the PCR-introduced errors. But the filtration of either chimeric unique sequences before OTU delineation or chimeric OTUs afterwards could not eliminate pseudo OTUs in our study. These results indicate that the current quality control methods are not efficient enough to remove all sequences with errors >3%.

The quality filtrations do not change the error profiles in "qualified sequences" either. Substitutions rather than insertions and deletions were the major source of errors. C bases were significantly more likely to produce substitution errors than G bases, and tendencies of substitutions also occurred: A→G, C→A, G→T and T→C, similar as reported in raw reads [12].

We have demonstrated that the most abundant sequences are believed to be biologically real sequences [11], and they are surrounded by an "error cloud" composed of lower-abundance sequences, mostly singletons [7,29]. Accordingly, Nicholas et al. filtered out lower-abundance OTUs [11], but it did not improve delineation of OTUs. Removal of lower-abundance OTUs also means to abandon all the sequences assigned to them regardless of their individual accuracy. Chen et al. discarded all lower-abundance sequences in 454 sequencing data despite of their accuracy [5], but according to our results only a small part of lower-abundance sequences in Miseq data were actually "bad sequences." Edgar instead shelved singletons when making OTU delineation by Usearch, to prevent them from becoming the centroids of OTUs, and then remapped them to OTUs to achieve better coverage [7]. Our approach enlarges the extent of unique sequences to be put aside during OTU delineation, as singletons are not the only source of "bad sequences".

According to the mock data, all the "bad sequences" were observed in the lower-abundance region. Although the actual distribution of "bad sequences" was unknown in real data, we can set a threshold to determine the low-abundance unique sequences avoided from OTU delineation. To find out a universally applicable threshold, we surveyed the distribution of unique sequences and OTU delineation results in four real data sets. Although they sequenced different target regions of 16S rRNA gene with divergent sequencing protocols, all the real data sets of host-associated or free-living microbial communities consistently included a large portion of lower-abundance unique sequences. When these unique sequences were not engaged in the initial OTU delineation, the number of OTUs decreased greatly and reached plateau stage where different pipelines provided similar results. The relative abundance thresholds are suitable all the data sets when the low-abundance unique sequences occupied 25% of total "qualified sequences". Moreover, these levels of thresholds were proved to sufficient to preserve all reliable unique sequences according to bootstrap resampling. On the contrary, the signal-to-noise ratios of the lower-abundance sequences suggested that their abundances were indeed highly biased, and should not be used for further analyses.

Remapping "qualified sequences" to pre-defined OTUs afterwards is another important procedural step. This procedure separates OTU delineation to two parts: (i) choosing the centroid of each OTU and (ii) reference-based OTU assignment. Although 25% of sequences were put aside during the initial step of OTU delineation, only the ones failed to match the 97% similarity threshold were eventually discarded (<10%). It gives strict criteria on selecting centroids for OTU delineation, but still allows high-quality, lower-abundance sequences to be assigned into corresponding OTUs.

Our approach prevents the artefacts in lower-abundance unique sequences from becoming the centroids of OTUs, reducing the overestimation of number of OTUs produced by most existing methods to a reasonable level. The OTU results are more reliable and reproducible in downstream analyses and experiments, thus accelerating the detection, isolation and validation of functionally important bacteria. The choice of OTU delineation methods was no longer a problem, as all OTU delineation pipelines integrated with our approach provided a similar number of OTUs, and generated consistent alpha and beta diversities. Furthermore, the application of our approach is simple since it does not need to know the exact source of each error nor to perform additional filtrations on spurious OTUs. It also reduces the requirement of computing resources by only analyzing part of abundant unique sequences. We believe this accurate, simple, fast, and easy to be integrated approach is of potential use in microbial studies.

The present disclosure provides a method of defining microbial operational taxonomic units (OTUs) in a sample, the method comprising: 1)—obtaining a sample, which comprises microorganisms each of which comprises a phylogenetically information gene, 2)—obtaining raw sequence reads of the phylogenetically informative gene of the microorganisms in the sample using a PCR-based high-throughput sequencing technique, 3)—processing the raw sequence reads to obtain assembled, fully-length qualified sequences, 4)—obtaining a relative abundance value of each of the qualified sequences, wherein the total relative abundance of all qualified sequences is 100%; 5)—ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance; 6)—delineating OTUs in the sample using only qualified sequences in the high abundance group to obtain Tentative OTUs; and 7)—re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

In some embodiments, Steps 4), 5), 6) and/or 7) are carried out by a processor.

In some embodiments, in Step 5) the high abundance group consists of qualified sequences whose abundance values are higher than the those in the low abundance group and collectively account for about 71%-79%, 72%-78%, 73%-77%, 74-76%, 74.5%-75.5%, 74.6%-75.4%, 74.7%-75.3%, 74.8%-75.2%, 74.9%-75.1% of the total abundance; and the low abundance group consists of the remaining qualified sequences which account for about 21%-29%, 22%-28%, 23%-27%, 24-26%, 24.5%-25.5%, 24.6%-25.5%, 24.7%-25.3%, 24.8%-25.2%, 24.9%-25.1% of the total abundance.

In some embodiments, in Step 5) the high abundance group consists of qualified sequences whose abundance values are higher than the those in the low abundance group and collectively account for about 75% of the total abundance; and the low abundance group consists of the remaining qualified sequences which account for about 25% of the total abundance.

In some embodiments, in Step 7) assigning them individually to a suitable Tentative OTUs only if they the qualified sequence has at least 91%, 92%, 93%, 94%, 95%, 96%, 97%, 98%, or 99% sequence similarly to the OTU Sequence.

Accordingly, in one embodiment, the present disclosure provides a method of defining microbial operational taxonomic units (OTUs) in a sample, the method comprising:
  obtaining a sample, which comprises microorganisms each of which comprises a phylogenetically information gene,
  obtaining raw sequence reads of the phylogenetic ally informative gene of the microorganisms in the sample using a PCR-based high-throughput sequencing technique,
  processing the raw sequence reads to obtain assembled, fully-length qualified sequences,
  obtaining, by a processor, a relative abundance value of each of the qualified sequences, wherein the total relative abundance of all qualified sequences is 100%;
  ranking, by the processor, from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 75% of the total abundance; and the low abundance group consists of the remaining qualified sequences which account for about 25% of the total abundance;
  delineating, by the processor, OTUs in the sample using only qualified sequences in the high abundance group to obtain Tentative OTUs; and
  re-mapping, by the processor, qualified sequences in the low abundance group to the Tentative OTUs, and assigning them individually to a suitable Tentative OTUs only if they the qualified sequence has at least 97% sequence similarly to the OTU Sequence, to arrive at the final definition of OTUs.

A suitable sample for the method of the present disclosure may be an environmental sample, e.g. a soil, water, or atmosphere sample, or a sample from a subject, for example a clinical sample, especially a sample for the studies of gut microflora, for example a fecal sample.

An operational taxonomic unit (OTU) is a cluster of individuals intended to represent a taxonomic unit or species in nucleic acid sequence based phylogenetic studies. Each OTU represents a cluster of similar sequence variants of a phylogenetically informative gene sequence, and each OTU may represent a species or genus depending on the sequence similarity threshold.

A phylogenetically informative gene is well known to those of ordinary skills in the art of gene-based phylogenetic studies, and is a gene or a region of the organism's genome that is useful in delineating the phylogenetic relationship of two or more organisms. Specifically, a phylogenetically information gene sequence contains sufficient random mutations, the number of which are the consequence or, and proportional to, the time since the two or more organisms shared a common ancestor, to allow the elucidation of the phylogenetic relationship of the organisms. It is well known that the number of mutations (or differences) among the organisms should not be too numerous, or too few, either of which will prevent a meaningful relationship from being deciphered.

Many phylogenetically informative genes are known and widely-recognized in the art, largely through empirical determinations. Choice of phylogenetically informative genes for a particular phylogenetic study is dependent on, in addition to the mutation rate of the gene, the phylogenetic relationship of the organisms under study. Obviously, a rapidly evolving gene is suitable only for determining the relationship of closely related organisms (which are separated only recently on the evolutionary tree; while a relatively slow-to-mutate gene may be suitable for more distantly related taxa.

Examples of phylogenetically informative gene sequences include the 16s rRNA gene in prokaryotes, or the 18s rRNA gene in eukaryotes. Specifically, the various hypervariable regions of the 16s rRNA gene, e.g. V1, V2, V3 . . . V9, or the adjacent regions thereof, and the ITS (Internal transcribed spacers) or even the entire 16s rRNA gene could be used.

Typically, in 16s rRNA gene based metagenomics studies, OTU clusters are defined by a 97% identity threshold of the 16S gene sequence variants, but also the use of 99% identity is suggested for species separation.

As used in the context of this disclosure, the term "raw sequence reads" means the nucleotide sequence directly generated by the detector of an automatic sequencing machine, along with its corresponding quality scores to indicate the accuracy of the detection of each nucleotide.

Many PCR-based high-throughput or "next-gen" sequencing techniques are known in the art and are commercially available, such as various sequencing machines udner the tradenames of 454 SEQUENCER™, IONTORRENT™, ILLUMINA™ and PACBIO™.

The raw sequence reads are first assembled by paired-end sequencing (PET) protocols, with PCR primer truncated out. The assembled sequence is processed by filtering, quality-trimming, de-replicating, removing PCR primers, and then evaluated to determine if it has a desired accuracy based on either averaged quality score or expected error rate calculated by its corresponding quality scores. Assembled sequences satisfying certain predetermined criterion would be considered to be "qualified sequences," which are then binned into non-redundant unique sequences.

The length of qualified sequences depends on which region or adjacent regions are used. In general, the qualified sequence should be sufficiently long to provide meaningful sequence information and allow the determination of the entire phylogenetically informative gene sequence under study.

A "relative abundance value" of each unique sequence is then calculated, which is the abundance of a unique sequences divided by the total abundance of all the sequences. The relative abundance of unique sequences threshold generally varies from 0.0005% to 0.01% depending on the datasets.

Once the relative abundance is determined, the unique sequences are then ranked based on their relative abundance value, using a computer. The sequences are then separated into two groups, a high abundance group and a low abundance group, wherein the high abundance group consists of qualified sequences with higher abundance values the sum of which equals to about 75% of the total abundance; and the low abundance group consists of the remaining qualified sequences with lower abundance values the sum of which equals to the remaining about 25% of the total abundance. Although a 75-25% delineation is used in the examples, one of ordinary skills in the art will recognize that this line of demarcation can be adjusted depending on the distribution of the sequences, for example as long as more than 90% of total sequences can be assigned to the tentative OTUs. It is recognized that different delineating methods will result in slightly different numbers of OTUs.

In one embodiment, the present disclosure is used with the 16s rRNA genes or the 18s rRNA genes as phylogenetically informative genes, especially one or more variable regions of the rRNA genes.

In one embodiment, the present disclosure is used in association with a widely available pipeline for OTU delineation such as USEARCH, QIIME, and MOTHUR.

The present disclosure further provides a method for isolating a microorganism, from an environmental sample, based on the sequence information of the phylogenetically informative gene of the OTU, as determined above. The "sequence guided isolation" method of the present disclosure comprises: i) culturing under various appropriate conditions of all microorganisms in the sample, to obtain pure cultures of as many microorganisms as possible; and ii) the DNA sequences of the phylogenetically informative gene of the isolates are determined, and the isolate whose relevant sequence is identical or sufficiently similar to the OTU sequence is identified. If the taxonomic or other characteristics of the microorganism to be isolated is known or determinable based on the OTU information, colony morphology or other, traditional microbiological traits can and should be used to narrow the pool of potential isolates in need of sequence verification.

The present disclosure further provides a method of defining microbial operational taxonomic units (OTUs) in a sample, the method comprising:

1)—obtaining a relative abundance value of each of qualified sequences of a phylogenetically informative gene in microorganisms contained in the sample, wherein the total relative abundance of all qualified sequences is 100%;

2)—ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance;

3)—delineating OTUs in the sample using only qualified sequences in the high abundance group to obtain Tentative OTUs; and 4)—re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

In an embodiment, the qualified sequences are obtained by obtaining raw sequence reads of the phylogenetically informative gene of the microorganisms in the sample using a PCR-based high-throughput sequencing technique, and processing the raw sequence reads to obtain assembled, fully-length qualified sequences.

The present disclosure further provides a method for identifying, characterizing or assessing a microbial community or microbiota in a sample, the method comprising:

1)—obtaining a relative abundance value of each of qualified sequences of a phylogenetically informative gene in microorganisms contained in the sample, wherein the total relative abundance of all qualified sequences is 100%;

2)—ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance;

3)—delineating microbial operational taxonomic units (OTUs) in the sample using only qualified sequences in the high abundance group to obtain Tentative OTUs; and 4)—re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

The present disclosure further provides a method for identifying, characterizing or assessing health condition of a subject, the method comprising:

1)—obtaining a relative abundance value of each of qualified sequences of a phylogenetically informative gene in microorganisms in a sample from intestine of the subject, wherein the total relative abundance of all qualified sequences is 100%;

2)—ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance;

3)—delineating microbial operational taxonomic units (OTUs) in the sample using only qualified sequences in the high abundance group to obtain Tentative OTUs; and 4)—re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

The present disclosure further provides a software for defining microbial operational taxonomic units (OTUs) in a sample, the software comprising:

a first module for obtaining a relative abundance value of each of qualified sequences of a phylogenetically informative gene in microorganisms contained in the sample, wherein the total relative abundance of all qualified sequences is 100%;

a second module for ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance;

a third module for delineating OTUs in the sample using only qualified sequences in the high abundance group to obtain Tentative OTUs; and a forth module for re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

The present disclosure further provides a system for defining microbial operational taxonomic units (OTUs) in a sample, the system comprising:

a first means for obtaining a relative abundance value of each of qualified sequences of a phylogenetically informative gene in microorganisms contained in the sample, wherein the total relative abundance of all qualified sequences is 100%;

a second means for ranking from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance;

a third means for delineating OTUs in the sample using only qualified sequences in the high abundance group to obtain Tentative OTUs; and a forth means for re-mapping qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

The disclosure is illustrated by the following examples, which are not intended to be limiting in any way. As used throughout, ranges are used as shorthand for describing each and every value that is within the range. Any value within the range can be selected as the terminus of the range. It is understood that when formulations are described, they may be described in terms of their ingredients, as is common in the art, notwithstanding that these ingredients may react with one another in the actual formulation as it is made, stored and used, and such products are intended to be covered by the formulations described. In addition, all references cited herein are hereby incorporated by reference in their entireties.

EXAMPLES

Figure 14:
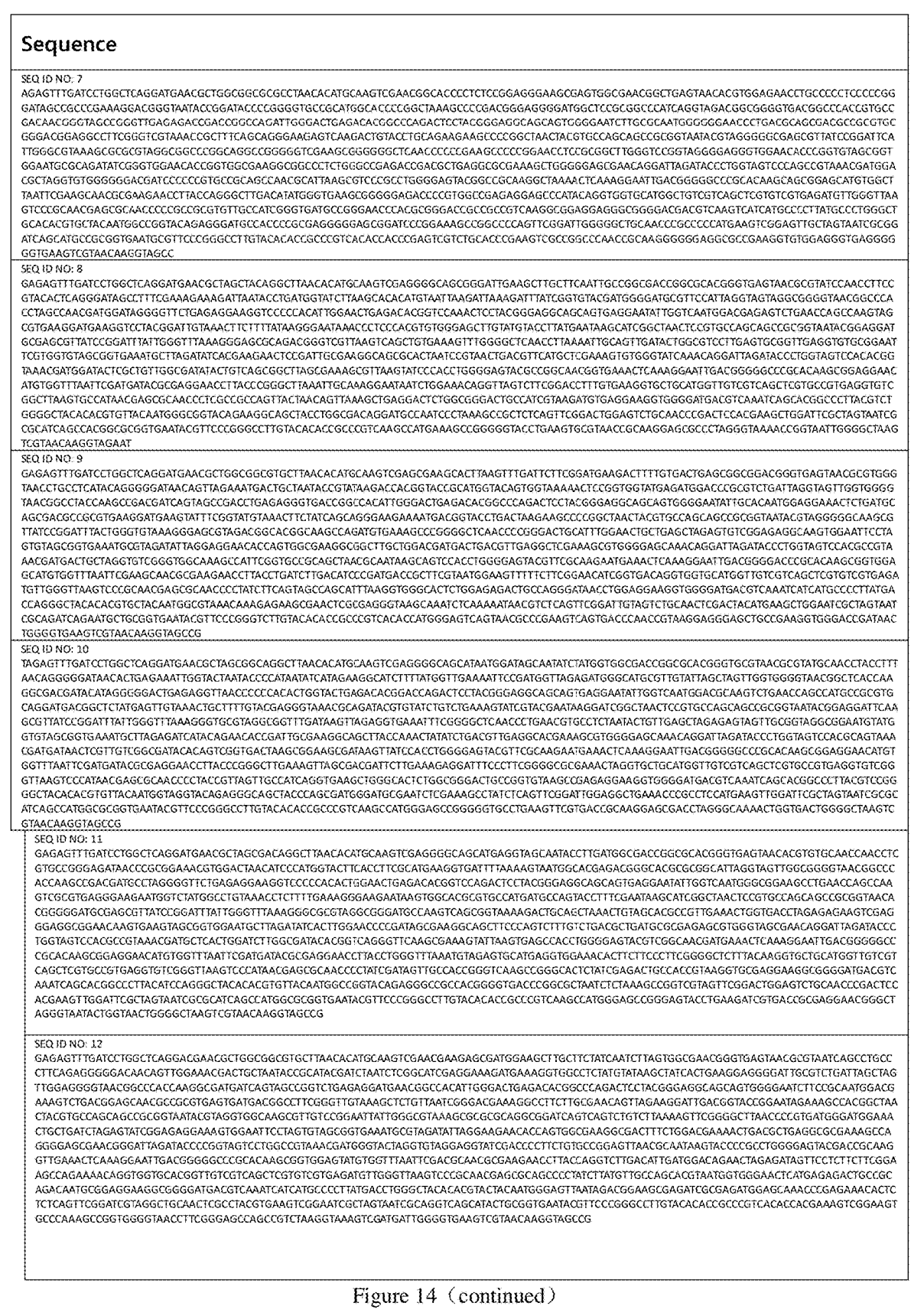

Materials and Methods
Construction of Mock Communities
A total of 22 16S rRNA gene clones were chosen to construct 7 mock communities. Table 1 shows the clone ID, taxonomy and sequence information (in conjunction with the Sequence Listing and FIG. 14) of the clones.

Each mock community has varied compositions of clones (Table. 2). These clones have ≤97% similarity to each other in V3-V4 hypervariable region in order to avoid confused estimation of OTUs. Each community had 3 replicates in the same sequencing run. 4 communities were sequenced in 2 additional runs.

Obtaining Real Data Sets

PWS data: We obtained 110 human fecal samples collected from children diagnosed with Prader-Willi syndrome or simple obesity during dietary intervention[4]. The V3-V4 hypervariable region was sequenced with mock samples by the same Illumina Miseq machine, by 2*300 bp paired-end sequencing.

Ultra data: Published data set includes microbial communities from host-associated and free-living environments, sequencing on V4 region with 150 bp single-end[30].

Water data: Published data set collected from drinking water system in the Netherlands, spanning V4 region with 2*200 bp read length [31].

TABLE 1

Sequence and Taxonomic Information for Each Clone ID

| Clone ID | Taxonomy | Sequences |
|---|---|---|
| G03.21 | Bacteria; Firmicutes; Clostridia; Clostridiales; Lachnospiraceae; *Blautia* | SEQ ID NO: 1 |
| G06.93 | Bacteria; Firmicutes; Negativicutes; Selenomonadales; Veillonellaceae; *Allisonella* | SEQ ID NO: 2 |
| D10.54 | Bacteria; "Bacteroidetes"; "Bacteroidia"; "Bacteroidales"; "Prevotellaceae"; *Paraprevotella* | SEQ ID NO: 3 |
| G02.84 | Bacteria; "Bacteroidetes"; "Bacteroidia"; "Bacteroidales"; "Porphyromonadaceae"; *Barnesiella* | SEQ ID NO: 4 |
| C09.54 | Bacteria; Firmicutes; Bacilli; Lactobacillales; Streptococcaceae; *Streptococcus* | SEQ ID NO: 5 |
| D02.70 | Bacteria; Firmicutes; Clostridia; Clostridiales; Ruminococcaceae; *Ruminococcus* | SEQ ID NO: 6 |
| D02.21 | Bacteria; "Actinobacteria"; Actinobacteria; Coriobacteriales; Coriobacteriaceae; *Collinsella* | SEQ ID NO: 7 |
| G10.33 | Bacteria; "Bacteroidetes"; "Bacteroidia"; "Bacteroidales"; Bacteroidaceae; *Bacteroides* | SEQ ID NO: 8 |
| G03.02 | Bacteria; Firmicutes; Clostridia; Clostridiales; Lachnospiraceae; *Dorea* | SEQ ID NO: 9 |
| G10.26 | Bacteria; "Bacteroidetes"; "Bacteroidia"; "Bacteroidales"; "Rikenellaceae"; *Alistipes* | SEQ ID NO: 10 |
| C10.94 | Bacteria; "Bacteroidetes"; "Bacteroidia"; "Bacteroidales"; "Porphyromonadaceae"; *Butyricimonas* | SEQ ID NO: 11 |
| F08.65 | Bacteria; Firmicutes; Negativicutes; Selenomonadales; Veillonellaceae; *Veillonella* | SEQ ID NO: 12 |
| B14.45 | Bacteria; "Proteobacteria"; Gammaproteobacteria; "Enterobacteriales"; Enterobacteriaceae; *Klebsiella* | SEQ ID NO: 13 |
| C08.06 | Bacteria; "Proteobacteria"; Deltaproteobacteria; Desulfovibrionales; Desulfovibrionaceae; *Desulfovibrio* | SEQ ID NO: 14 |
| F15.08 | Bacteria; Firmicutes; Clostridia; Clostridiales; Lachnospiraceae; *Anaerostipes* | SEQ ID NO: 15 |
| F12.59 | Bacteria; "Proteobacteria"; Gammaproteobacteria; Pasteurellales; Pasteurellaceae; *Haemophilus* | SEQ ID NO: 16 |
| G02.62 | Bacteria; "Proteobacteria"; Betaproteobacteria; Burkholderiales; Sutterellaceae; *Sutterella* | SEQ ID NO: 17 |
| B2-5 | Bacteria; Firmicutes; Bacilli; Lactobacillales; Lactobacillaceae; *Lactobacillus* | SEQ ID NO: 18 |
| YSQ.78 | Bacteria; "Proteobacteria"; Gammaproteobacteria; Pseudomonadales; Pseudomonadaceae; *Pseudomonas* | SEQ ID NO: 19 |
| YSQ.40 | Bacteria; "Proteobacteria"; Betaproteobacteria; Burkholderiales; Comamonadaceae; *Acidovorax* | SEQ ID NO: 20 |
| YSQ.182 | Bacteria; Proteobacteria"; Betaproteobacteria; Rhodocyclales; Rhodocyclaceae; *Thauera* | SEQ ID NO: 21 |
| Ecol | Bacteria; Proteobacteria; Gammaproteobacteria; Enterobacteriales; Enterobacteriaceae; *Escherichia/Shigella* | SEQ ID NO: 22 |

River data: Published data set containing the water samples along the midstream of the Danube River, applying V3-V4 region by 2*250 bp sequencing [32].

TABLE 2

Composition of Sequences (%) in Mock Communities 1-1 to 7-3

| Clone ID | 1-1 | 1-2 | 1-3 | 2-1 | 2-2 | 2-3 | 3-1 | 3-2 | 3-3 | 4-1 | 4-2 |
|---|---|---|---|---|---|---|---|---|---|---|---|
| G03.21 | 4.75 | 4.75 | 4.75 | 10.05 | 10.05 | 10.05 | 1.01 | 1.01 | 1.01 | 0.10 | 0.10 |
| G06.93 | 4.75 | 4.75 | 4.75 | 1.01 | 1.01 | 1.01 | 10.05 | 10.05 | 10.05 | 1.01 | 1.01 |
| D10.54 | 4.75 | 4.75 | 4.75 | 1.01 | 1.01 | 1.01 | 1.01 | 1.01 | 1.01 | 10.05 | 10.05 |
| G02.84 | 4.75 | 4.75 | 4.75 | 1.01 | 1.01 | 1.01 | 10.05 | 10.05 | 10.05 | 10.05 | 10.05 |
| C09.54 | 4.75 | 4.75 | 4.75 | 10.05 | 10.05 | 10.05 | 1.01 | 1.01 | 1.01 | 10.05 | 10.05 |
| D02.70 | 4.75 | 4.75 | 4.75 | 10.05 | 10.05 | 10.05 | 1.01 | 1.01 | 1.01 | 1.01 | 1.01 |
| D02.21 | 4.75 | 4.75 | 4.75 | 10.05 | 10.05 | 10.05 | 10.05 | 10.05 | 10.05 | 0.10 | 0.10 |
| G10.33 | 4.75 | 4.75 | 4.75 | 1.01 | 1.01 | 1.01 | 10.05 | 10.05 | 10.05 | 1.01 | 1.01 |
| G03.02 | 4.75 | 4.75 | 4.75 | 0.10 | 0.10 | 0.10 | 1.01 | 1.01 | 1.01 | 10.05 | 10.05 |
| G10.26 | 4.75 | 4.75 | 4.75 | 10.05 | 10.05 | 10.05 | 1.01 | 1.01 | 1.01 | 1.01 | 1.01 |
| C10.94 | 4.75 | 4.75 | 4.75 | 1.01 | 1.01 | 1.01 | 10.05 | 10.05 | 10.05 | 10.05 | 10.05 |
| F08.65 | 4.75 | 4.75 | 4.75 | 10.05 | 10.05 | 10.05 | 1.01 | 1.01 | 1.01 | 1.01 | 1.01 |
| B14.45 | 4.75 | 4.75 | 4.75 | 1.01 | 1.01 | 1.01 | 10.05 | 10.05 | 10.05 | 0.10 | 0.10 |
| C08.06 | 4.75 | 4.75 | 4.75 | 10.05 | 10.05 | 10.05 | 0.10 | 0.10 | 0.10 | 1.01 | 1.01 |
| F15.08 | 4.75 | 4.75 | 4.75 | 1.01 | 1.01 | 1.01 | 10.05 | 10.05 | 10.05 | 1.01 | 1.01 |
| F12.59 | 4.75 | 4.75 | 4.75 | 0.10 | 0.10 | 0.10 | 1.10 | 1.10 | 1.10 | 10.05 | 10.05 |
| G02.62 | 4.75 | 4.75 | 4.75 | 0.10 | 0.10 | 0.10 | 10.05 | 10.05 | 10.05 | 10.05 | 10.05 |
| B2-5 | 4.75 | 4.75 | 4.75 | 1.01 | 1.01 | 1.01 | 1.01 | 1.10 | 1.10 | 1.01 | 1.01 |
| YSQ.78 | 4.75 | 4.75 | 4.75 | 10.05 | 10.05 | 10.05 | 0.10 | 0.10 | 0.10 | 10.05 | 10.05 |
| YSQ.40 | 4.75 | 4.75 | 4.75 | 1.01 | 1.01 | 1.01 | 10.05 | 10.05 | 10.05 | 1.01 | 1.01 |
| YSQ.182 | 4.75 | 4.75 | 4.75 | 10.05 | 10.05 | 10.05 | 0.10 | 0.10 | 0.10 | 10.05 | 10.05 |
| Ecol | 0.20 | 0.20 | 0.20 | 0.20 | 0.20 | 0.20 | 0.20 | 0.20 | 0.20 | 0.20 | 0.20 |

TABLE 2-continued

Composition of Sequences (%) in Mock Communities 1-1 to 7-3

| Clone ID | 4-3 | 5-1 | 5-2 | 5-3 | 6-1 | 6-2 | 6-3 | 7-1 | 7-2 | 7-3 |
|---|---|---|---|---|---|---|---|---|---|---|
| G03.21 | 0.10 | 0.94 | 0.94 | 0.94 | 0.94 | 0.94 | 0.94 | 0.94 | 0.94 | 0.94 |
| G06.93 | 1.01 | 0.94 | 0.94 | 0.94 | 0.94 | 0.94 | 0.94 | 0.94 | 0.94 | 0.94 |
| D10.54 | 10.05 | 9.41 | 9.41 | 9.41 | 9.41 | 9.41 | 9.41 | 47.07 | 47.07 | 47.07 |
| G02.84 | 10.05 | 0.94 | 0.94 | 0.94 | 0.94 | 0.94 | 0.94 | 0.94 | 0.94 | 0.94 |
| C09.54 | 10.05 | 0.94 | 0.94 | 0.94 | 0.94 | 0.94 | 0.94 | 0.94 | 0.94 | 0.94 |
| D02.70 | 1.01 | 9.41 | 9.41 | 9.41 | 0.94 | 0.94 | 0.94 | 0.94 | 0.94 | 0.94 |
| D02.21 | 0.10 | 0.94 | 0.94 | 0.94 | 9.41 | 9.41 | 9.41 | 9.41 | 9.41 | 9.41 |
| G10.33 | 1.01 | 47.07 | 47.07 | 47.07 | 0.94 | 0.94 | 0.94 | 0.94 | 0.94 | 0.94 |
| G03.02 | 10.05 | 0.94 | 0.94 | 0.94 | 0.94 | 0.94 | 0.94 | 0.94 | 0.94 | 0.94 |
| G10.26 | 1.01 | 0.94 | 0.94 | 0.94 | 9.41 | 9.41 | 9.41 | 0.94 | 0.94 | 0.94 |
| C10.94 | 10.05 | 0.94 | 0.94 | 0.94 | 0.94 | 0.94 | 0.94 | 9.41 | 9.41 | 9.41 |
| F08.65 | 1.01 | 0.94 | 0.94 | 0.94 | 0.94 | 0.94 | 0.94 | 9.41 | 9.41 | 9.41 |
| B14.45 | 0.10 | 9.41 | 9.41 | 9.41 | 0.94 | 0.94 | 0.94 | 0.94 | 0.94 | 0.94 |
| C08.06 | 1.01 | 0.94 | 0.94 | 0.94 | 47.07 | 47.07 | 47.07 | 0.94 | 0.94 | 0.94 |
| F15.08 | 1.01 | 0.94 | 0.94 | 0.94 | 0.94 | 0.94 | 0.94 | 0.94 | 0.94 | 0.94 |
| F12.59 | 10.05 | 0.94 | 0.94 | 0.94 | 0.94 | 0.94 | 0.94 | 0.94 | 0.94 | 0.94 |
| G02.62 | 10.05 | 0.94 | 0.94 | 0.94 | 9.41 | 9.41 | 9.41 | 0.94 | 0.94 | 0.94 |
| B2-5 | 1.01 | 9.41 | 9.41 | 9.41 | 0.94 | 0.94 | 0.94 | 0.94 | 0.94 | 0.94 |
| YSQ.78 | 10.05 | 0.94 | 0.94 | 0.94 | 0.94 | 0.94 | 0.94 | 9.41 | 9.41 | 9.41 |
| YSQ.40 | 1.01 | 0.94 | 0.94 | 0.94 | 0.94 | 0.94 | 0.94 | 0.94 | 0.94 | 0.94 |
| YSQ.182 | 10.05 | 0.94 | 0.94 | 0.94 | 0.94 | 0.94 | 0.94 | 0.94 | 0.94 | 0.94 |
| Ecol | 0.20 | 0.20 | 0.20 | 0.20 | 0.20 | 0.20 | 0.20 | 0.20 | 0.20 | 0.20 |

Sequencing Procedure

Hypervariable region amplicons V3-V4 of the 16S rRNA gene were sequenced by Illumina Miseq as described in http://res.illumina.com/documents/products/appnotes/16s-metagenomic-library-prep-guide.pdf, with the following modifications. Platinum Pfx DNA polymerase (C11708021, Invitrogen, USA) was used for two steps of amplification. PCR cycles of the Amplicon PCR (amplification of 16S rRNA V3-V4 region) were reduced to 21 to diminish the PCR bias. The Index PCR and purification of PCR products were carried according to the protocol. The pair of primers used were: S-D-Bact-0341-b-S-17, 5'-CCTACGGG-NGGCWGCAG-3', and S-D-Bact-0785-a-A-21, 5'-GAC-TACHVGGGTATCTAATCC-3'[10,33].

Quality Filtration

Quality filtering was performed using Usearch [7], Mothur [13], Fastq-join [14] (implemented in Qiime [9]) and a recently described workflow [12] including quality trimming (Sickle [15]), error correction (BayesHammer [16]) and read overlapping (PANDAseq[17]) (aliased as S+BH+P). Overlaps with ≥50 bp length were required for each sequence pairs, resulting in ≥400 bp merged sequences, and no ambiguous bases were allowed. Usearch further filter out sequences with ≥0.5 expected errors. The PCR primers were truncated out from "Qualified sequences" afterwards.

OTU Delineation

Within Usearch[7] pipeline "qualified sequences" were full-length de-replicated into unique sequences, and sorted by decreasing abundance along with discarding singletons. Non-chimeric OTU representative sequences were picked afterwards by Uparse's default. Further reference-based chimera detection was performed using UCHIME[20] against RDP classifier training database[34] (v9). OTU table was finalized by mapping "qualified sequences" to the remained OTUs with Usearch[18] global alignment algorithm.

According to the developing Mothur SOP (www.mothur.org/wiki/MiSeq_SOP), "qualified sequences" were dereplicated into unique sequences, and aligned to SILVA reference database[35]. Sequences starting at or before position 6430 and ending at or after position 23439 were retained and pre-clustered with up to two differences. They were split by sample and checked for chimeras using abundant sequences as reference with UCHIME[20]. Non-chimeric sequences were classified according to Mothur-formatted version of RDP classifier training set v9[34], and non-bacterial sequences were further filtered out. OTUs were then picked by >97% similarity with average neighbor algorithm.

In Qiime pipeline "Qualified sequences" were clustered into de novo OTUs by >97% similarity using UCLUST[18]. Additional identification of chimeric OTUs was done using ChimeraSlayer[19] against Greengenes core data set[36], or UCHIME[20] against RDP classifier training database[34] (v9).

Results

Evaluation of Quality Control Processes with Mock Data

On average 15017.4±999.6 (Mean±S.D.), 16247.3±1856.4 and 34060.0±3923.9 sequences per sample were achieved from three Miseq runs, respectively. Four quality control methods were applied to perform quality filtration, including Usearch[7], Mothur[13], Fastq-join[14] and Sickle[15]+BayesHammer[16]+PANDAseq[17] (aliased as S+BH+P). After various quality filtrations and further truncation of PCR primers, the retained "qualified sequences" were aligned to mock references by Usearch global alignment[18]. Overall sequencing accuracy was presented as the identity of sequencing reads to the closest reference (FIG. 1).

As shown in FIG. 1, most "qualified sequences" after quality filtrations had adequate accuracy. Usearch, Mothur, Fastq-join and S+BH+P provided 68.5±8.9%, 65.9±8.7%, 68.9±6.1% and 77.1±7.5% of sequences 100% identical to mock references respectively. In addition, up to 94% of the "qualified sequences" shared no less than 97% identity with the closest mock reference. In addition, there were 3.4±1.6%, 3.5±1.6%, 3.3±1.5% and 5.3±3.3% of "qualified sequences" having more than 3% errors, some of which even had <90% identity to the closest mock reference.

On the other hand, for the same mock community, though the error distributions of the "qualified sequences" were similar in the four methods, the absolute quantities of the "qualified sequences" varied significantly among different sequencing runs and filtration methods (Table. 3). Fastq-join and S+BH+P were least robust that they obtained the fewest "qualified sequences".

TABLE 3

The number of sequences passed quality filtration using different methods

|  | Usearch* | Mothur* | Fastq-join* | S + BH + P*,** | Raw sequences |
|---|---|---|---|---|---|
| Run1 | 254086 | 279699 | 256981 | 262288 | 315365 |
| Run2 | 130940 | 147535 | 111966 | 148431 | 194967 |
| Run3 | 190818 | 250932 | 39329 | 138179 | 408720 |

*PCR primers were trimmed by PrimerTrim
**quality trimming (Sickle) combined with error correction (BayesHammer) followed by read overlapping (PANDAseq)

Error Pattern Profiles of the "Qualified Sequences" in Mock Data

Figure 2:
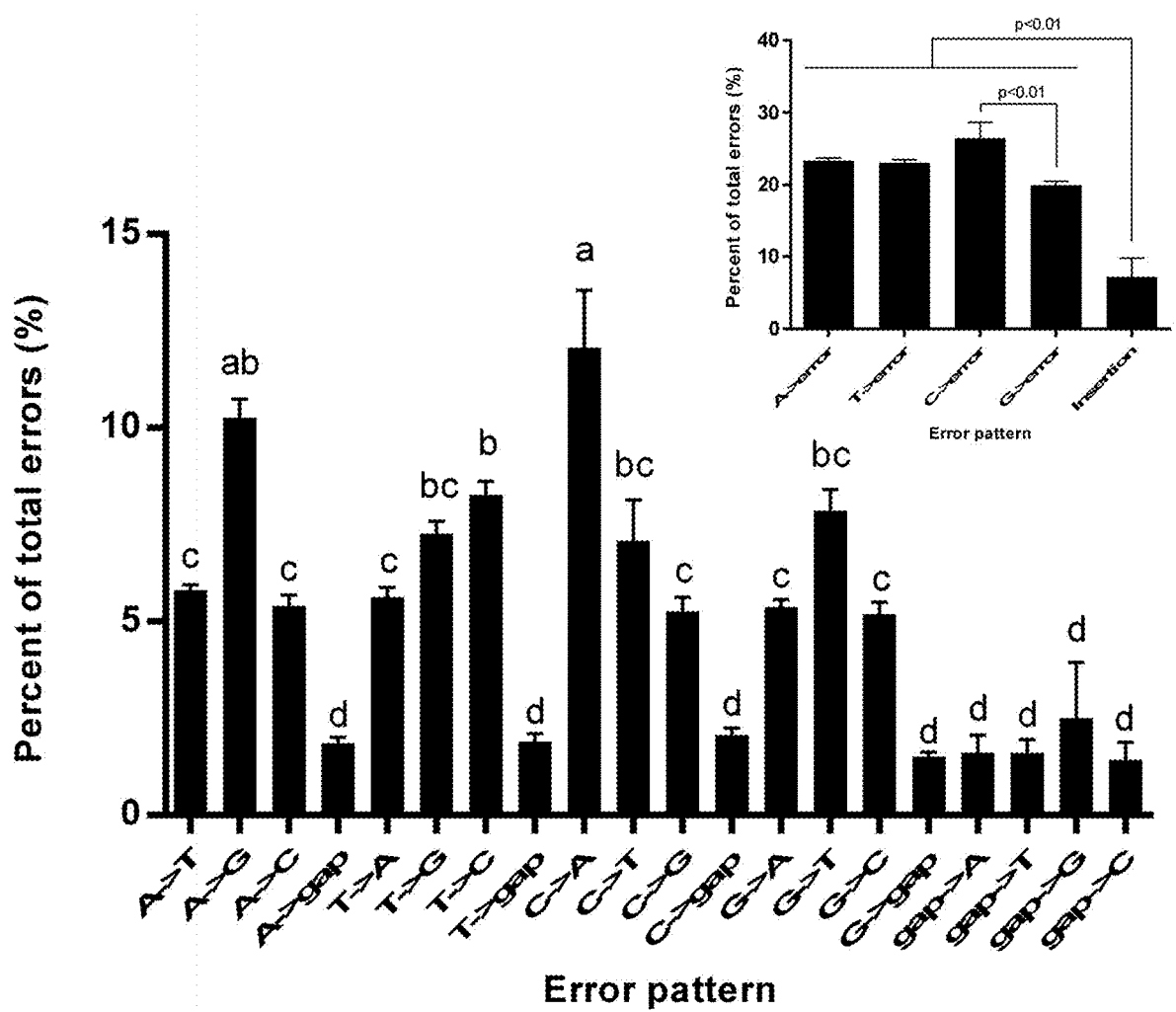
FIG. 2 shows that error pattern profiles of the "qualified sequences". Data with different superscript letters were significantly different at $P<0.01$, according to one-way ANOVA test. Inner shows the sum of proportion of each base to be misidentified, including substitutions and deletions.

On average, each "qualified sequence" contained 1.8±0.8 errors, including substitutions (bases incorrectly identified), insertions and deletions. When looking at the detailed error profiles (FIG. 2), substitutions had significantly (p<0.01) higher occurrence rate than insertions and deletions according to one-way Analysis of Variance (ANOVA) test. The four nucleotides had different error rates, with C significantly more likely to be falsely identified than G (p<0.01, one-way ANOVA test), and A and T bases in the middle. Each type of nucleotides also showed specific trend of substitution, e.g. A was more likely to be substituted by G, T by C, C by A, and G by T.

Distribution of Unique Sequences in Mock Data

The "qualified sequences" provided by Usearch or Mothur pipeline were de-replicated into 25564.7±6152.6 and 35219.3±12133.6 unique sequences respectively.

Figure 3:
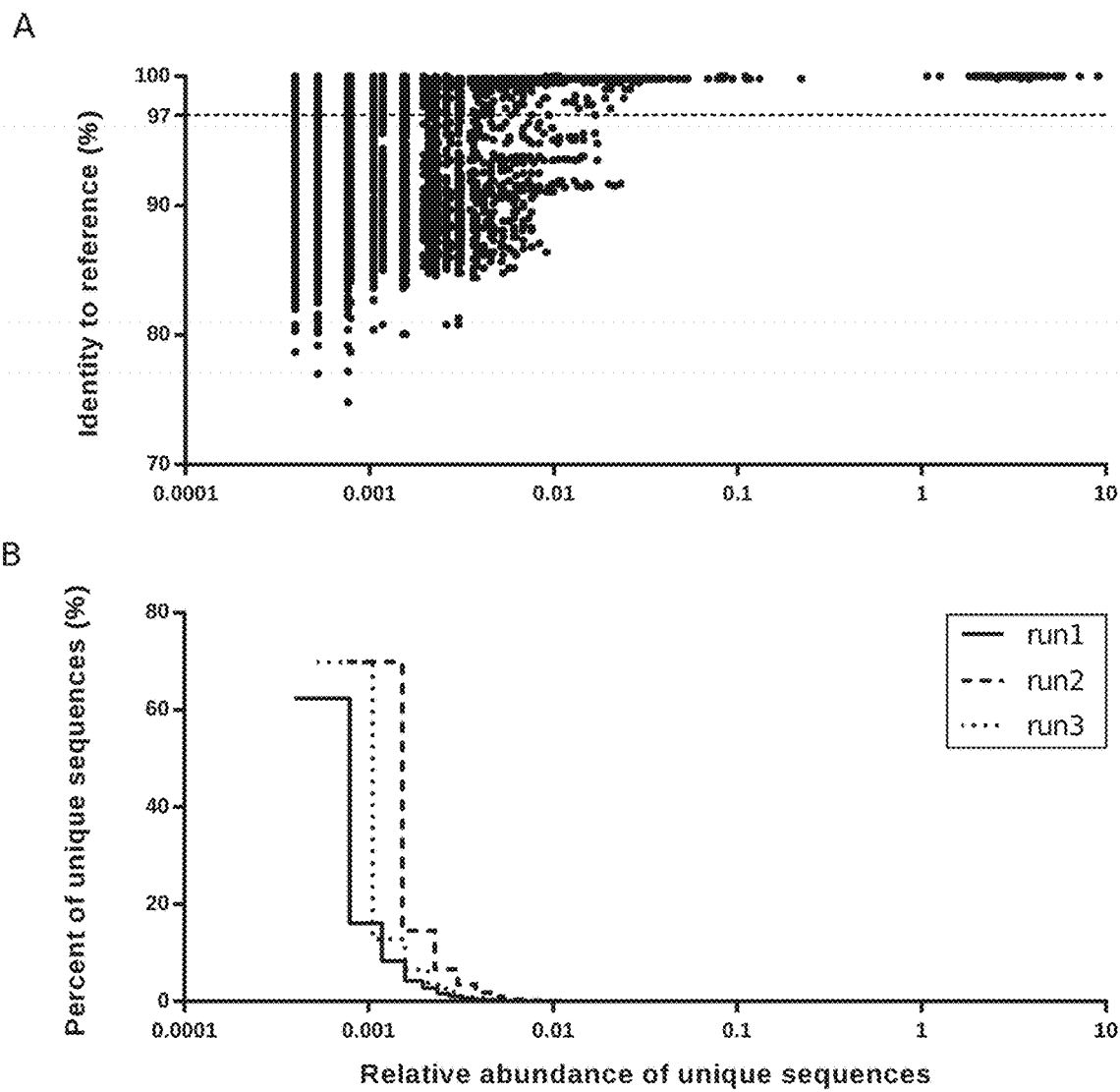
FIG. 3 shows that distribution of unique sequences in mock data. (A) Identity of unique sequences to the closest mock references. Unique sequences with >3% errors all had relative abundance <0.05%. (B) Distribution of unique sequences on their relative abundance. The majority of unique sequences had low abundance.

Take the result obtained by Usearch pipeline as an example, the abundances of the unique sequences with >3% errors were <0.05% of total "qualified sequences" (FIG. 3A). In general, for unique sequences whose relative abundance was <0.05%, the lower the relative abundance, the higher the number of different unique sequences, forming an L-shaped abundance distribution curve (FIG. 3B). With a 0.05% level of relative abundance as a threshold, the unique sequences could be separated into relatively lower- or higher-abundance regions. We found that more than 90% of unique sequences were in the lower-abundance region, but they only occupied 27.8±7.8% of total "qualified sequences".

Furthermore, almost all of the chimeric sequences detected by ChimeraSlayer[19] (5.8±1.1% of total "qualified sequences") and Uchime[20] (3.9±1.8% of total "qualified sequence") belonged to this lower-abundance region.

Figure 4:
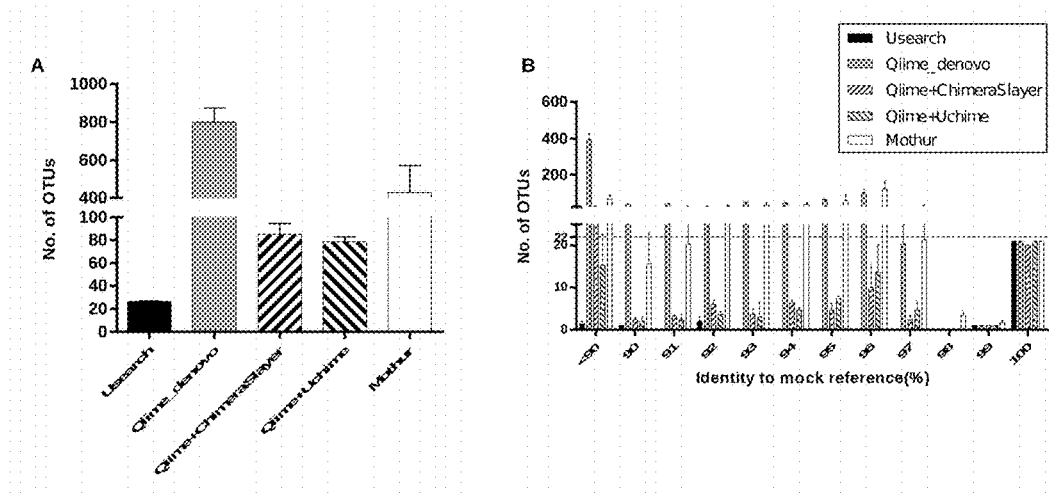
FIG. 4 shows that OTU picking accuracy and efficiency by different methods. (A) Total number of OTUs picked by each method. (B) Distribution of the picked OTUs resulted from each method according to their identity levels to the closest mock references. Additional chimera detection methods (ChimeraSlayer and Uchime) were performed on the OTUs obtained by Qiime, while Usearch and Mothur pipelines have built-in chimera detections.

OTU Delineation by Usearch, Qiime and Mothur with Default Parameters in Mock Data With default parameters set, Usearch exhibited the best resistance to the sequencing errors and assigned "qualified sequences" into 26.3±0.6 OTUs. Qiime and Mothur picked many more OTUs (799.3±74.5 and 429.0±143.0) than the actual number of 22 species (FIG. 4A). Because the previous section had shown that chimeras cannot be ignored, additional chimera detection methods (ChimeraSlayer and Uchime) were performed on the OTUs obtained by Qiime, while Usearch and Mothur pipeline implemented chimera filtering during or before OTU picking. The chimera filtration indeed improved OTU picking in Qiime that the OTU number decreased from 799.3±74.5 to 85.0±9.5 (ChimeraSlayer) and 78.7±4.2 (Uchime). The OTU numbers were still overestimated.

The accuracy of OTU delineation was evaluated by aligning representative sequences of each OTU to mock references (FIG. 4B). OTUs were defined as "perfect" (100% identical to mock references), "good" (97%≤identity<100%) and "pseudo" (identity<97%). All methods could provide 22 OTUs with >99% identity to mock references, showing one-to-one correspondence with 22 "real" species. However, Usearch, Qiime with chimera detection (ChimeraSlayer or Uchime) and Mothur also obtained 4.3±0.6 (16.4±1.8%), 61.7±10.1 (72.2±4.2%), 52.0±6.0 (66.0±4.4%) and 381.7±130.4 (88.7±2.1%) pseudo OTUs, respectively.

Figure 5:
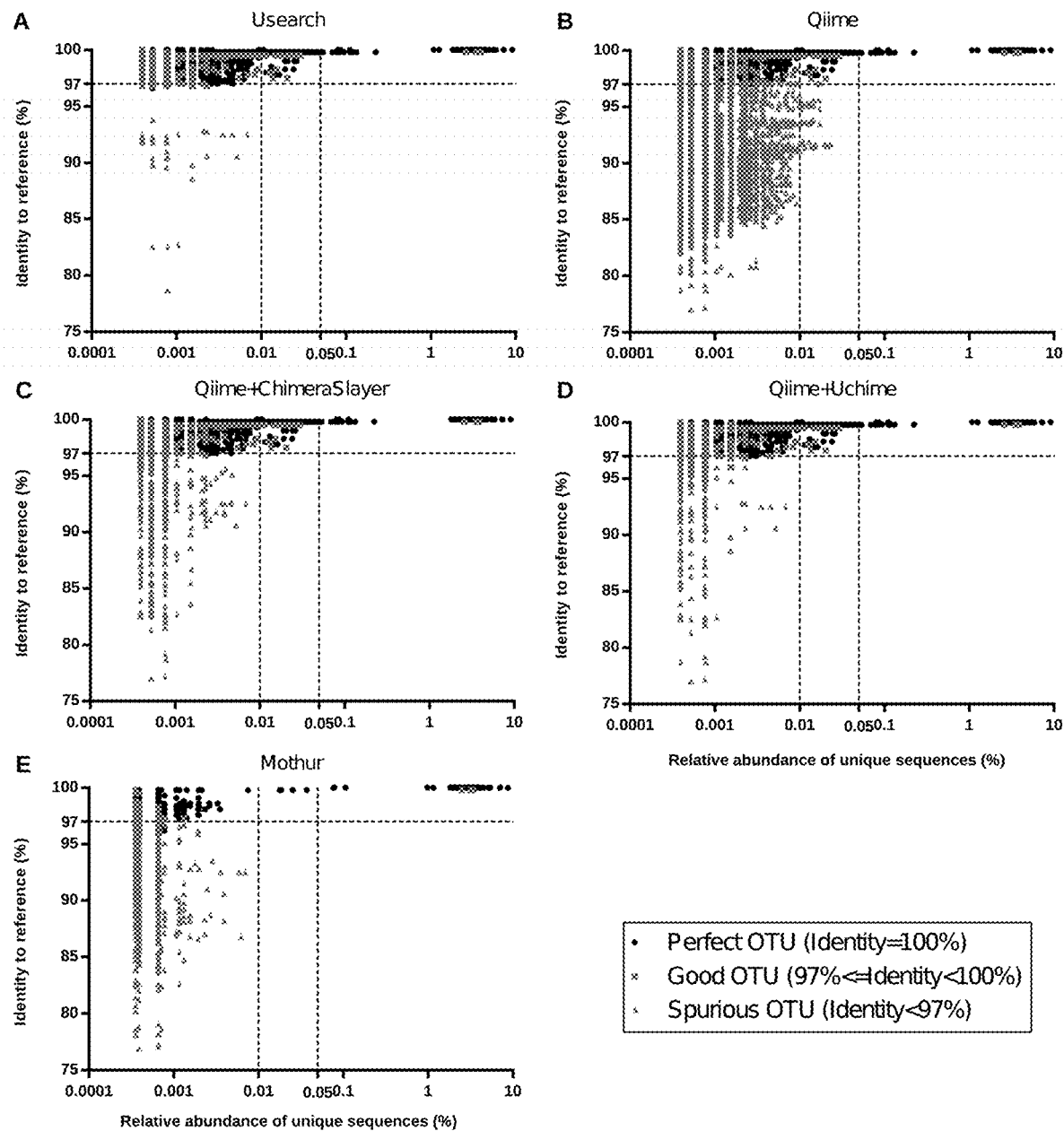
FIG. 5 shows that scatter of unique sequences delineated into three types of OTUs by (A) Usearch, (B) Qiime, (C) Qiime+ChimeraSlayer, (D) Qiime+Uchime and (E) Mothur. Color shows each unique sequence contributing to OTUs identical to mock references (Perfect OTU, Green cycles), with ≥97% identity to reference (Good OTU, Blue cycles), or have >3% errors (Pseudo OTU, Red cycles).

We then traced unique sequences according to the type of OTU (perfect, good, and pseudo) they assigned into (FIG. 5). It turned out that all OTU delineation methods retained "bad" unique sequences (identity<97%), some of which became the centroids of pseudo OTUs. Usearch discarded singletons (unique sequences without replicates) and potential chimeras during OTU delineation, thus distinctly reduced the retained low-identity unique sequences. But discarding singletons alone was not sufficient, since the non-singleton "bad" unique sequences still remained and became the sources of pseudo OTUs (FIG. 5). Moreover, high identity unique sequences (identity≥97%) could be assigned into pseudo OTUs as well, even after chimera filtrations (FIG. 5B-E). It suggested that these "bad sequences" introduced additional pseudo OTUs not only by themselves, but also by seizing high identity sequences, resulting in distorted profiles of "real OTUs".

We also noticed that the relative abundance of the retained low-identity unique sequences didn't exceed 0.05% of "qualified sequences", and was further reduced to <0.01% after chimera filtrations.

Improved OTU Delineation of Mock Data with Our Approach

Figure 6:
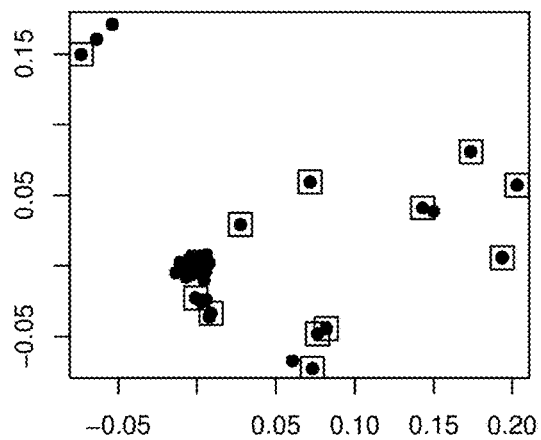
FIG. 6 shows that the divergent effect of low-abundance "bad sequences" on OTU delineation could be eliminated by only considering abundant sequences. The dots represented all the unique sequences belonging to a single plasmid. The hollow red points represented the centroids of OTUs picked by different pipelines.
Figure 6:
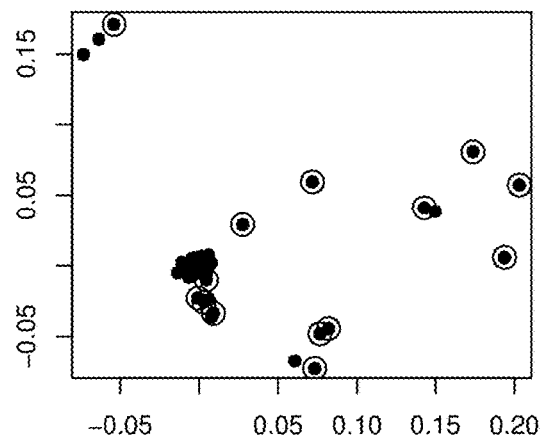
Figure 6:
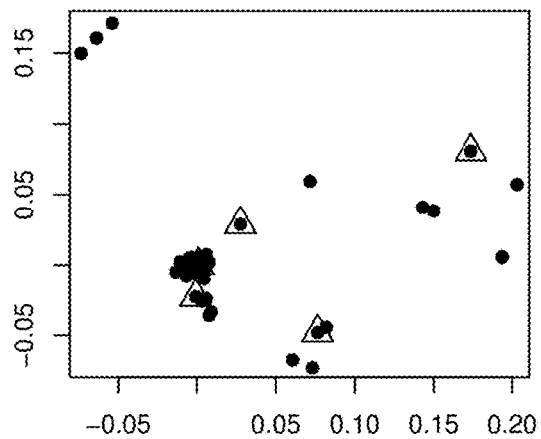
Figure 6:
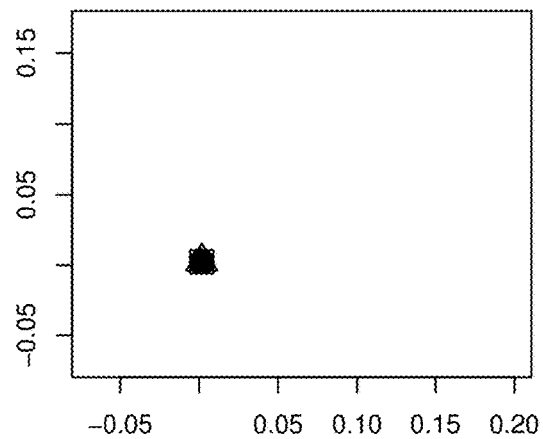

With the mock data, we realized that unique sequences with relatively lower abundance were the major sources of "bad sequences" and pseudo OTUs. It makes sense that the more errors occur in one sequence, the less possibility to have another sequence contains exactly the same errors. Accordingly, the "bad sequences" could be simply eliminated by avoiding all the low-abundance unique sequences from participating in OTU delineation. Most unique sequences belonging to a single plasmid clustered together (FIG. 6), while a few unique sequences having relatively lower abundance distributed dispersedly with <97% similarity to the source plasmid. Some of these sequences were picked as centroids of pseudo OTUs, making the number of OTUs far larger than the actual number of one species. However, if only considering the abundant unique sequences were considered during OTU delineation, all pipelines would result in the real OTUs.

Relative abundance value determination: The sequences are binned into non-redundant unique sequences, the abundance of a unique sequence is the number of replicate sequences that are exactly the same with this unique sequences in the raw data. The relative abundance of a unique sequence is the abundance of this unique sequences divided by the total abundance.

We hence proposed a three-step approach to modify the current analysis pipelines: (i) set up a threshold value of relative abundance of unique sequences, (ii) only input the higher-abundance unique sequences exceeding the threshold into the initial OTU delineation step, and (iii) remap the lower-abundance unique sequences to the obtained OTUs only if they match the 97% similarity threshold.

We set a series of relative abundance thresholds to test our approach (FIG. 7A-C). Shelving unique sequences with relative abundance <0.01% of "qualified sequences" in mock data was already sufficient for Usearch and Mothur, and consistently obtained 22 OTUs corresponding to each mock reference. When the relative abundance threshold was raised to 0.05% or higher, most results obtained 22 OTUs identical or very close to the 22 "real" species except for Qiime+ChimeraSlayer, which yielded only 21 OTUs. The number of OTUs stayed on the plateau until the threshold went higher than 1%, at which level the real species were absent from OTU delineation as well.

Figure 11:
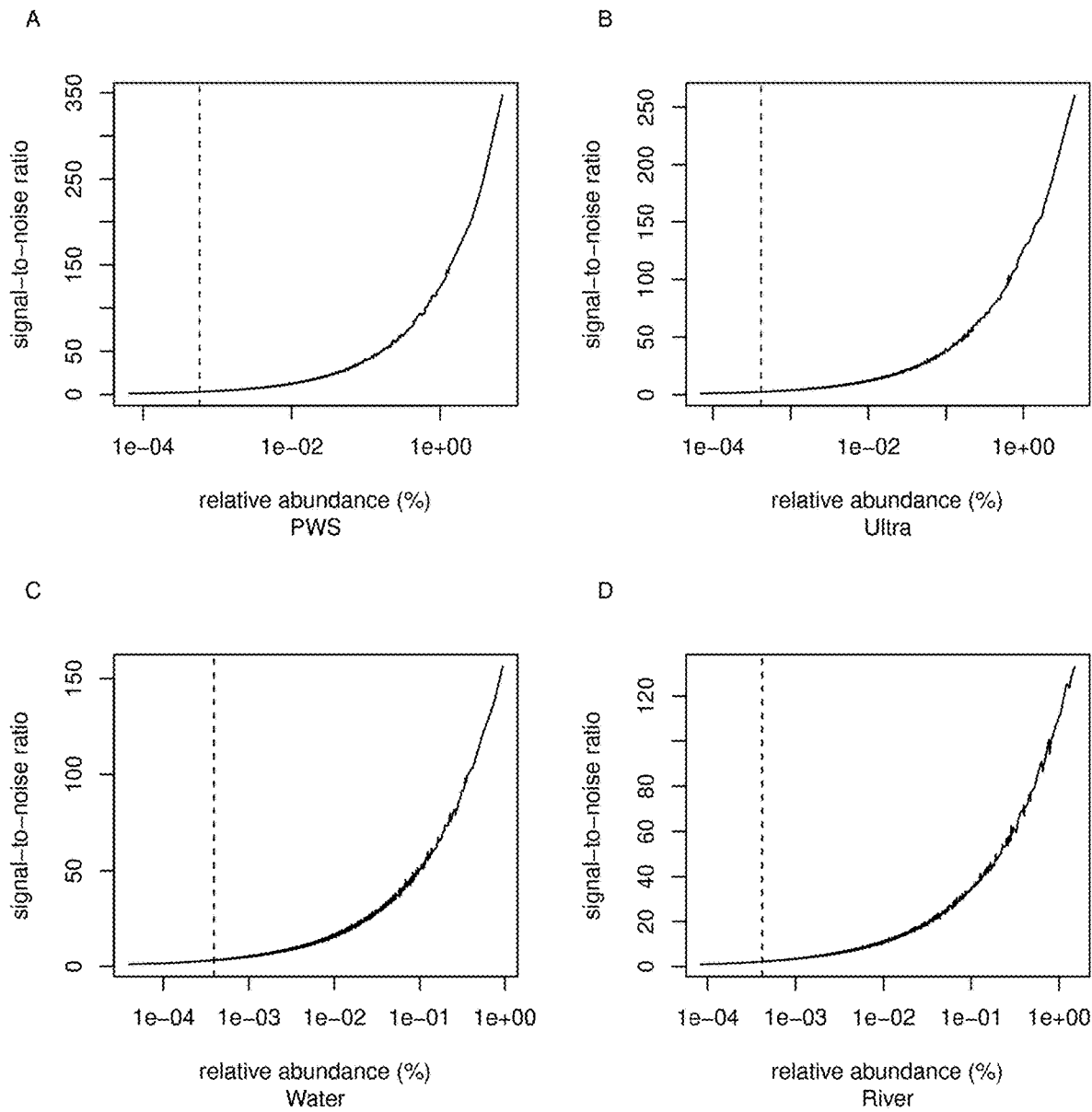
FIG. 11 shows that Signal-to-noise ratio vs. relative abundance in (A) PWS, (B) Ultra, (C) Water, (D) River data. The signal-to-noise ratio decreased quickly along with the decrease of the relative abundance and reached a plateau at lower abundance levels. Dashed vertical lines showed the abundance thresholds for OTU delineation.

When the abundance threshold did not exceed 1%, a maximum of 25-38% of total "qualified sequences" captured by lower-abundance unique sequences did not participate in the initial step of OTU delineation, but they were re-considered by mapping them back to the pre-defined OTUs afterwards. At least 93.9% of "qualified sequences" were finally retained after remapping in Qiime, Mothur or Usearch results. Additional chimera filtration on Qiime picked OTUs apparently affected the remapping ratio, which vibrated in a wide range (FIG. 7D-F).

sequences, bootstrap resampling was performed 1,000 times with replacement. The estimated standard errors of each unique sequence and the corresponding signal-to-noise ratio (abundance/estimated standard error) were calculated. The signal-to-noise ratio decreased quickly along with the decrease of the relative abundance and reached a plateau at lower abundance levels (FIG. 11). Table 4 lists the relative abundance thresholds to set aside 25% "qualified sequences" and the corresponding signal-to-noise values of the four real data sets. The lowest abundances of the unique sequences included in the OTU delineation were already less than 0.0006% and the signal-to-noise ratios were no more than 4, which suggested that all reliable unique sequences had attended the delineation. Besides, all the unique sequences with very low abundance can still be re-joined to the quantitation of OTUs as long as their similarity is at least 97% with the pre-defined OTUs, minimizing the risk of losing the rare but real OTU.

TABLE 4

The abundance thresholds of unique sequences included in OTU delineation and their corresponding signal-to-noise values of the four real data sets.

| Data sets | PWS | Ultra | Water | River |
| --- | --- | --- | --- | --- |
| Lowest abundance level for OTU delineation | 9 | 6 | 10 | 5 |
| Lowest relative abundance level for OTU delineation | 0.00058% | 0.00042% | 0.00039% | 0.00042% |
| Signal/noise* | 3.000 ± 0.072 | 2.500 ± 0.058 | 3.200 ± 0.072 | 2.200 ± 0.053 |

*mean ± standard deviation

Determination of Abundance Threshold

Figure 7:
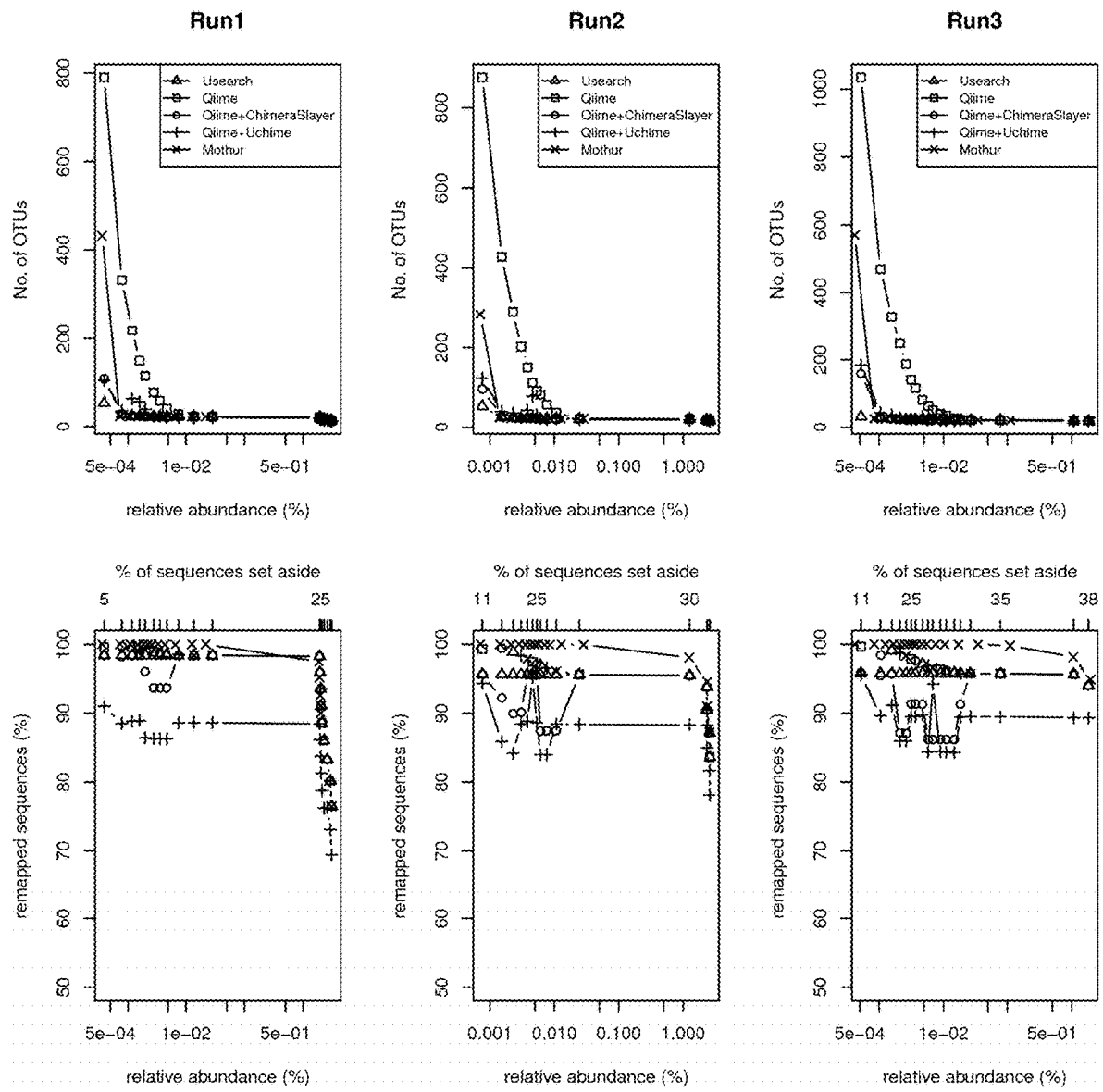
FIG. 7 shows that the OTUs obtained by our proposed approach with different relative abundance thresholds in Mock data. (A-C) The number of OTUs and (D-F) the ratio of sequences remapped to OTU centroids reached a plateau. During initial step of OTU delineation, only unique sequences exceeding the threshold were used. After delineation, all "qualified sequences" were remapped to OTUs with 97% similarity.
Figure 8:
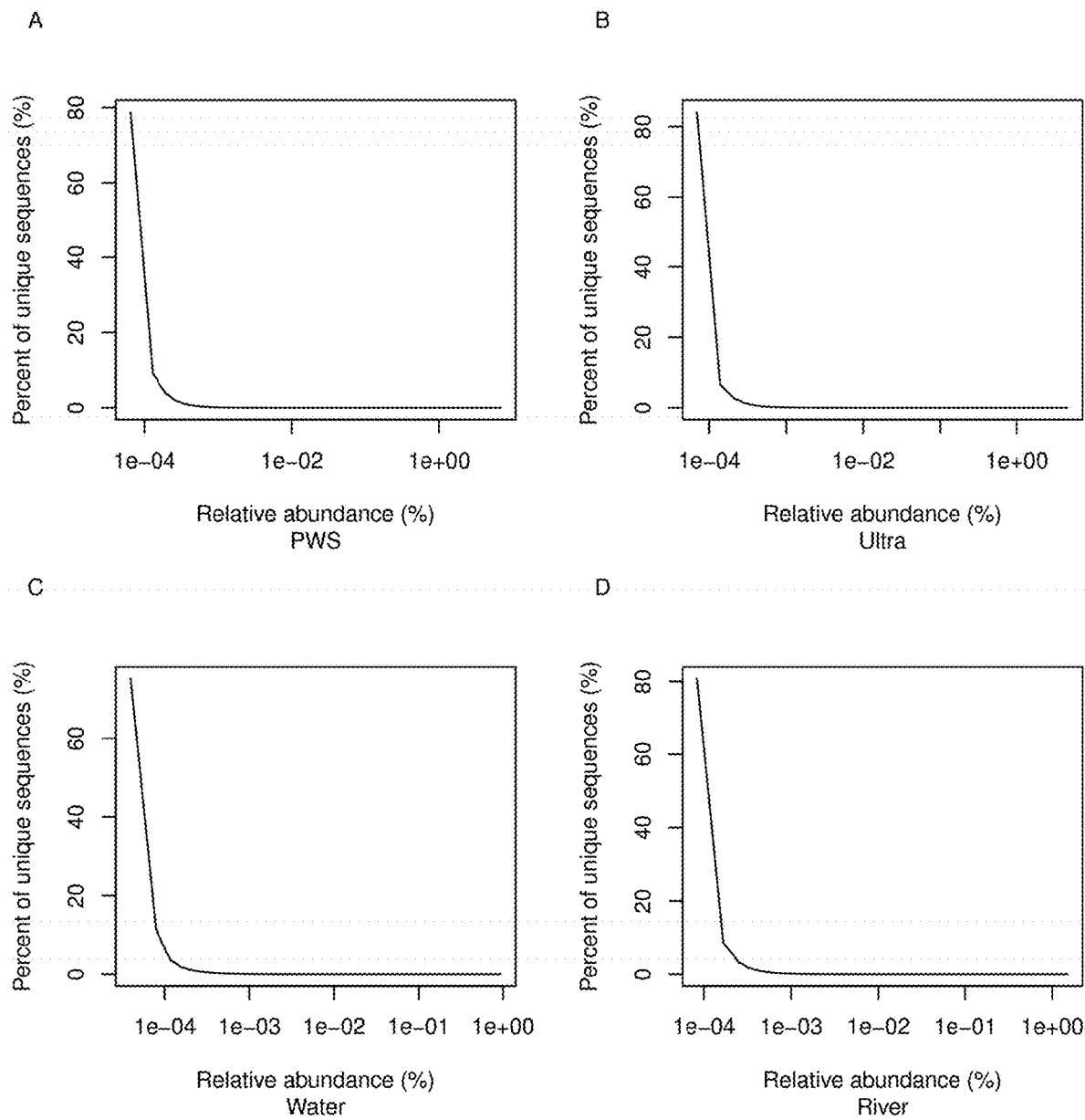
FIG. 8 shows that distribution of unique sequences on their relative abundance in (A) PWS, (B) Ultra, (C) Water, (D) River data. The majority of unique sequences had low abundance.
Figure 9:
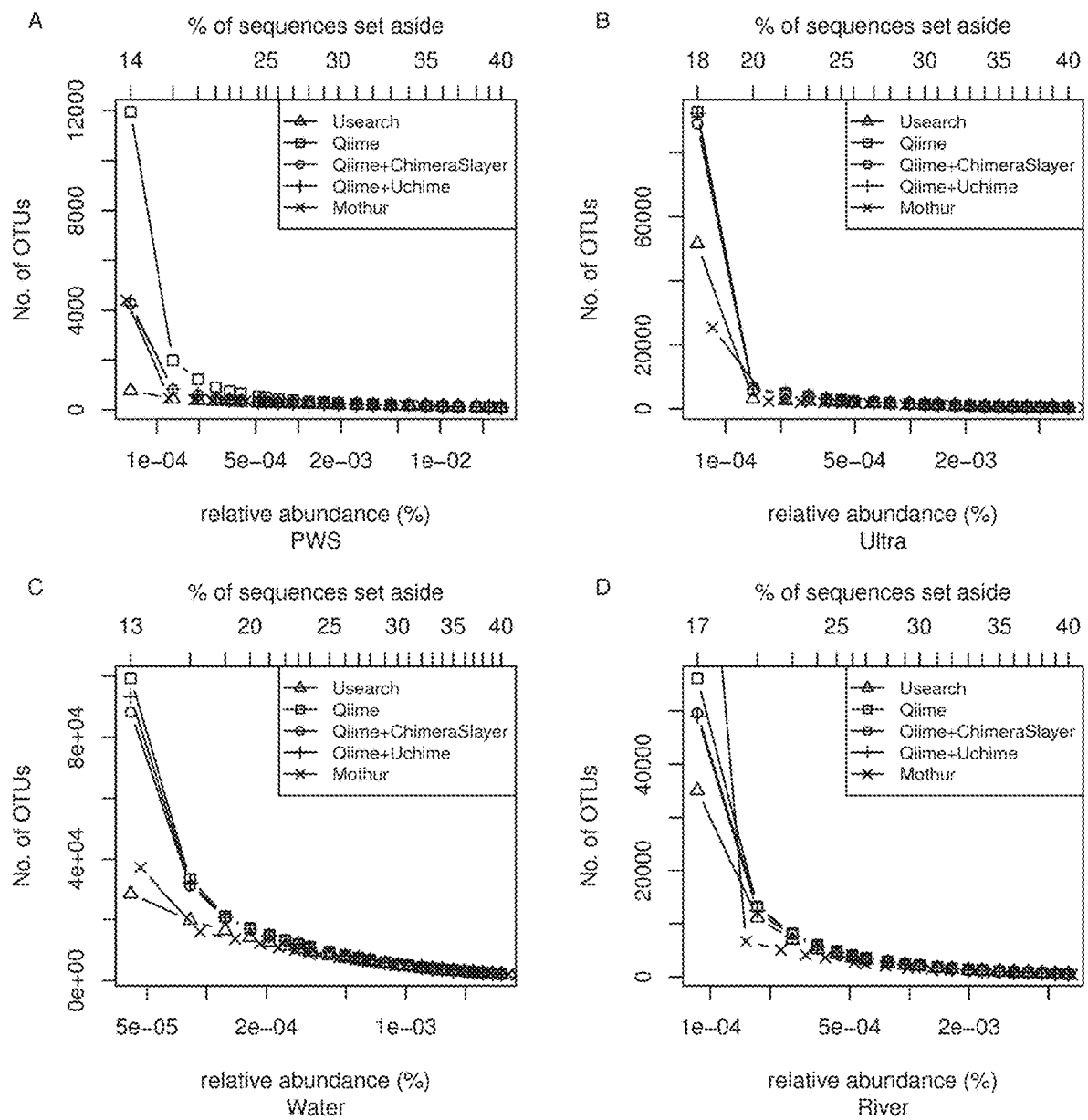
FIG. 9 shows that the OTUs obtained by our proposed approach with different relative abundance thresholds in (A) PWS, (B) Ultra, (C) Water and (D) River data sets. During initial step of OTU delineation, only unique sequences exceeding the threshold were used. The thresholds partitioning the 25% of total "qualified sequences" were applicable for all the real data sets. Different pipelines obtained close number of OTUs at these thresholds.
Figure 10:
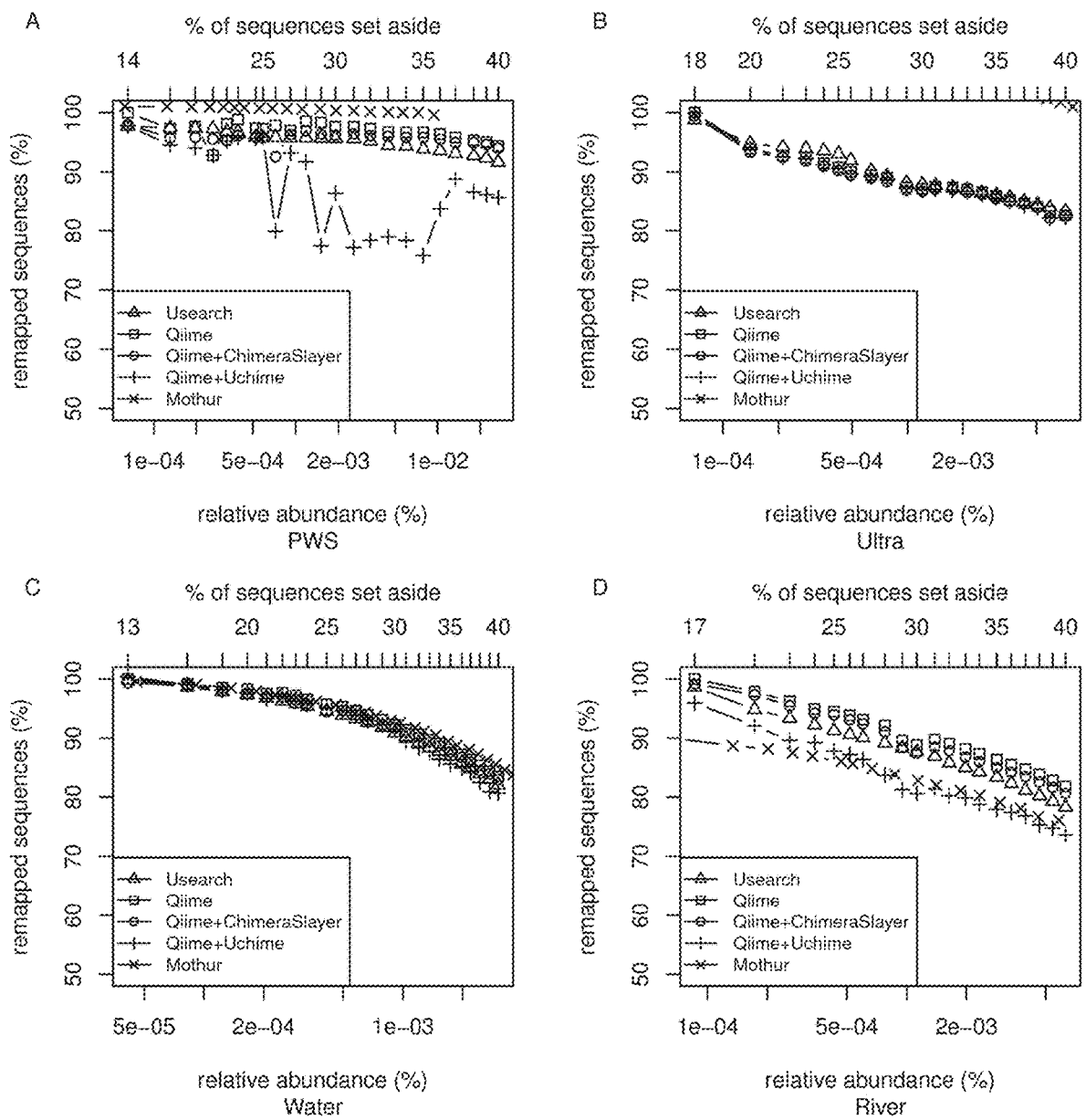
FIG. 10 shows that the ratio of "qualified sequences" remained in (A) PWS, (B) Ultra, (C) Water and (D) River data sets. After OTU delineation, all "qualified sequences" were remapped to OTUs with 97% similarity. At the thresholds partitioning the 25% of total "qualified sequences", >90% of total "qualified sequences" could be remapped back afterwards.

We used four published real data sets to further evaluate our approach and to find out a universally applicable threshold. Though the actual accuracy information of the real data sets was unknown, similar L-shaped distributions of unique sequences after de-replication of "qualified sequences" existed in all the four data (FIG. 8). Each data contained a large amount of low-abundance unique sequences. Incorporating our approach with different pipelines and changing the relative abundance thresholds, we obtained a series of OTU delineation results for each data set (FIG. 9). All results showed a dramatic decrease is number of OTUs at the beginning and a slow descending tendency's maintained as more sequences were set aside from the first step of OTU delineation. Different pipelines implementing distinct algorithms showed divergent behaviors, but at the plateau stage they all obtained a similar number of OTUs. These plateau stages started to occur at the relative abundance levels of about 0.0005% in real data sets (FIG. 9), which were much lower than the levels of about 0.05% in the mock data sets (FIG. 7). In comparison to the mock data, whose communities were only constructed by 22 species, the real data sets were much more complex. The results suggested that the relative abundance could not be chosen as a universally applicable threshold as it may be data specific. However, if the ratio of total "qualified sequences" being set aside is considered, the 25% level appeared at the plateau stage of every data set. At this level, at least 90% of "qualified sequences" could be remapped to pre-defined OTUs (FIG. 7, FIG. 10). That means, avoiding the lowest 25% of total "qualified sequences" from participating OTU delineation would be considered as a potential threshold.

However, a concern does exist that the real OTUs with lower abundance may be host. We hence applied bootstrap to estimate the uncertainty level of unique sequences. For each data, according to the original distribution of unique More Consistent Alpha and Beta Diversities in Real Data Sets with Our Approach Take the PWS data cite as an example, by performing OTU delineation on 7,798 unique sequences instead of 278,160 ones, our approach dramatically saved the computing resources and calculation time. It also significantly lessened the total number of OTUs for this real data set, from 430 to 272 (Usearch), 7,979 to 493 (Qiime alone), 1,671 to 302 (Qiime with ChimeraSlayer), 1,621 to 327 (Qiime with Uchime) and 4,419 to 328 (Mothur), respectively (FIG. 12A).

Figure 12:
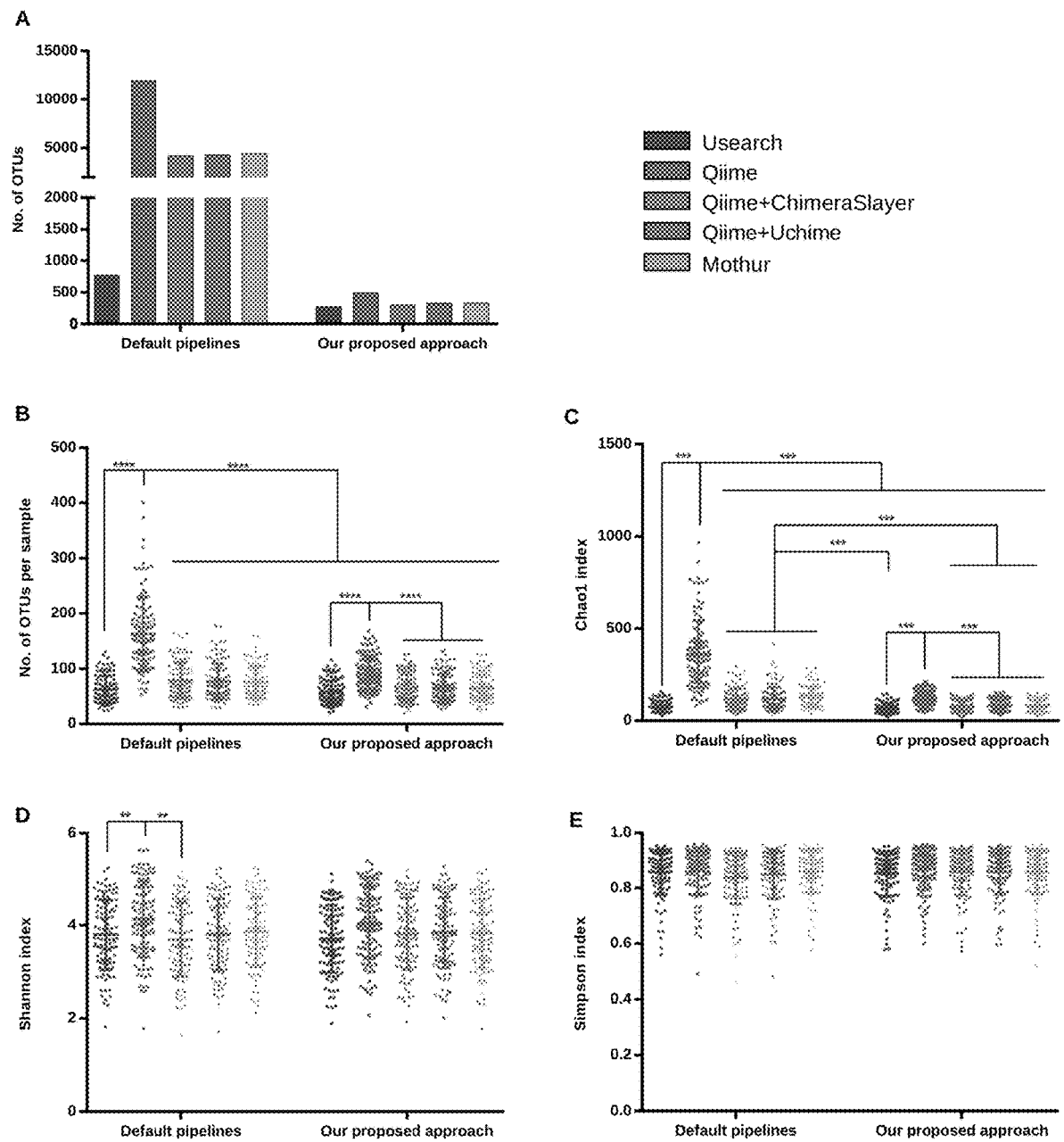
FIG. 12 shows that our proposed approach resulted in less OTUs but comparable alpha diversity in PWS data. (A) Total number of OTUs picked by each pipeline. (B) Number of OTUs per sample. (C) Chao1 indices. (D) Shannon indices. (E) Simpson indices. Default workflows: performing default parameters in each pipeline. Our proposed approach: the relative abundance threshold of unique sequences was set at 0.00058%. $p<0.01$, *$p<0.001$, ****$p<0.0001$ (Kruskal-Wallis test, n=108). Sequencing number was rarified to 4,000 reads/sample before calculation of alpha diversity indices.

For comparison of alpha diversities, the number of OTUs, Chao1[21], Shannon[22] and Simpson[23] index of each sample were calculated (FIG. 12 for PWS data,). The first two indices directly reflect the richness of samples, while the latter two reflect overall diversity information. Due to their great disparities of total OTU numbers, significant differences occurred between default pipelines and our approaches on the estimate of numbers of OTUs per sample (FIG. 12B) and Chao1 indices (FIG. 12C) (according to Kruskal-Wallis test[24]). These two indices also differed among OTU pipelines with default parameters (FIG. 12B-C). But there was no significant difference between default pipelines and our approach on Shannon (FIG. 12D) and Simpson (FIG. 12E) indices. Results of Qiime with default parameters were always significantly higher than others, mainly due to its unreasonably large number of OTUs.

Figure 13:
FIG. 13 shows that our proposed approach resulted in more consistent beta diversity with different pipelines in PWS data. Mantel Statistics were obtained by comparing Beta diversity distance matrices between each pair of analysis pipelines with (A) Default pipelines, (B) Our proposed approach incorporated with different pipelines. Sequencing number was rarified to 4,000 reads/sample before calculation of beta diversity distance matrices.
Figure 13:
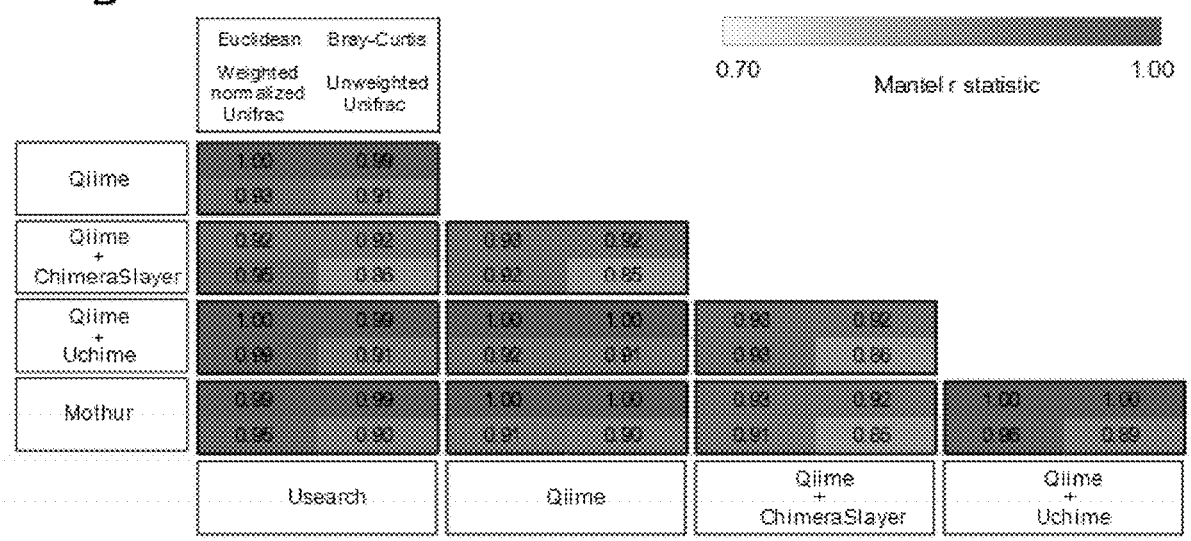

To test how these differences in OTU delineation may influence biological interpretation, four types of beta diversity distance matrices, including Euclidean (EU), Bray-Curtis (BC)[25], weighted normalized Unifrac (WU) and unweighted Unifrac (UU)[26] distance were measured. Distance matrices calculated on OTU tables obtained by different OTU delineations were compared by the Mantel test[27], their similarities were indicated by Mantel r statistics (FIG. 13 for PWS data, FIGS. 9-11 for other data sets). We observed that in PWS data UU provided distinct beta diversity estimates among default pipelines (FIG. 13A, Mantel r=0.73~0.86), but became more correlated with each other using our approach (FIG. 13B, Mantel r=0.85~0.91). EU and BC distances correlated very well (Mantel r>0.95) between default pipelines and further enlarged (Mantel r>0.99) between all methods except Qiime+ChimeraSlayer with our approach (Mantel r=0.92~0.93 for EU, 0.92 for BC). Correlation of WU distance between methods didn't change with the shift from default pipelines to our approach.

Example 2

The embodiments of this disclosure further provide a non-transitory computer-readable storage medium storing executable instructions that, when executed by an electronic device, cause the electronic device to:obtain a relative abundance value of each of qualified sequences of a phylogenetically informative gene in microorganisms contained in the sample, wherein the total relative abundance of all qualified sequences is 100%; rank from high to low all qualified sequences by their respective relative abundance value, and separating the qualified sequences into a high abundance group and a low abundance group, wherein the high abundance group consists of qualified sequences whose abundance values are higher than the those in the low abundance group and collectively account for about 70%-80% of the total abundance; and the low abundance group consists of the remaining qualified sequences which account for about 20%-30% of the total abundance; delineate OTUs in the sample using only qualified sequences in the high abundance group to obtain Tentative OTUs; and re-map qualified sequences in the low abundance group to the Tentative OTUs, and assigning them individually to a suitable Tentative OTUs only if they the qualified sequence has at least 90% sequence similarly to the OTU Sequence, to arrive at the final definition of OTUs.

Example 3

Figure 15:
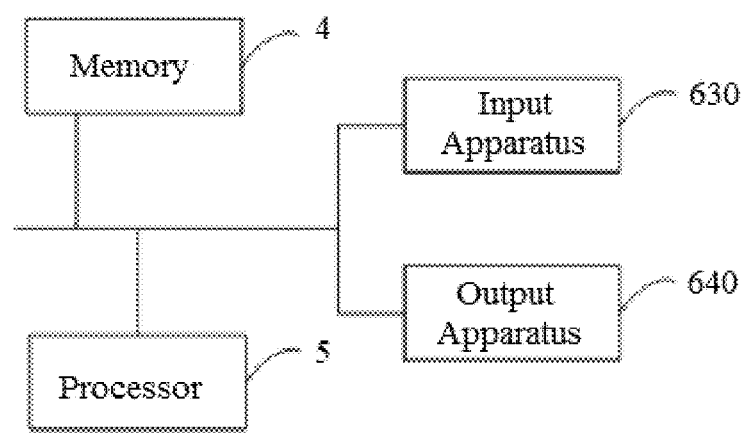
FIG. 15 is a schematic diagram of a hardware structure of an electronic device according to the embodiment of this disclosure.

FIG. 15 is a schematic diagram of the hardware configuration of the electronic device provided by the embodiment, which performs the method of defining microbial operational taxonomic units (OTUs). As shown in FIG. 15, the electronic device includes: one or more processors 5 and a memory 4, wherein one processor 5 is shown in FIG. 15 as an example. The electronic device that performs the method further includes an input apparatus 630 and an output apparatus 640.

The processor 5, the memory 4, the input apparatus 630 and the output apparatus 640 may be connected via a bus line or other means, wherein connection via a bus line is shown in FIG. 15 as an example.

The memory 4 is a non-transitory computer-readable storage medium that can be used to store non-transitory software programs, non-transitory computer-executable programs and modules, such as the program instructions/modules corresponding to the user management method of the embodiments of the application (e.g. the first module, the second module, the third module, and the fourth module in the present application). The processor 5 executes the non-transitory software programs, instructions and modules stored in the memory 4 so as to perform various function application and data processing of the server, thereby implementing the user management method of the above-mentioned method embodiments The memory 4 includes a program storage area and a data storage area, wherein, the program storage area can store an operation system and application programs required for at least one function; the data storage area can store data generated by use of the user management system. Furthermore, the memory 4 may include a high-speed random access memory, and may also include a non-volatile memory, e.g. at least one magnetic disk memory unit, flash memory unit, or other non-volatile solid-state memory unit. In some embodiments, optionally, the memory 4 includes a remote memory accessed by the processor 5, and the remote memory is connected to the system defining microbial operational taxonomic units (OTU) via network connection. Examples of the aforementioned network include but not limited to: internet, intranet, LAN, GSM, and their combinations.

The input apparatus 630 receives digit or character information, so as to generate signal input related to the user configuration and function control of the electronic device defining microbial operational taxonomic units (OTU). The output apparatus 640 includes display devices such as a display screen.

The one or more modules are stored in the memory 4 and, when executed by the one or more processors 5, perform the method of defining microbial operational taxonomic units (OTU) of any one of the above-mentioned method embodiments.

The above-mentioned product can perform the method provided by the embodiments of the application and have function modules as well as beneficial effects corresponding to the method. Those technical details not described in this embodiment can be known by referring to the method provided by the embodiments of the application.

The electronic device of the embodiments of the application can exist in many forms, including but not limited to:

(1) Mobile communication devices: The characteristic of this type of device is having a mobile communication function with a main goal of enabling voice and data communication. This type of terminal device includes: smartphones (such as iPhone), multimedia phones, feature phones, and low-end phones.

(2) Ultra-mobile personal computer devices: This type of device belongs to the category of personal computers that have computing and processing functions and usually also have mobile internet access features. This type of terminal device includes: PDA, MID, UMPC devices, such as iPad.

(3) Portable entertainment devices: This type of device is able to display and play multimedia contents. This type of terminal device includes: audio and video players (such as iPod), handheld game players, electronic books, intelligent toys, and portable GPS devices.

(4) Servers: devices providing computing service. The structure of a server includes a processor, a hard disk, an internal memory, a system bus, etc. A server has an architecture similar to that of a general purpose computer, but in order to provide highly reliable service, a server has higher requirements in aspects of processing capability, stability, reliability, security, expandability, manageability.

(5) Other electronic devices having data interaction function.

The above-mentioned device embodiments are only illustrative, wherein the units described as separate parts may be or may not be physically separated, the component shown as a unit may be or may not be a physical unit, i.e. may be located in one place, or may be distributed at multiple network units. According to actual requirements, part of or all of the modules may be selected to attain the purpose of the technical scheme of the embodiments.

By reading the above-mentioned description of embodiments, those skilled in the art can clearly understand that the various embodiments may be implemented by means of software plus a general hardware platform, or just by means of hardware. Based on such understanding, the above-mentioned technical scheme in essence, or the part thereof that has a contribution to related prior art, may be embodied in the form of a software product, and such a software product may be stored in a computer-readable storage medium such as ROM/RAM, magnetic disk or optical disk, and may include a plurality of instructions to cause a computer device (which may be a personal computer, a server, or a network device) to execute the methods described in the various embodiments or in some parts thereof.

Finally, it should be noted that: The above-mentioned embodiments are merely illustrated for describing the technical scheme of the application, without restricting the technical scheme of the application. Although detailed description of the application is given with reference to the above-mentioned embodiments, those skilled in the art should understand that they still can modify the technical scheme recorded in the above-mentioned various embodiments, or substitute part of the technical features therein with equivalents. These modifications or substitutes would not cause the essence of the corresponding technical scheme to deviate from the concept and scope of the technical scheme of the various embodiments of the application.

REFERENCES

1. Goodrich, J. K. et al. Conducting a Microbiome Study. *Cell* 158, 250-262 (2014).
2. Schloss, P. D. & Westcott, S. L. Assessing and Improving Methods Used in Operational Taxonomic Unit-Based Approaches for 16S rRNA Gene Sequence Analysis. *Appl. Environ. Microbiol.* 77, 3219-3226 (2011).
3. Fei, N. & Zhao, L. An opportunistic pathogen isolated from the gut of an obese human causes obesity in germfree mice. *ISME J* 7, 880-884 (2013).
4. Zhang, C. et al. Dietary modulation of gut microbiota contributes to alleviation of both genetic and simple obesity in children. *EBioMedicine* doi:10.1016/j.ebiom.2015.07.007
5. Chen, W., Zhang, C. K., Cheng, Y., Zhang, S. & Zhao, H. A Comparison of Methods for Clustering 16S rRNA Sequences into OTUs. *PLoS ONE* 8, e70837 (2013).
6. Bonder, M. J., Abeln, S., Zaura, E. & Brandt, B. W. Comparing clustering and pre-processing in taxonomy analysis. *Bioinformatics* 28, 2891-2897 (2012).
7. Edgar, R. C. UPARSE: highly accurate OTU sequences from microbial amplicon reads. *Nat. Methods* 10, 996-998 (2013).
8. Kozich, J. J., Westcott, S. L., Baxter, N. T., Highlander, S. K. & Schloss, P. D. Development of a Dual-Index Sequencing Strategy and Curation Pipeline for Analyzing Amplicon Sequence Data on the MiSeq Illumina Sequencing Platform. *Appl. Environ. Microbiol.* 79, 5112-5120 (2013).
9. Caporaso, J. G. et al. QIIME allows analysis of high-throughput community sequencing data. *Nat Methods* 7, 335-6 (2010).
10. Klindworth, A. et al. Evaluation of general 16S ribosomal RNA gene PCR primers for classical and next-generation sequencing-based diversity studies. *Nucleic Acids Res.* 41, e1 (2013).
11. Bokulich, N. A. et al. Quality-filtering vastly improves diversity estimates from Illumina amplicon sequencing. *Nat Methods* (2012). doi:10.1038/nmeth.2276
12. Schirmer, M. et al. Insight into biases and sequencing errors for amplicon sequencing with the Illumina MiSeq platform. *Nucleic Acids Res.* (2015). doi:10.1093/nar/gku1341
13. Schloss, P. D. et al. Introducing mothur: open-source, platform-independent, community-supported software for describing and comparing microbial communities. *Appl. Environ. Microbiol.* 75, 7537-7541 (2009).
14. Aronesty, E. Comparison of sequencing utility programs. *Open Bioinform J* 7, 1-8 (2013).
15. Joshi, N. A. & Fass, J. N. Sickle: *A sliding-window, adaptive, quality-based trimming tool for FastQ files* (Version 1.33). (2011). at <https://github.com/najoshi/sickle>
16. Nikolenko, S. I., Korobeynikov, A. I. & Alekseyev, M. A. BayesHammer: Bayesian clustering for error correction in single-cell sequencing. *BMC Genomics* 14, S7 (2013).
17. Masella, A. P., Bartram, A. K., Truszkowski, J. M., Brown, D. G. & Neufeld, J. D. PANDAseq: paired-end assembler for illumina sequences. *BMC Bioinformatics* 13, 31 (2012).
18. Edgar, R. C. Search and clustering orders of magnitude faster than BLAST. *Bioinformatics* 26, 2460-2461 (2010).
19. Haas, B. J. et al. Chimeric 16S rRNA sequence formation and detection in Sanger and 454-pyrosequenced PCR amplicons. *Genome Res.* 21, 494-504 (2011).
20. Edgar, R. C., Haas, B. J., Clemente, J. C., Quince, C. & Knight, R. UCHIME improves sensitivity and speed of chimera detection. *Bioinformatics* 27, 2194-2200 (2011).
21. Chao, A. Nonparametric Estimation of the Number of Classes in a Population. *Scand. J. Stat.* 11, 265-270 (1984).
22. Shannon, C. E. A Mathematical Theory of Communication. *Bell Syst. Tech. J.* 27, 379-423 (1948).
23. Simpson, E. H. Measurement of Diversity. *Nature* 163, 688 (1949).
24. Hollander, M. & Wolfe, D. A. *NonparametricStatistical Methods*. (Hoboken, N.J.: John Wiley & Sons, Inc., 1999).
25. Bray, J. R. & Curtis, J. T. An ordination of the upland forest communities of southern Wisconsin. *Ecol. Monogr.* 27, 325-349 (1957).
26. Lozupone, C. & Knight, R. UniFrac: a new phylogenetic method for comparing microbial communities. *Appl Env. Microbiol* 71, 8228-35 (2005).
27. Mantel, N. The detection of disease clustering and a generalized regression approach. *Cancer Res* 27, 209-20 (1967).
28. DePristo, M. A. et al. A framework for variation discovery and genotyping using next-generation DNA sequencing data. *Nat. Genet.* 43, 491-498 (2011).
29. Edgar, R. C. & Flyvbjerg, H. Error filtering, pair assembly, and error correction for next-generation sequencing reads. *Bioinformatics* btv401 (2015).
30. Caporaso, J. G. et al. Ultra-high-throughput microbial community analysis on the Illumina HiSeq and MiSeq platforms. *ISME J* 6, 1621-4 (2012).
31. Roeselers, G. et al. Microbial biogeography of drinking water: patterns in phylogenetic diversity across space and time: Microbial biogeography of drinking water systems. *Environ. Microbiol.* 17, 2505-2514 (2015).
32. Savio, D. et al. Bacterial diversity along a 2600 km river continuum: River bacterioplankton diversity. *Environ. Microbiol.* n/a-n/a (2015). doi:10.1111/1462-2920.12886
33. Bertilsson, S. Transitions in bacterial communities along the 2000 km salinity gradient of the Baltic Sea. *Isme J.* 5, 1571-1579 (2011).
34. Cole, J. R. et al. Ribosomal Database Project: data and tools for high throughput rRNA analysis. *Nucleic Acids Res.* 42, D633-642 (2014).
35. Quast, C. et al. The SILVA ribosomal RNA gene database project: improved data processing and web-based tools. *Nucleic Acids Res.* gks1219 (2012).
36. DeSantis, T. Z. et al. Greengenes, a chimera-checked 16S rRNA gene database and workbench compatible with ARB. *Appl. Environ. Microbiol.* 72, 5069-5072 (2006).

The invention claimed is:

1. A method for isolating a microorganism from an environmental sample, wherein the microorganism comprises a phylogenetically informative gene, the method comprising:
determining microbial operational taxonomic units (OTUs) in the environmental sample by the steps of;
1)—obtaining a relative abundance value of each of qualified sequences of a phylogenetically informative gene in microorganisms contained in the sample, wherein the total relative abundance of all qualified sequences is 100%, wherein a relative abundance value of each of qualified sequences of a phylogenetically informative gene in microorganisms contained in the sample are obtained by the following steps;
a)—obtaining a sample, which comprises microorganisms each of which comprises a phylogenetically information gene,
b)—obtaining raw sequence reads of the phylogenetically informative gene of the microorganisms in the sample using a PCR-based high-throughput sequencing technique,
c)—processing the raw sequence reads to obtain assembled, fully-length qualified sequences,
d)—obtaining a relative abundance value of each of the qualified sequences, wherein the total relative abundance of all qualified sequences is 100%;
2)—ranking from high to low all qualified sequences by their respective relative abundance value, and separating the qualified sequences into a high abundance group and a low abundance group, wherein the high abundance group consists of qualified sequences whose abundance values are higher than those in the low abundance group and collectively account for 70%-80% of the total abundance; and the low abundance group consists of the remaining qualified sequences which account for 20%-30% of the total abundance;
3)—delineating OTUs in the sample using only qualified sequences in the high abundance group to obtain Tentative OTUs; and
4)—re-mapping qualified sequences in the low abundance group to the Tentative OTUs, and assigning them individually to a suitable Tentative OTUs only if the qualified sequence has at least 90% sequence similarly to the OTU Sequence, to arrive at the final definition of OTUs;
selecting an OTU with its unique phylogenetically informative gene sequence as a to-be-isolated microorganism;
culturing microorganisms in the sample;
determining the DNA sequence of the phylogenetically informative gene of each of the cultured microorganisms; and
isolating a microorganism the sequence of whose phylogenetically informative gene is homologous to the phylogenetically informative gene sequence of the to-be-isolated microorganism.

2. The method according to claim 1, wherein the microorganism is a bacterium.

3. The method according to claim 1, wherein a microorganism the sequence of whose phylogenetically informative gene is at least 95% identical to the phylogenetically informative gene sequence of the to-be-isolated microorganism is isolated.

4. The method according to claim 3, wherein a microorganism the sequence of whose phylogenetically informative gene is at least 99% identical to the phylogenetically informative gene sequence of the to-be-isolated microorganism is isolated.

5. The method according to claim 4, wherein a microorganism the sequence of whose phylogenetically informative gene is identical to the phylogenetically informative gene sequence of the to-be-isolated microorganism is isolated.

* * * * *

SEQUENCE LISTING

```
<160> NUMBER OF SEQ ID NOS: 22

<210> SEQ ID NO 1
<211> LENGTH: 1493
<212> TYPE: DNA
<213> ORGANISM: Blautia

<400> SEQUENCE: 1
gagagtttga tcctggctca ggatgaacgc tggcggcgtg cttaacacat gcaagtcgaa      60
cgggaattac tttattgaaa cttcggtcga tatgatttaa ttctagtggc ggacgggtga     120
gtaacgcgtg ggtaacctgc cttgtacagg gggataacag tcagaaatga ctgctaatac     180
cgcataagcg cacaggaccg catggtccgg tgtgaaaaac tccggtggta taagatggac     240
ccgcgttgga ttagctagtt ggtgaggtaa cggcccacca aggcgacgat ccatagccgg     300
cctgagaggg tgaacggcca cattgggact gagacacggc ccagactcct acgggaggca     360
gcagtgggga atattgcaca atgggggaaa ccctgatgca gcgacgccgc gtgaaggaag     420
aagtatctcg gtatgtaaac ttctatcagc agggaagaaa atgacggtac ctgactaaga     480
agccccggct aactacgtgc cagcagccgc ggtaatacgt aggggggcaag cgttatccgg     540 atttactggg tgtaaaggga gcgtagacgg atggacaagt ctgatgtgaa aggctggggc     600
tcaaccccgg gactgcattg gaaactgccc gtcttgagtg ccggagaggt aagcggaatt     660
cctagtgtag cggtgaaatg cgtagatatt aggaggaaca ccagtggcga aggcggctta     720
ctggacggta actgacgttg aggctcgaaa gcgtggggag caaacaggat tagataccct     780
ggtagtccac gccgtaaacg atgaatgcta ggtgtcgggt gacgaagtca ttcggtgccg     840
ccgcaaacgc attaagcatt ccacctgggg agtacgttcg caagaatgaa actcaaagga     900
attgacgggg acccgcacaa gcggtggagc atgtggttta attcgaagca acgcgaagaa     960
ccttaccaag tcttgacatc cttctgaccg gaacttaacc gttccttccc ttcggggcag    1020
aagtgacagg tggtgcatgg ttgtcgtcag ctcgtgtcgt gagatgttgg gttaagtccc    1080
gcaacgagcg caacccctat cctcagtagc cagcatataa gatgggcact ctgtggagac    1140
tgccagggat aacctggagg aaggcgggga tgacgtcaaa tcatcatgcc ccttatgatt    1200
tgggctacac acgtgctaca atggcgtaaa caaagggaag cgaacctgcg agggtgggca    1260
aatcccaaaa ataacgtccc agttcggact gtagtctgca acccgactac acgaagctgg    1320
aatcgctagt aatcgcggat cagaatgccg cggtgaatac gttcccgggt cttgtacaca    1380
ccgcccgtca caccatggga gtcagtaacg cccgaagtca gtgacctaac gcaaggaag    1440 gagctgccga aggcgggacc gatgactggg gtgaagtcgt aacaaggtag ccg           1493

<210> SEQ ID NO 2
<211> LENGTH: 1522
<212> TYPE: DNA
<213> ORGANISM: Allisonella

<400> SEQUENCE: 2
```

-continued

```
gagagtttga tcctggctca ggacgaacgc tggcggcgtg cctaacacat gcaagtcgaa      60
cggagaattt tatttcggta gaattcttag tggcgaacgg gtgagtaacg cgtaggcaac     120
ctgcccttta gacggggaca acattccgaa aggagtgcta ataccggatg tgatcatctt     180
gccgcatggc aggatgaaga aagatggcct ctacaagtaa gctatcgcta aaggatgggc     240
ctgcgtctga ttagctagtt ggtagtgtaa cggactacca aggcgatgat cagtagccgg     300
tctgagagga tgaacggcca cattgggact gagacacggc ccaaactcct acggaggca     360
gcagtgggga atcttccgca atggacgaaa gtctgacgga gcaacgccgc gtgaacgatg     420
aaggtcttcg gattgtaaag ttctgtgatc cgggacgaag gcatcaattg agaatattga     480
ttgatgttga cggtaccgga aaagcaagcc acggctaact acgtgccagc agccgcggta     540
atacgtaggt ggcaagcgtt gtccggaatt attgggcgta aagcgcgcgc aggcggccgt     600
gcaagtccat cttaaaagcg tggggcttaa ccccatgagg ggatggaaac tgcagggctg     660
gagtgtcgga ggggaaagtg gaattcctag tgtagcggtg aaatgcgtag agattaggaa     720
gaacaccggt ggcgaaggcg actttctaga cgacaactga cgctgaggcg cgaaagcgtg     780
gggagcaaac aggattagat accctggtag tccacgccgt aacgatggat actaggtgta     840
ggaggtatcg accccttctg tgccggagtt aacgcaataa gtatcccgcc tgggaagtac     900
gatcgcaaga ttaaaactca aaggaattga cgggggcccg cacaagcggt ggagtatgtg     960
gtttaattcg acgcaacgcg aagaacctta ccaagccttg acattgatcg caatctgcag    1020
aaatgcggag ttcctcttcg gaggacgaga aaacaggtgg tgcacggctg tcgtcagctc    1080
gtgtcgtgag atgttgggtt aagtcccgca acgagcgcaa cccctatctt ctgttgccag    1140
cacgtaaagg tgggaactca ggagagaccg ccgcggacaa cgcggaggaa ggcggggatg    1200
acgtcaagtc atcatgcccc ttatggcttg ggctacacac gtactacaat gggtgcaaac    1260
aaagagaagc gaagtcgcga gacggagcgg acctcataaa cgcactccca gttcagattg    1320
caggctgcaa cccgcctgca tgaagtagga atcgctagta atcgcgggtc agcataccgc    1380
ggtgaatacg ttcccgggcc ttgtacacac cgcccgtcac actatgagag tcagagacac    1440
ccaaagccgg tgggataacc gaaagggatc agccgtctaa ggtggagctg atgattggag    1500
tgaagtcgta acaaggtagc cg                                             1522
```

<210> SEQ ID NO 3
<211> LENGTH: 1492
<212> TYPE: DNA
<213> ORGANISM: Paraprevotella

<400> SEQUENCE: 3

```
agagtttgat cctggctcag gatgaacgct agctacaggc ttaacacatg caagtcgagg      60
ggcagcatgg acccagtttt gctgggtttg atggcgaccg gcgcacgggt gagtaacgcg     120
tatccaacct gcccttttact ccgggatagt ctcctgaaag ggagtttaat accgatgtg     180
tttgtctttc cgcatgggag cgacaaataa agattgattg gtaaaggatg gggatgcgtc     240
ccattagctt gttggcgggg taacggccca ccaaggcgac gatgggtagg ggttctgaga     300
ggaaggtccc ccacattgga actgagacac ggtccaaact cctacgggag gcagcagtga     360
ggaatattgg tcaatgggcg ggagcctgaa ccagccaagt agcgtgaagg atgacggccc     420
tacggggttgt aaacttctttt tataagggaa taaagttcgc cacgtgtggt gttttgtatg     480
taccttatga ataagcatcg gctaattccg tgccagcagc cgcggtaata cggaagatgc     540
```

```
gagcgttatc cggatttatt gggtttaaag ggagcgtagg cgggctttta agtcagcggt      600
caaatgccac ggctcaaccg tggccagccg ttgaaactgc aagccttgag tctgcacagg      660
gcacatggaa ttcgtggtgt agcggtgaaa tgcttagata tcacgaagaa ctccgatcgc      720
gaaggcattg tgccggggca gcactgacgc tgaggctcga agtgcgggt atcaaacagg      780 attagatacc ctggtagtcc gcacggtaaa cgatgaatgc tcgctatggg cgatacaatg      840
tccgtggcca agcgaaagcg ttaagcattc cacctgggga gtacgccggc aacggtgaaa      900
ctcaaaggaa ttgacggggg cccgcacaag cggaggaaca tgtggtttaa ttcgatgata      960
cgcgaggaac cttacccggg cttgaattgc aggtgcatga gtcggagacg gctctttcct     1020
tcgggactcc tgtgaaggtg ctgcatggtt gtcgtcagct cgtgccgtga ggtgtcggct     1080
taagtgccat aacgagcgca acccttctcc cagttgccca tcgggtaatg ccgggccctc     1140
tggggacact gccatcgtaa gatgcgagga aggtggggat gacgtcaaat cagcacggcc     1200
cttacgtccg ggctacaca cgtgttacaa tgggggtac agagggccgc tgtccggtga      1260
cggtcggcca atccctaaaa ctcctctcag ttcggactgg agtctgcaac ccgactccac     1320
gaagctggat tcgctagtaa tcgcgcatca gccatggcgc ggtgaatacg ttcccgggcc     1380
ttgtacacac cgcccgtcaa gccatgaaag ccggggtgc ctgaagtccg tgaccgcgag     1440
ggtcggccta gggtaaaact ggtgattggg gctaagtcgt aacaaggtag cc             1492

<210> SEQ ID NO 4
<211> LENGTH: 1495
<212> TYPE: DNA
<213> ORGANISM: Barnesiella

<400> SEQUENCE: 4
gagagtttga tcctggctca ggatgaacgc tagcgacagg cctaacacat gcaagtcgag       60
gggcagcggg gaggtagcaa tacctttgcc ggcgaccggc gcacgggtga gtaacacgta      120
tgcaatccac ctgtaacagg gggataaccc ggagaaatcc ggactaatac ccatgatat      180 gggctctccg catggagggt ccattaaaga gagcaatctt ggttacagac gagcatgcgc      240
tccattagcc agttggcggg gtaacggccc accaaggcga cgatggatag ggttctgag      300 aggaaggtcc cccacattgg aactgagaca cggtccaaac tcctacggga ggcagcagtg      360
aggaatattg gtcaatggtc ggcagactga accagccaag tcgcgtgagg gaagacggcc      420 ctacggggttg taaacctctt ttgtcggaga gtaaagtgcg ctacgcgtag cgtattgcaa      480
gtatccgaag aaaaagcatc ggctaactcc gtgccagcag ccgcggtaat acggaggatg      540
cgagcgttat ccggatttat tgggtttaaa gggtgcgtag cggcacgcc aagtcagcgg      600 tgaaatttcc gggctcaacc cggactgtgc cgttgaaact ggcgagctag agtgcacaag      660
aggcaggcgg aatgcgtggt gtagcggtga aatgcataga tatcacgcag aaccccgatt      720
gcgaaggcag cctgctaggg tgcgacagac gctgaggcac gaaagcgtgg gtatcgaaca      780
ggattagata ccctggtagt ccacgcagta acgatgaat actaactgtt tgcgatacaa      840
tgtaagcggt acagcgaaag cgttaagtat tccacctggg gagtacgccg gcaacggtga      900
aactcaaagg aattgacggg ggcccgcaca agcggaggaa catgtggttt aattcgatga      960
tacgcgagga accttacccg ggctcaaacg caggggaat gccggtgaaa gtcggcagct     1020
agtaatagtc acctgcgagg tgctgcatgg ttgtcgtcag ctcgtgccgt gaggtgtcgg     1080
cttaagtgcc ataacgagcg caaccccttat cgacagttac taacgggtga agccgaggac     1140
tctgtcgaga ctgccggcgc aagccgcgag gaaggtgggg atgacgtcaa atcagcacgg     1200
```

```
cccttacgtc cggggcgaca cacgtgttac aatggcaggt acagaaggca gccagtcagc    1260
aatgacgcgc gaatcccgaa aacctgtctc agttcggatt ggagtctgca acccgactcc    1320
atgaagctgg attcgctagt aatcgcgcat cagccatggc gcggtgaata cgttcccggg    1380
ccttgtacac accgcccgtc aagccatgga agccgggagt acctgaagca tgcaaccgca    1440
aggagcgtac gaaggtaata ccggtaactg ggctaagtc gtaacaaggt agcca          1495
```

<210> SEQ ID NO 5
<211> LENGTH: 1511
<212> TYPE: DNA
<213> ORGANISM: Streptococcus

<400> SEQUENCE: 5

```
gagagtttga tcctggctca ggacgaacgc tggcggcgtg cctaatacat gcaagtaaaa     60
cgctgaagag aggagcttgc tcttcttgga tgagttgcga acgggtgagt aacgcgtagg    120
taacctgcct tgtagcgggg gataactatt ggaaacgata gctaataccg cataacaatg    180
gatgactcat gtcatttatt tgaaaggggc aaatgctcca ctacaagatg gacctgcgtt    240
gtattagcta gtaggtgagg taacggctca cctaggcgac gatacatagc cgacctgaga    300
gggtgatcgg ccacactggg actgagacac ggcccagact cctacgggag gcagcagtag    360
ggaatcttcg gcaatggggg caaccctgac cgagcaacgc cgcgtgagtg aagaaggttt    420
tcggatcgta aagctctgtt gtaagtcaag aacgagtgtg agagtggaaa gttcacactg    480
tgacggtagc ttaccagaaa gggacggcta actacgtgcc agcagccgcg gtaatacgta    540
ggtcccgagc gttgtccgga tttattgggc gtaaagcgag cgcaggcggt ttgataagtc    600
tgaagttaaa ggctgtggct caaccatagt tcgctttgga aactgtcaaa cttgagtgca    660
gaagggagag tggaattcc atgtgtagcg gtgaaatgcg tagatatatg gaggaacacc    720
ggtggcgaaa gcggctctct ggtctgtaac tgacgctgag gctcgaaagc gtggggagcg    780
aacaggatta gataccctgg tagtccacgc cgtaaacgat gagtgctagg tgttggatcc    840
tttccgggat tcagtgccgc agctaacgca ttaagcactc cgcctgggga gtacgaccgc    900
aaggttgaaa ctcaaaggaa ttgacggggg cccgcacaag cggtggagca tgtggtttaa    960
ttcgaagcaa cgcgaagaac cttaccaggt cttgacatcc cgatgctatt tctagagata   1020
gaaagttact tcggtacatc ggtgacaggt ggtgcatggt tgtcgtcagc tcgtgtcgtg   1080
agatgttggg ttaagtcccg caacgagcgc aaccctatt gttagttgcc atcattcagt    1140
tgggcactct agcgagactg ccggtaataa accggaggaa ggtggggatg acgtcaaatc   1200
atcatgcccc ttatgacctg ggctacacac gtgctacaat ggttggtaca acgagttgcg   1260
agtcggtgac ggcaagctaa tctcttaaag ccaatctcag ttcggattgt aggctgcaac   1320
tcgcctacat gaagtcggaa tcgctagtaa tcgcggatca gcacgccgcg gtgaatacgt   1380
tcccgggcct tgtacacacc gcccgtcaca ccacagagat ttgtaacacc cgaagtcggt   1440
gaggtaacct tttggagcca gccgcctaag gtgggataga tgattggggt gaagtcgtaa   1500
caaggtagcc g                                                        1511
```

<210> SEQ ID NO 6
<211> LENGTH: 1474
<212> TYPE: DNA
<213> ORGANISM: Ruminococcus

<400> SEQUENCE: 6

```
gagagtttga tcctggctca ggacgaacgc tggcggcacg cttaacacat gcaagtcgaa      60
cggagaatat cgaagcttgc tttgatattc ttagtggcgg acgggtgagt aacacgtgag     120
taacctgcct ctgagagtgg gatagcttct ggaaacggat ggtaataccg catgaaatca     180
tagtatcgca tggtacaatg atcaaagatt tatcgctcag agatggactc gcgtctgatt     240
agctagttgg taaggtaacg gcttaccaag gcgacgatca gtagccggac tgagaggttg     300
atcggccaca ttgggactga gacacggccc agactcctac gggaggcagc agtggggaat     360
attgcacaat gggggaaacc ctgatgcagc gatgccgcgt ggaggaagaa ggttttcgga     420
ttgtaaactc ctgttgaaga ggacgataat gacggtactc ttttagaaag ctccggctaa     480
ctacgtgcca gcagccgcgg taatacgtag ggagcgagcg ttgtccggaa ttactgggtg     540
taaagggagc gtaggcggga cggcaagtca gatgtgaaaa ctatgggctc aacccataga     600
ctgcatttga aactgttgtt cttgagtgag gtagaggtaa gcggaattcc tggtgtagcg     660
gtgaaatgcg tagagatcag gaggaacatc ggtggcgaag gcggcttact gggcctttac     720
tgacgctgag gctcgaaagc gtggggagca aacaggatta gataccctgg tagtccacgc     780
cgtaaacgat gattactagg tgtgggggga ctgaccccct tccgtgccgc agctaacacaa     840
taagtaatcc acctggggag tacggccgca aggttgaaac tcaaaggaat tgacggggc      900
ccgcacaagc agtggagtat gtggtttaat tcgaagcaac gcgaagaacc ttaccaggtc     960
ttgacatcga gtgacgtacc tagagatagg tattttcttc ggaacacaaa gacaggtggt    1020
gcatggttgt cgtcagctcg tgtcgtgaga tgttgggtta agtcccgcaa cgagcgcaac    1080
ccttaccatt agttgctacg caagagcact ctaatggac  tgccgttgac aaaacgagg     1140
aaggtgggga tgacgtcaaa tcatcatgcc ccttatgacc tgggctacac acgtactaca    1200
atggcaatat aacagaggga agcaatacag cgatgtggga caaatcccca aaaattgtcc    1260
cagttcagat tgcaggctgc aactcgcctg catgaagtcg gaattgctag taatcgcaga    1320
tcagcatgct gcggtgaata cgttcccggg ccttgtacac accgcccgtc acaccatggg    1380
agtcggtaac acccaaagcc ggtcgtctaa ccttcgggag gacgccgtct aaggtgggat    1440
tgatgactgg ggtgaagtcg taacaaggta accg                                1474

<210> SEQ ID NO 7
<211> LENGTH: 1467
<212> TYPE: DNA
<213> ORGANISM: Collinsella

<400> SEQUENCE: 7
agagtttgat cctggctcag gatgaacgct ggcggcgcgc ctaacacatg caagtcgaac      60
ggcacccctc tccggaggga agcgagtggc gaacggctga gtaacacgtg gagaacctgc     120
cccctccccc gggatagccg cccgaaagga cgggtaatac cggataccc  ggggtgccgc     180
atggcacccc ggctaaagcc ccgacgggag ggatggctc  gcggcccat  caggtagacg     240
gcggggtgac ggcccaccgt gccgacaacg ggtagccggg ttgagagacc gaccggccag     300
attgggactg agacacggcc cagactccta cgggaggcag cagtggggaa tcttgcgcaa     360
tgggggaac  cctgacgcag cgacgccgcg tgcgggacga aggccttcgg gtcgtaaacc     420
gctttcagca gggaagagtc aagactgtac ctgcagaaga agccccggct aactacgtgc     480
cagcagccgc ggtaatacgt aggggcgag  cgttatccgg attcattggg cgtaaagcgc     540
gcgtaggcgc cccggcaggc cggggtcga  agcgggggc  tcaaccccc  gaagcccccg     600
gaacctccgc ggcttgggtc cggtagggga gggtggaaca cccggtgtag cggtggaatg     660
```

```
cgcagatatc gggtggaaca ccggtggcga aggcggccct ctgggccgag accgacgctg    720
aggcgcgaaa gctgggggag cgaacaggat tagataccct ggtagtccca gccgtaaacg    780
atggacgcta ggtgtggggg gacgatcccc ccgtgccgca gccaacgcat taagcgtccc    840
gcctggggag tacggccgca aggctaaaac tcaaaggaat tgacggggc ccgcacaagc    900 agcggagcat gtggcttaat tcgaagcaac gcgaagaacc ttaccagggc ttgacatatg    960
ggtgaagcgg gggagacccc gtggccgaga ggagcccata caggtggtgc atggctgtcg   1020
tcagctcgtg tcgtgagatg ttgggttaag tcccgcaacg agcgcaaccc cgccgcgtg   1080 ttgccatcgg gtgatgccgg gaacccacgc gggaccgccg ccgtcaaggc ggaggagggc   1140
ggggacgacg tcaagtcatc atgcccctta tgccctgggc tgcacacgtg ctacaatggc   1200
cggtacagag ggatgccacc ccgcgagggg gagcggatcc cggaaagccg gccccagttc   1260
ggattggggg ctgcaacccg cccccatgaa gtcggagttg ctagtaatcg cggatcagca   1320
tgccgcggtg aatgcgttcc cgggccttgt acacaccgcc cgtcacacca cccgagtcgt   1380
ctgcacccga agtcgccggc ccaaccgcaa gggggaggc gccgaaggtg tggagggtga   1440 gggggggtgaa gtcgtaacaa ggtagcc                                      1467

<210> SEQ ID NO 8
<211> LENGTH: 1491
<212> TYPE: DNA
<213> ORGANISM: Bacteroides

<400> SEQUENCE: 8
gagagtttga tcctggctca ggatgaacgc tagctacagg cttaacacat gcaagtcgag     60
gggcagcggg attgaagctt gcttcaattg ccggcgaccg gcgcacgggt gagtaacgcg    120
tatccaacct tccgtacact cagggatagc cttcgaaag aaagattaat acctgatggt    180
atcttaagca cacatgtaat taagattaaa gatttatcgg tgtacgatgg ggatgcgttc    240
cattaggtag taggcggggt aacggcccac ctagccaacg atggataggg gttctgagag    300
gaaggtcccc cacattggaa ctgagacacg gtccaaactc ctacgggagg cagcagtgag    360
gaatattggt caatggacga gagtctgaac cagccaagta gcgtgaagga tgaaggtcct    420
acggattgta aacttctttt ataagggaat aaaccctccc acgtgtggga gcttgtatgt    480
accttatgaa taagcatcgg ctaactccgt gccagcagcc gcggtaatac ggaggatgcg    540
agcgttatcc ggatttattg ggtttaaagg gagcgcagac gggtcgttaa gtcagctgtg    600
aaagtttggg gctcaacctt aaaattgcag ttgatactgg cgtccttgag tgcggttgag    660
gtgtgcggaa ttcgtggtgt agcggtgaaa tgcttagata tcacgaagaa ctccgattgc    720
gaaggcagcg cactaatccg taactgacgt tcatgctcga agtgtgggt atcaaacagg    780 attagatacc ctggtagtcc acacggtaaa cgatggatac tcgctgttgg cgatatactg    840
tcagcggctt agcgaaagcg ttaagtatcc cacctgggga gtacgccggc aacggtgaaa    900
ctcaaaggaa ttgacgggg cccgcacaag cggaggaaca tgtggtttaa ttcgatgata    960
cgcgaggaac cttacccggg cttaaattgc aaaggaataa tctggaaaca ggttagtctt   1020
cggacctttg tgaaggtgct gcatggttgt cgtcagctcg tgccgtgagg tgtcggctta   1080
agtgccataa cgagcgcaac cctcgccgcc agttactaac agttaaagct gaggactctg   1140
gcgggactgc catcgtaaga tgtgaggaag gtgggggatga cgtcaaatca gcacggccct   1200
tacgtctggg gctacacacg tgttacaatg ggcggtacag aaggcagcta cctggcgaca   1260
```

```
ggatgccaat ccctaaagcc gctctcagtt cggactggag tctgcaaccc gactccacga    1320
agctggattc gctagtaatc gcgcatcagc cacggcgcgg tgaatacgtt cccgggcctt    1380
gtacacaccg cccgtcaagc catgaaagcc ggggtacctg aagtgcgta accgcaagga    1440 gcgccctagg gtaaaaccgg taattggggc taagtcgtaa caaggtagaa t             1491
```

<210> SEQ ID NO 9
<211> LENGTH: 1494
<212> TYPE: DNA
<213> ORGANISM: Dorea

<400> SEQUENCE: 9

```
gagagtttga tcctggctca ggatgaacgc tggcggcgtg cttaacacat gcaagtcgag    60
cgaagcactt aagtttgatt cttcggatga agacttttgt gactgagcgg cggacgggtg    120
agtaacgcgt gggtaaacctg cctcatacag ggggataaca gttagaaatg actgctaata    180
ccgtataaga ccacggtacc gcatggtaca gtgtaaaaa ctccggtggt atgagatgga    240
cccgcgtctg attaggtagt tggtggggta acggcctacc aagccgacga tcagtagccg    300
acctgagagg gtgaccggcc acattgggac tgagacacgg cccagactcc tacgggaggc    360
agcagtgggg aatattgcac aatggaggaa actctgatgc agcgacgccg cgtgaaggat    420
gaagtatttc ggtatgtaaa cttctatcag cagggaagaa aatgacggta cctgactaag    480
aagccccggc taactacgtg ccagcagccg cggtaatacg taggggggcaa gcgttatccg    540 gatttactgg gtgtaaaggg agcgtagacg gcacggcaag ccagatgtga aagcccgggg    600
ctcaaccccg ggactgcatt tggaactgct gagctagagt gtcggagagg caagtggaat    660
tcctagtgta gcggtgaaat gcgtagatat taggaggaac accagtggcg aaggcggctt    720
gctggacgat gactgacgtt gaggctcgaa agcgtgggga gcaaacagga ttagataccc    780
tggtagtcca cgccgtaaac gatgactgct aggtgtcggg tggcaaagcc attcggtgcc    840
gcagctaacg caataagcag tccacctggg gagtacgttc gcaagaatga aactcaaagg    900
aattgacggg gacccgcaca agcggtggag catgtggttt aattcgaagc aacgcgaaga    960
accttacctg atcttgacat cccgatgacc gcttcgtaat ggaagttttt cttcggaaca    1020
tcggtgacag gtggtgcatg gttgtcgtca gctcgtgtcg tgagatgttg ggttaagtcc    1080
cgcaacgagc gcaaccccta tcttcagtag ccagcattta aggtgggcac tctggagaga    1140
ctgccaggga taacctggag gaaggtgggg atgacgtcaa atcatcatgc ccttatgac    1200 cagggctaca cacgtgctac aatggcgtaa acaaagagaa gcgaactcgc gagggtaagc    1260
aaatctcaaa ataacgtct cagttcggat tgtagtctgc aactcgacta catgaagctg    1320
gaatcgctag taatcgcaga tcagaatgct gcggtgaata cgttcccggg tcttgtacac    1380
accgcccgtc acaccatggg agtcagtaac gcccgaagtc agtgacccaa ccgtaaggag    1440
ggagctgccg aaggtgggac cgataactgg ggtgaagtcg taacaaggta gccg         1494
```

<210> SEQ ID NO 10
<211> LENGTH: 1490
<212> TYPE: DNA
<213> ORGANISM: Alistipes

<400> SEQUENCE: 10

```
tagagtttga tcctggctca ggatgaacgc tagcggcagg cttaacacat gcaagtcgag    60
gggcagcata atggatagca atatctatgg tggcgaccgg cgcacgggtg cgtaacgcgt    120
atgcaaccta cctttaacag ggggataaca ctgagaaatt ggtactaata ccccataata    180
```

```
tcatagaagg catcttttat ggttgaaaat tccgatggtt agagatgggc atgcgttgta        240
ttagctagtt ggtggggtaa cggctcacca aggcgacgat acataggggg actgagaggt        300 taaccccca cactggtact gagacacgga ccagactcct acgggaggca gcagtgagga         360
atattggtca atggacgcaa gtctgaacca gccatgccgc gtgcaggatg acggctctat        420
gagttgtaaa ctgcttttgt acgagggtaa acgcagatac gtgtatctgt ctgaaagtat        480
cgtacgaata aggatcggct aactccgtgc cagcagccgc ggtaatacgg aggattcaag        540
cgttatccgg atttattggg tttaaagggt gcgtaggcgg tttgataagt tagaggtgaa        600
atttcggggc tcaaccctga acgtgcctct aatactgttg agctagagag tagttgcggt        660
aggcggaatg tatggtgtag cggtgaaatg cttagagatc atacagaaca ccgattgcga        720
aggcagctta ccaaactata tctgacgttg aggcacgaaa gcgtggggag caaacaggat        780 tagatacct ggtagtccac gcagtaaacg atgataactc gttgtcggcg atacacagtc        840
ggtgactaag cggaagcgat aagttatcca cctggggagt acgttcgcaa gaatgaaact        900
caaaggaatt gacgggggcc cgcacaagcg aggaacatg tggtttaatt cgatgatacg        960
cgaggaacct tacccgggct tgaaagttag cgacgattct tgaaagagga tttcccttcg       1020
gggcgcgaaa ctaggtgctg catggttgtc gtcagctcgt gccgtgaggt gtcgggttaa       1080
gtcccataac gagcgcaacc cctaccgtta gttgccatca ggtgaagctg ggcactctgg       1140
cgggactgcc ggtgtaagcc gagaggaagg tggggatgac gtcaaatcag cacggccctt       1200
acgtccgggg ctacacacgt gttacaatgg taggtacaga gggcagctac ccagcgatgg       1260
gatgcgaatc tcgaaagcct atctcagttc ggattggagg ctgaaacccg cctccatgaa       1320
gttggattcg ctagtaatcg cgcatcagcc atggcgcggt gaatacgttc ccgggccttg       1380
tacacaccgc ccgtcaagcc atgggagccg ggggtgcctg aagttcgtga ccgcaaggag       1440
cgacctaggg caaaactggt gactgggact aagtcgtaac aaggtagccg                  1490
```

<210> SEQ ID NO 11
<211> LENGTH: 1486
<212> TYPE: DNA
<213> ORGANISM: Butyricimonas

<400> SEQUENCE: 11

```
gagagtttga tcctggctca ggatgaacgc tagcgacagg cttaacacat gcaagtcgag         60
gggcagcatg aggtagcaat accttgatgg cgaccggcgc acgggtgagt aacacgtgtg        120
caaccaacct cgtgccggga gataacccgc ggaaacgtgg actaacatcc catggtactt        180
caccttcgca tgaaggtgat tttaaaagta atggcacgag acgggcacgc gcggcattag        240
gtagttggcg gggtaacggc ccaccaagcc gacgatgcct aggggttctg agaggaaggt        300
cccccacact ggaactgaga cacggtccag actcctacgg gaggcagcag tgaggaatat        360
tggtcaatgg gcgaagcct gaaccagcca agtcgcgtga gggaagaatg gtctatggcc        420
tgtaaacctc ttttgaaagg gaagaataag tggcacgcgt gccatgatgc cagtaccttt        480
cgaataagca tcggctaact ccgtgccagc agccgcggta acacgggga tgcgagcgtt        540 atccggattt attgggttta aagggcgcgt aggcggatc caagtcagc ggtaaaagac        600 tgcagctaaa ctgtagcacg ccgttgaaac tggtgaccta gagagaagtc gagggaggcg        660
gaacaagtga agtagcggtg gaatgcttag atatcacttg gaacccgat agcgaaggca        720 gcttcccagt ctttgtctga cgctgatgcg cgagagcgtg ggtagcgaac aggattagat        780
```

| | |
|---|---|
| accctggtag tccacgccgt aaacgatgct cactggatct tggcgataca cggtcagggt | 840 |
| tcaagcgaaa gtattaagtg agccacctgg ggagtacgtc ggcaacgatg aaactcaaag | 900 |
| gaattgacgg gggcccgcac aagcggagga acatgtggtt taattcgatg atacgcgagg | 960 |
| aaccttacct gggtttaaat gtagagtgca tgaggtggaa acacttcttc ccttcggggc | 1020 |
| tctttacaag gtgctgcatg gttgtcgtca gctcgtgccg tgaggtgtcg ggttaagtcc | 1080 |
| cataacgagc gcaaccccta tcgatagttg ccaccgggtc aagccgggca ctctatcgag | 1140 |
| actgccaccg taaggtgcga ggaaggcggg gatgacgtca aatcagcacg gcccttacat | 1200 |
| ccagggctac acacgtgtta caatggccgg tacagagggc cgccacgggg tgacccggcg | 1260 |
| ctaatctcta aagccggtcg tagttcggac tggagtctgc aacccgactc cacgaagttg | 1320 |
| gattcgctag taatcgcgca tcagccatgg cgcggtgaat acgttcccgg gccttgtaca | 1380 |
| caccgcccgt caagccatgg gagccgggag tacctgaaga tcgtgaccgc gaggaacggg | 1440 |
| ctagggtaat actggtaact ggggctaagt cgtaacaagg tagccg | 1486 |

<210> SEQ ID NO 12
<211> LENGTH: 1527
<212> TYPE: DNA
<213> ORGANISM: Veillonella

<400> SEQUENCE: 12

| | |
|---|---|
| gagagtttga tcctggctca ggacgaacgc tggcggcgtg cttaacacat gcaagtcgaa | 60 |
| cgaagagcga tggaagcttg cttctatcaa tcttagtggc gaacgggtga gtaacgcgta | 120 |
| atcagcctgc ccttcagagg gggacaacag ttggaaacga ctgctaatac cgcatacgat | 180 |
| ctaatctcgg catcgaggaa agatgaaagg tggcctctat gtataagcta tcactgaagg | 240 |
| aggggattgc gtctgattag ctagttggag gggtaacggc ccaccaaggc gatgatcagt | 300 |
| agccggtctg agaggatgaa cggccacatt gggactgaga cacggcccag actcctacgg | 360 |
| gaggcagcag tggggaatct tccgcaatgg acgaaagtct gacggagcaa cgccgcgtga | 420 |
| gtgatgacgg ccttcgggtt gtaaagctct gttaatcggg acgaaaggcc ttcttgcgaa | 480 |
| cagttagaag gattgacggt accggaatag aaagccacgg ctaactacgt gccagcagcc | 540 |
| gcggtaatac gtaggtggca agcgttgtcc ggaattattg ggcgtaaagc gcgcgcaggc | 600 |
| ggatcagtca gtctgtctta aaagttcggg gcttaacccc gtgatgggat ggaaactgct | 660 |
| gatctagagt atcggagagg aaagtggaat tcctagtgta gcggtgaaat gcgtagatat | 720 |
| taggaagaac accagtggcg aaggcgactt tctggacgaa aactgacgct gaggcgcgaa | 780 |
| agccagggga gcgaacggga ttagataccc cggtagtcct ggccgtaaac gatgggtact | 840 |
| aggtgtagga ggtatcgacc ccttctgtgc cggagttaac gcaataagta ccccgcctgg | 900 |
| ggagtacgac cgcaaggttg aaactcaaag gaattgacgg gggcccgcac aagcggtgga | 960 |
| gtatgtggtt taattcgacg caacgcgaag aaccttacca ggtcttgaca ttgatggaca | 1020 |
| gaactagaga tagttcctct tcttcggaag ccagaaaaca ggtggtgcac ggttgtcgtc | 1080 |
| agctcgtgtc gtgagatgtt gggttaagtc ccgcaacgag cgcagcccct atcttatgtt | 1140 |
| gccagcacgt aatggtggga actcatgaga gactgccgca gacaatgcgg aggaaggcgg | 1200 |
| ggatgacgtc aaatcatcat gccccttatg acctgggcta cacacgtact acaatgggag | 1260 |
| ttaatagacg gaagcgagat cgcgagatgg agcaaacccg agaaacactc tctcagttcg | 1320 |
| gatcgtaggc tgcaactcgc ctacgtgaag tcggaatcgc tagtaatcgc aggtcagcat | 1380 |
| actgcggtga atacgttccc gggccttgta cacaccgccc gtcacaccac gaaagtcgga | 1440 |

```
                  agtgcccaaa gccggtgggg taaccttcgg gagccagccg tctaaggtaa agtcgatgat    1500
tggggtgaag tcgtaacaag gtagccg                                        1527

<210> SEQ ID NO 13
<211> LENGTH: 1503
<212> TYPE: DNA
<213> ORGANISM: Klebsiella

<400> SEQUENCE: 13
gagagtttga tcctggctca gattgaacgc tggcggcagg cctaacacat gcaagtcgag      60
cggtagcaca gagagcttgc tctcgggtga cgagcggcgg acgggtgagt aatgtctggg     120
aaactgcctg atggaggggg ataactactg gaaacggtag ctaataccgc ataatgtcgc     180
aagaccaaag tgggggacct tcgggcctca tgccatcaga tgtgcccaga tgggattagc     240
tagtaggtgg ggtaacggct cacctaggcg acgatcccta gctggtctga gaggatgacc     300
agccacactg gaactgagac acggtccaga ctcctacggg aggcagcagt ggggaatatt     360
gcacaatggg cgcaagcctg atgcagccat gccgcgtgtg tgaagaaggc cttcgggttg     420
taaagcactt tcagcgggga ggaaggcgtt aaggttaata accttggcga ttgacgttac     480
ccgcagaaga agcaccggct aactccgtgc cagcagccgc ggtaatacgg agggtgcaag     540
cgttaatcgg aattactggg cgtaaagcgc acgcaggcgg tctgtcaagt cggatgtgaa     600
atccccgggc tcaacctggg aactgcattc gaaactggca ggctagagtc ttgtagaggg     660
gggtagaatt ccaggtgtag cggtgaaatg cgtagagatc tggaggaata ccggtggcga     720
aggcggcccc ctggacaaag actgacgctc aggtgcgaaa gcgtgggag caaacaggat     780 tagataccct ggtagtccac gccgtaaacg atgtcgattt ggaggttgtg cccttgaggc     840
gtggcttccg gagctaacgc gttaaatcga ccgcctggg agtacggccg caaggttaaa     900
actcaaatga attgacgggg gcccgcacaa gcggtggagc atgtggttta attcgatgca     960
acgcgaagaa ccttacctgg tcttgacatc cacagaactt agcagagatg ctttggtgcc    1020
ttcgggaact gtgagacagg tgctgcatgg ctgtcgtcag ctcgtgttgt gaaatgttgg    1080
gttaagtccc gcaacgagcg caacccttat cctttgttgc cagcggtccg gccgggaact    1140
caaaggagac tgccagtgat aaactggagg aaggtgggga tgacgtcaag tcatcatggc    1200
ccttacgacc agggctacac acgtgctaca atggcatata caagagaag cgacctcgcg    1260 agagcaagcg gacctcataa agtatgtcgt agtccggatt ggagtctgca actcgactcc    1320
atgaagtcgg aatcgctagt aatcgtagat cagaatgcta cggtgaatac gttcccgggc    1380
cttgtacaca ccgcccgtca caccatggga gtgggttgca aaagaagtag gtagcttaac    1440
cttcgggagg cgcttacca ctttgtgatt catgactggg gtgaagtcgt aacaaggtag    1500
ccg                                                                 1503

<210> SEQ ID NO 14
<211> LENGTH: 1513
<212> TYPE: DNA
<213> ORGANISM: Desulfovibrio

<400> SEQUENCE: 14
gagagtttga tcctggctca gattgaacgc tggcggcgtg cttaacacat gcaagtcgta      60
cgcgaaaggg acttcggtcc cgagtaaagt ggcgcacggg tgagtaacac gtggataatc     120
tgcctctatg atggggataa cagttggaaa cgactgctaa taccgaatat gctcatgatg     180
```

| | |
|---|---|
| aactttatga ggaaaggtgg cctctgcttg caagctatcg catagagatg agtccgcgtc | 240 |
| ccattagcta gttggtgggg taacggccta ccaaggcaac gatgggtagc cgatctgaga | 300 |
| ggatgatcgg ccacactgga actgaaacac ggtccagact cctacgggag gcagcagtgg | 360 |
| ggaatattgc gcaatgggcg aaagcctgac gcagcgacgc cgcgtgaggg atgaaggtct | 420 |
| tcggatcgta aacctctgtc agaagggaag aaactagggt gctctaatca tcatcctact | 480 |
| gacggtacct tcaaaggaag caccggctaa ctccgtgcca gcagccgcgg taatacggag | 540 |
| ggtgcaagcg ttaatcggaa tcactgggcg taaagcgcac gtaggctgtt atgtaagtca | 600 |
| ggggtgaaat cccacggctc aaccgtggaa ctgcccttga tactgcacga cttgaatccg | 660 |
| ggagagggtg gcggaattcc aggtgtagga gtgaaatccg tagatatctg gaggaacatc | 720 |
| agtggcgaag gcggccacct ggaccggtat tgacgctgag gtgcgaaagc gtggggagca | 780 |
| aacaggatta gataccctgg tagtccacgc cgtaaacgat ggatgctgga tgtcgggatg | 840 |
| tatgtctcgg tgtcgtagtt aacgcgttaa gcatcccgcc tggggagtac ggtcgcaagg | 900 |
| ctgaaactca agaaattga cggggccccg cacaagcggt ggagtatgtg gtttaattcg | 960 |
| atgcaacgcg aagaaccta cctaggtttg acatctgggg aaccctcccg aaaaggaggg | 1020 |
| gtgcccttcg gggagcccca agacaggtgc tgcatggctg tcgtcagctc gtgtcgtgag | 1080 |
| atgtttgggtt aagtcccgca acgagcgcaa cccctatgca tagttgccag caagtgatgt | 1140 |
| tgggcactct atgcagactg cccggttaa ccggaggaa ggtggggacg acgtcaagtc | 1200 |
| atcatggccc ttacacctag gctacacac gtactacaat ggcacgcaca aagggcagcg | 1260 |
| ataccgtgag gtggagccaa tcccaaaaaa cgtgtcccag tccggattgc agtctgcaac | 1320 |
| tcgactgcat gaagtcggaa tcgctagtaa ttcgaggtca gcatactcgg gtgaatgcgt | 1380 |
| tcccgggcct tgtacacacc gcccgtcaca ccacgaaagt cggttttacc cgaagccggt | 1440 |
| gagccaacta gcaatagagg cagccgtcta cggtagggcc gatgattggg gtgaagtcgt | 1500 |
| aacaaggtaa ccg | 1513 |

<210> SEQ ID NO 15
<211> LENGTH: 1495
<212> TYPE: DNA
<213> ORGANISM: Anaerostipes

<400> SEQUENCE: 15

| | |
|---|---|
| agagtttgat cctggctcag gatgaacgct ggcggcgtgc ttaacacatg caagtcgaac | 60 |
| gaagcattta ggattgaagt tttcggatgg atttcctata tgactgagtg gcggacgggt | 120 |
| gagtaacgcg tgggggaacct accctataca gggggataac agctggaaac ggctgctaat | 180 |
| accgcataag cgcacagaat cgcatgattc agtgtgaaaa gccctggcag tataggatgg | 240 |
| tcccgcgtct gattagctgg ttggtgaggt aacggctcac caaggcgacg atcagtagcc | 300 |
| ggcttgagag agtgaacggc cacattggga ctgagacacg gcccaaactc ctacgggagg | 360 |
| cagcagtggg gaatattgca caatggggga accctgatg cagcggcgcc gcgtgagtga | 420 |
| agaagtattt cggtatgtaa agctctatca gcagggaaga aaacagacgg tacctgacta | 480 |
| agaagccccg gctaactacg tgccagcagc cgcggtaata cgtaggggc aagcgttatc | 540 |
| cggaattact gggtgtaaag ggtgcgtagg tggcatggta agtcagaagt gaaagcccgg | 600 |
| ggcttaaccc cggggactgct tttgaaactg tcatgctgga gtgcaggaga ggtaagcgga | 660 |
| attcctagtg tagcggtgaa atgcgtagat attaggagga acaccagtgg cgaaggcggc | 720 |
| ttactggact gtcactgaca ctgatgcacg aaagcgtggg gagcaaacag gattagatac | 780 |

-continued

```
cctggtagtc cacgccctaa acgatgaata ctaggtgtcg gggccgtaga ggcttcggtg    840
ccgcagcaaa cgcagtaagt attccacctg gggagtacgt tcgcaagaat gaaactcaaa    900
ggaattgacg gggacccgca caagcggtgg agcatgtggt ttaattcgaa gcaacgcgaa    960
gaaccttacc tggtcttgac atcccaatga ccgaaccttta accggttttt tctttcgaga   1020
cattggagac aggtggtgca tggttgtcgt cagctcgtgt cgtgagatgt tgggttaagt   1080
cccgcaacga gcgcaacccc tatctttagt agcccgcatt acgatgggc actctagaga     1140 gactgccagg gataacctgg aggaaggtgg ggacgacgtc aaatcatcat gccccttatg   1200
gccagggcta cacacgtgct acaatggcgt aaacaaaggg aagcgaagtc gtgaggcgaa   1260
gcaaatccca gaaataacgt ctcagttcgg attgtagtct gcaactcgac tacatgaagc   1320
tggaatcgct agtaatcgtg aatcagaatg tcacggtgaa tacgttcccg ggtcttgtac   1380
acaccgcccg tcacaccatg ggagtcagta acgcccgaag tcagtgaccc aaccgcaagg   1440
agggagctgc cgaaggtggg accgataact ggggtgaagt cgtaacaagg tagcc         1495
```

```
<210> SEQ ID NO 16
<211> LENGTH: 1501
<212> TYPE: DNA
<213> ORGANISM: Haemophilus

<400> SEQUENCE: 16
```

```
agagtttgat cctggctcag attgaacgct ggcggcaggc ttaacacatg caagtcgaac     60
ggtaacagga agaagcttgc ttctttgctg acgagtggcg gacgggtgag taatgcttgg    120
gaatctggct tatggagggg gataaactacg ggaaactgta gctaataccg cgtaatatcg    180
agagattaaa gggtgggacc gcaaggccac ctgccatgag atgagcccaa gtgggattag    240
gtagttggtg aggtaaaggc tcaccaagcc gacgatctct agctggtctg agaggatgac    300
cagccacact ggaactgaga cacggtccag actcctacgg gaggcagcag tggggaatat    360
tgcacaatgg ggggaaccct gatgcagcca tgccgcgtga atgaagaagg ccttcgggtt    420
gtaaagttct ttcggtagcg aggaaggcat ttagtttaat agactagatg attgacgtta    480
actacagaag aagcaccggc taactccgtg ccagcagccg cggtaatacg ggggtgcga    540 gcgttaatcg gaataactgg gcgtaaaggg cacgcaggcg gtgacttaag tgagatgtga    600
aagcccgggg cttaacctgg gaattgcatt tcatactggg tcgctagagt actttaggga   660
ggggtagaat tccacgtgta gcggtgaaat gcgtagagat gtggaggaat accgaaggcg   720
aaggcagccc cttgggaatg tactgacgct catgtgcgaa agcgtgggga gcaaacagga    780
ttagataccc tggtagtcca cgctgtaaac gatgtcgatt tggggggttgg gctttaagct    840 tggcgcccgt agctaacgtg ataaatcgac cgcctgggga gtacgccgc aaggttaaaa    900 ctcaaatgaa ttgacggggg cccgcacaag cggtggagca tgtggtttaa ttcgatgcaa    960
cgcgaagaac cttacctact cttgacatcc agagaacttt tcagagatgg attggtgcct   1020
tcgggaactc tgagacaggt gctgcatggc tgtcgtcagc tcgtgttgtg aaatgttggg   1080
ttaagtcccg caacgagcgc aaccttatc ctttgttgcc agcgattagg tcgggaactc    1140
aaaggagact gccggtgata aaccggagga aggtgggat gacgtcaagt catcatggcc    1200
cttacgagta gggctacaca cgtgctacaa tggcgtatac agagggaagc aatcctgcga   1260
gggggagcaa atctcacaaa gtacgtctaa gtccggattg gagtctgcaa ctcgactcca    1320
tgaagtcgga atcgctagta atcgcaaatc agaatgttgc ggtgaatacg ttcccgggcc    1380
```

```
ttgtacacac cgcccgtcac accatgggag tgggttgtac cagaagtaga tagcttaacc   1440 ttcgggggg  cgtttaccac ggtatgattc atgactgggg tgaagtcgta acaaggtagc   1500
c                                                                   1501

<210> SEQ ID NO 17
<211> LENGTH: 1498
<212> TYPE: DNA
<213> ORGANISM: Sutterella

<400> SEQUENCE: 17
gagagtttga tcctggctca gattgaacgc tggcggcatg ctttacacat gcaagtcgaa     60
cggcagcaca gggagcttgc tcccgggtgg cgagtggcgc acgggtgagt aatacatcgg    120
aacgtgtcct gttgtggggg ataactgctc gaaagggtgg ctaataccgc atgagacctg    180
agggtgaaag cggggatcg  caagacctcg cgcaattgga gcggccgatg cccgattagc    240
tagttggtga ggtaaaggct caccaaggcg acgatcggta gctggtctga gaggacgacc    300
agccacactg ggactgagac acggcccaga ctcctacggg aggcagcagt ggggaatttt    360
ggacaatggg ggcaaccctg atccagccat gccgcgtgca ggatgaaggc cttcgggttg    420
taaactgctt ttgtcaggga cgaaaaggat cgtgataata ccatggtctg ctgacggtac    480
ctgaagaata agcaccggct aactacgtgc cagcagccgc ggtaatacgt agggtgcaag    540
cgttaatcgg aattactggg cgtaaagcgt gcgcaggcgg ttctgtaaga cagatgtgaa    600
atccccgggc tcaacctggg aattgcattt gtgactgcag gactagagtt catcagaggg    660
gggtggaatt ccaagtgtag cagtgaaatg cgtagatatt tggaagaaca ccaatggcga    720
aggcagcccc ctgggatgcg actgacgctc atgcacgaaa gcgtggggag caaacaggat    780
tagataccct ggtagtccac gccctaaacg atgtctactg gttgttgggg tttattaacc    840
ttggtaacga agctaacgcg tgaagtagac cgcctgggga gtacggtcgc aagattaaaa    900
ctcaaaggaa ttgacgggga cccgcacaag cggtgaatga tgtggattaa ttcgatgcaa    960
cgcgaaaaac cttacctagc cttgacatgc caggaatcct gaagagattc gggagtgccc   1020
gcaagggaat ctggacacag gtgctgcatg gctgtcgtca gctcgtgtcg tgagatgttg   1080
ggttaagtcc cgcaacgagc gcaacccttg tcactagttg ctacgcaaga gcactctagt   1140
gagactgccg gtgacaaacc ggaggaaggt ggggatgacg tcaagtcctc atggccctta   1200
tggctagggc ctcacacgtc atacaatggt cggaacagag ggcagcgaag ccgcgaggtg   1260
gagcaaatcc cagaaaaccg atcgtagtcc ggattgcagt ctgcaactcg actgcatgaa   1320
gtcggaatcg ctagtaatcg cggatcagca tgccgcggtg aatacgttcc cgggtcttgt   1380
acacaccgcc cgtcacacca tgggagtggg gttcaccaga agacgtttgt ttaaccgcaa   1440
ggaggacggc gtccacggtg ggcttcatga ctggggtgaa gtcgtaacaa ggtagccg    1498

<210> SEQ ID NO 18
<211> LENGTH: 1535
<212> TYPE: DNA
<213> ORGANISM: Lactobacillus

<400> SEQUENCE: 18
tagagtttga tcctggctca ggacgaacgc tggcggcgtg cctaatacat gcaagtcgag     60
cgagcttgcc tagatgaatt tggtgcttgc accaaatgaa actagataca agcgagcggc    120
ggacgggtga gtaacacgtg gtaacctgcc caagagact gggataacac ctggaaacag    180
atgctaatac cggataacaa cactagacgc atgtctagag tttaaaagat ggttctgcta    240
```

-continued

```
tcactcttgg atggacctgc ggtgcattag ctagttggta aggtaacggc ttaccaaggc    300
aatgatgcat agccgagttg agagactgat cggccacatt gggactgaga cacggcccaa    360
actcctacgg gaggcagcag tagggaatct tccacaatgg acgcaagtct gatggagcaa    420
cgccgcgtga gtgaagaagg gtttcggctc gtaaagctct gttggtagtg aagaaagata    480
gaggtagtaa ctggccttta tttgacggta attacttaga aagtcacggc taactacgtg    540
ccagcagccg cggtaatacg taggtggcaa gcgttgtccg gatttattgg gcgtaaagcg    600
agtgcaggcg gttcaataag tctgatgtga aagccttcgg ctcaaccgga gaattgcatc    660
agaaactgtt gaacttgagt gcagaagagg agagtggaac tccatgtgta gcggtggaat    720
gcgtagatat atggaagaac accagtggcg aaggcggctc tctggtctgc aactgacgct    780
gaggctcgaa agcatgggta gcgaacagga ttagataccc tggtagtcca tgccgtaaac    840
gatgagtgct aagtgttggg aggtttccgc ctctcagtgc tgcagctaac gcattaagca    900
ctccgcctgg ggagtacgac cgcaaggttg aaactcaaag gaattgacgg gggcccgcac    960
aagcggtgga gcatgtggtt taattcgaag caacgcgaag aaccttacca ggtcttgaca   1020
tccagtgcaa acctaagaga ttaggagttc ccttcgggga cgctgagaca ggtggtgcat   1080
ggctgccgtc agctcgtgtc gtgagatgtt gggttaagtc ccgcaacgag cgcaacccet   1140 gtcattagtt gccatcatta agttgggcac tctaatgaga ctgccggtga caaaccggag   1200
gaaggtgggg atgacgtcaa gtcatcatgc cccttatgac ctgggctaca cacgtgctac   1260
aatggacggt acaacgagaa gcgaacctgc gaaggcaagc ggatctctga agccgttct    1320 cagttcggac tgtaggctgc aactcgccta cacgaagctg gaatcgctag taatcgcgga   1380
tcagcacgcc gcggtgaata cgttcccggg ccttgtacac accgcccgtc acaccatgag   1440
agtctgtaac acccaaagcc ggtgggataa cctttatagg agtcagccgt ctaaggtagg   1500
acagatgatt agggtgaagt cgtaacaagg taacc                              1535
```

<210> SEQ ID NO 19
<211> LENGTH: 1302
<212> TYPE: DNA
<213> ORGANISM: Pseudomonas

<400> SEQUENCE: 19

```
tgcaagtcga gcggatgagg ggtgcttgca ctctgattca gcggcggacg ggtgagtaat     60
gcctaggaat ctgcccgata gtgggggaca acgtttcgaa aggaacgcta ataccgcata    120
cgtcctacgg gagaaagtgg gggatcttcg gacctcacgc tatcggataa gcctaggtcg    180
gattagctag ttggtgaggt aatggctcac caaggcgacg atccgtaact ggtctgagag    240
gatgatcagt cacactggaa ctgagacacg gtccagactc ctacgggagg cagcagtggg    300
gaatattgga caatgggcga aagcctgatc cagccatgcc gcgtgtgtga agaaggtctt    360
cggattgtaa agcactttaa gttggagga agggctgtcg ctaataccc tgcagttttg     420 acgttaccaa cagaataagc accggctaac ttcgtgccag cagccgcggt aatacgaagg    480
gtgcaagcgt taatcggaat tactgggcgt aaagcgcgcg taggtggttc agcaagttgg    540
atgtgaaagc cccgggctca acctgggaac tgcatccaaa actactgagc tagagtacgg    600
tagagggtgg tggaatttcc tgtgtagcgg tgaaatgcgt agatatagga aggaacacca    660
gtggcgaagg cgaccacctg gactgatact gacactgagg tgcgaaagcg tgaggagcaa    720
acaggattag ataccctggt agtccacgcc gtaaacgatg tcaactagct gttgggttcc    780
```

```
ttgagaactt agtagcgaag ctaacgcgat aagttgaccg cctggggagt acggccgcaa    840
ggttaaaact caaatgaatt gacggggggcc cgcacaagcg gtggagcatg tggtttaatt    900
cgaagcaacg cgaagaacct tacctggcct tgacatgctg agaactttcc agagatggat    960
tggtgccttc gggaactcag acacaggtgc tgcatggctg tcgtcagctc gtgtcgtgag    1020
atgttgggtt aagtcccgta acgagcgcaa cccttgtcct tagttaccag cacgttatgg    1080
tgggcactct aaggagactg ccggtgacaa accggaggaa ggtggggatg acgtcaagtc    1140
atcatggccc ttacggccag ggctacacac gtgctacaat ggtcggtaca gagggttgcc    1200
aagccgcgag gcggagctaa tctcacaaaa ccgatcgtag tccggatcgc agtctgcaac    1260
tcgactgcgt gaagtcggaa tcgctagtaa tcgtgaatca ga                       1302

<210> SEQ ID NO 20
<211> LENGTH: 1298
<212> TYPE: DNA
<213> ORGANISM: Acidovorax

<400> SEQUENCE: 20
tgcaagtcga acggtaacag gccgcaaggt gctgacgagt ggcgaacggg tgagtaatgc    60
atcggaacgt gcccagtcgt gcgggataac gaagcgaaag ctttgctaat accgcatacg    120
atctcaggat gaaagcaggg gaccgcaagg ccttgcgctc acggagcggc cgatggcaga    180
ttaggtagtt ggtgggataa aagcttacca agccgacgat ctgtagctgg tctgagagga    240
cgaccagcca cactgggacc gagacacggc ccagactcct acgggaggca gcagtgggga    300
attttggaca atgggcgcaa gcctgatcca gccatgccgc gtgcaggatg aaggccttcg    360
ggttgtaaac tgcttttgta cggaacgaaa agactctggt taatacctgg ggtccatgac    420
ggtaccgtaa gaataagcac cggctaacta cgtgccagca gccgcggtaa tacgtagggt    480
gcgagcgtta atcggaatta ctgggcgtaa agcgtgcgca ggcggttatg taagacagat    540
gtgaaatccc cgggctcaac ctgggaactg catttgtgac tgcatagcta gagtacggca    600
gagggggatg gaattccgcg tgtagcagtg aaatgcgtag atatgcggag gaacaccgat    660
ggcgaaggca atcccctggg cctgtactga cgctcatgca cgaaagcgtg gggagcaaac    720
aggattagat accctggtag tccacgccct aaacgatgtc aactggttgt tgggtcttca    780
ctgacccagt aacgaagcta acgcgtgaag ttgaccgcct ggggagtacg gccgcaaggt    840
tgaaactcaa aggaattgac ggggacccgc acaagcggtg gatgatgtgg tttaattcga    900
tgcaacgcga aaaaccttac ccacctttga catgtacgga atcctttaga gatagaggag    960
tgctcgaaag agagccgtaa cacaggtgct gcatggctgt cgtcagctcg tgtcgtgaga    1020
tgttgggtta ggtcccgcaa cgagcgcaac ccttgtcatt agttgctaca ttcagtttggg    1080 cactctaatg agactgccgg tgacaaaccg gaggaaggtg gggatgacgt caagtcctca    1140
tggcccttat aggtggggct acacacgtca tacaatggct ggtacagagg ctgccaacc    1200 cgcgaggggg agccaatccc ataaagccag tcgtagtccg gatcgcagtc tgcaactcga    1260
ctgcgtgaag tcggaatcgc tagtaatcgc ggatcaga                           1298

<210> SEQ ID NO 21
<211> LENGTH: 1306
<212> TYPE: DNA
<213> ORGANISM: Thauera

<400> SEQUENCE: 21
catgcaagtc gaacggcagc gggggcttcg gcctgccggc gagtggcgaa cgggtgagta    60
```

```
atgcatcgga acgtgcccat gtcgtggggg ataacgtagc gaaagctacg ctaataccgc      120
atacgccctg aggggggaaag cgggggattc ttcggaacct cgcgcgattg gagcggccga     180
tgtcggatta gctagtaggt gaggtaaagg ctcacctagg cgacgatccg tagcgggtct      240
gagaggatga tccgccacac tgggactgag acacggccca gactcctacg ggaggcagca     300
gtggggaatt ttggacaatg ggcgcaagcc tgatccagcc atgccgcgtg agtgaagaag     360
gccttcgggt tgtaaagctc tttcggccgg gaagaaatcg tggtctctaa cataggccat    420
ggatgacggt accggactaa gaagcaccgg ctaactacgt gccagcagcc gcggtaatac   480
gtagggtgcg agcgttaatc ggaattactg ggcgtaaagc gtgcgcaggc ggttttgtaa    540
gacagatgtg aaatccccgg gcttaacctg gaactgcgt tgtgactgc aaggctagag      600 tacggcagag gggggtggaa ttcctggtgt agcagtgaaa tgcgtagaga tcaggaggaa    660
caccgatggc gaaggcagcc cctgggcct gtactgacgc tcatgcacga aagcgtgggg   720
agcaaacagg attagatacc ctggtagtcc acgccctaaa cgatgtcgac tagtcgttcg    780
gagcagcaat gcactgagtg acgcagctaa cgcgtgaagt cgaccgcctg ggagtacgg    840 ccgcaaggtt aaaactcaaa ggaattgacg gggacccgca caagcggtgg atgatgtgga   900
ttaattcgat gcaacgcgaa aaaccttacc tacccttgac atgtctggaa ccttgctgag   960
aggcgagggt gccttcggga gccagaacac aggtgctgca tggctgtcgt cagctcgtgt  1020
cgtgagatgt tgggttaagt cccgcaacga gcgcaaccct tgtcactagt tgccatcatt  1080
tggttgggca ctctagtgag actgccggtg acaaaccgga ggaaggtggg gatgacgtca  1140
agtcctcatg gcccttatgg gtagggcttc acacgtcata caatggtcgg tacagagggt  1200
tgccaagccg cgaggtggag ccaatcccctt aaagccgatc gtagtccgga tcgtagtctg  1260
caactcgact acgtgaagtc ggaatcgcta gtaatcgcag atcagc                  1306

<210> SEQ ID NO 22
<211> LENGTH: 1542
<212> TYPE: DNA
<213> ORGANISM: Escherichia/Shigella

<400> SEQUENCE: 22
aaattgaaga gtttgatcat ggctcagatt gaacgctggc ggcaggccta acacatgcaa     60
gtcgaacggt aacaggaaga agcttgcttc tttgctgacg agtggcggac gggtgagtaa    120
tgtctgggaa actgcctgat ggagagggat aactactgga aacggtagct aataccgcat   180
aacgtcgcaa gaccaaagag ggggaccttc gggcctcttg ccatcggatg tgcccagatg   240
ggattagcta gtaggtgggg taacggctca cctaggcgac gatccctagc tggtctgaga   300
ggatgaccag ccacactgga actgagacac ggtccagact cctacgggag gcagcagtgg   360
ggaatattgc acaatgggcg caagcctgat gcagccatgc cgcgtgtatg aagaaggcct   420
tcgggttgta aagtactttc agcggggagg aaggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca   780
aacaggatta gataccctgg tagtccacgc cgtaaacgat gtcgacttgg aggttgtgcc    840
```

```
cttgaggcgt ggcttccgga gctaacgcgt taagtcgacc gcctggggag tacggccgca       900
aggttaaaac tcaaatgaat tgacgggggc ccgcacaagc ggtggagcat gtggtttaat       960
tcgatgcaac gcgaagaacc ttacctggtc ttgacatcca cagaactttc cagagatgga      1020
ttggtgcctt cgggaactgt gagacaggtg ctgcatggct gtcgtcagct cgtgttgtga      1080
aatgttgggt taagtcccgc aacgagcgca acccttatcc tttgttgcca gcggtccggc      1140
cgggaactca aaggagactg ccagtgataa actggaggaa ggtggggatg acgtcaagtc      1200
atcatggccc ttacgaccag ggctacacac gtgctacaat ggcgcataca aagagaagcg      1260
acctcgcgag agcaagcgga cctcataaag tgcgtcgtag tccggattgg agtctgcaac      1320
tcgactccat gaagtcggaa tcgctagtaa tcgtggatca gaatgccacg gtgaatacgt      1380
tcccgggcct tgtacacacc gcccgtcaca ccatgggagt gggttgcaaa agaagtaggt      1440
agcttaacct tcgggagggc gcttaccact ttgtgattca tgactggggt gaagtcgtaa      1500
caaggtaacc gtaggggaac ctgcggttgg atcacctcct ta                         1542
```